US007129239B2

(12) United States Patent
Griffith

(10) Patent No.: US 7,129,239 B2
(45) Date of Patent: Oct. 31, 2006

(54) PURINE COMPOUNDS AND USES THEREOF

(75) Inventor: David A. Griffith, Old Saybrook, CT (US)

(73) Assignee: Pfizer Inc., New York, NY (US)

( * ) Notice: Subject to any disclaimer, the term of this patent is extended or adjusted under 35 U.S.C. 154(b) by 333 days.

(21) Appl. No.: 10/689,381

(22) Filed: Oct. 20, 2003

(65) Prior Publication Data

US 2004/0092520 A1 May 13, 2004

Related U.S. Application Data

(60) Provisional application No. 60/421,874, filed on Oct. 28, 2002.

(51) Int. Cl.
*C07D 473/34* (2006.01)
*C07D 473/30* (2006.01)
*A61K 31/52* (2006.01)
*A61K 31/522* (2006.01)
*A61K 3/04* (2006.01)

(52) U.S. Cl. .................... 514/234.2; 544/118; 544/230; 544/265; 544/267; 544/277; 544/317; 544/329; 544/264; 514/263.4; 514/263.2; 514/263.22; 514/263.23; 514/263.34

(58) Field of Classification Search ............. 514/234.2, 514/263.2, 263.22, 263.23, 263.34, 263.4; 544/230, 267, 118, 265, 277
See application file for complete search history.

(56) References Cited

U.S. PATENT DOCUMENTS 3,016,378 A 1/1962 Roch et al. .............. 260/247.5
3,457,263 A 7/1969 Regnier et al. ............. 260/252
3,850,917 A 11/1974 Muller et al. ............... 260/243
4,459,296 A 7/1984 Ancher et al. .............. 424/244
4,728,644 A 3/1988 Yuki et al. .................. 514/212
4,925,846 A 5/1990 Deacon et al.
4,944,790 A 7/1990 Moser et al.
5,057,517 A 10/1991 Johnston et al. ............ 514/254
5,134,142 A 7/1992 Matsuo et al.
5,256,398 A 10/1993 McAfee et al. ................ 424/9
5,462,960 A 10/1995 Barth et al.
5,596,106 A 1/1997 Cullinan et al.
5,624,941 A 4/1997 Barth et al.
5,744,491 A 4/1998 Boigegrain et al.
5,744,493 A 4/1998 Boigegrain et al.
5,747,524 A 5/1998 Cullinan et al.
5,925,768 A 7/1999 Barth et al.
6,028,084 A 2/2000 Barth et al.
6,100,259 A 8/2000 Xiang et al.
6,166,016 A 12/2000 Okamura et al. ........... 514/246
6,284,748 B1 9/2001 Dang et al. ................... 514/81
6,344,474 B1 2/2002 Maruani et al.
6,355,631 B1 3/2002 Achard et al.
6,432,984 B1 8/2002 Barth et al.
6,476,060 B1 11/2002 Lange et al.
6,479,479 B1 11/2002 Achard et al.
6,509,367 B1 1/2003 Martin et al.
6,518,264 B1 2/2003 Achard et al.
6,566,356 B1 5/2003 Achard et al.
6,579,868 B1 6/2003 Asano et al. .......... 514/211.08
6,841,549 B1 * 1/2005 Asano et al. ............... 514/183
2001/0027193 A1 10/2001 Achard et al.
2001/0053788 A1 12/2001 Lange et al.
2002/0019383 A1 2/2002 Achard et al.
2002/0019421 A1 2/2002 Biberman et al.
2002/0035102 A1 3/2002 Achard et al.
2002/0091114 A1 7/2002 Plot-Grosjean et al.
2002/0119972 A1 8/2002 Leftheris et al.
2002/0128302 A1 9/2002 Maruani et al.
2002/0188007 A1 12/2002 Barth et al.
2003/0003145 A1 1/2003 Abramovici et al.
2003/0055033 A1 3/2003 Achard et al.
2003/0114495 A1 6/2003 Finke et al.
2003/0139386 A1 7/2003 Cote et al.
2003/0199536 A1 10/2003 Thomas et al.
2004/0072833 A1 4/2004 Nakai et al.
2004/0077650 A1 4/2004 Dow .......................... 514/242
2005/0043327 A1 * 2/2005 Coe et al. ............. 514/263.22

FOREIGN PATENT DOCUMENTS

CA 2387138 4/2001

(Continued)

OTHER PUBLICATIONS

Miles et al. Diabetes Care 25 (7): 1123.*

(Continued)

*Primary Examiner*—Mark L. Berch
(74) *Attorney, Agent, or Firm*—Gregg C. Benson; Arlene K. Musser

(57) ABSTRACT

Compounds of Formula (I) that act as cannabinoid receptor ligands and their uses in the treatment of diseases linked to the mediation of the cannabinoid receptors in animals are described herein.

(I)

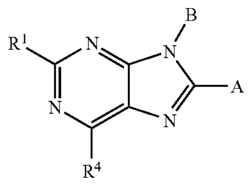

wherein A is an optionally substituted aryl or an optionally substituted heteroaryl; B is an optionally substituted aryl or an optionally substituted heteroaryl; $R^1$ is hydrogen, $(C_1-C_4)$alkyl, halo-substituted $(C_1-C_4)$alkyl, or $(C_1-C_4)$alkoxy; and $R^4$ is as described herein.

57 Claims, No Drawings

FOREIGN PATENT DOCUMENTS

| | | | |
|---|---|---|---|
| EP | 293220 | B1 | 8/1994 |
| EP | 1054012 | | 12/1998 |
| EP | 1221444 | | 6/2000 |
| EP | 1354884 | | 10/2003 |
| WO | WO 96/02248 | A1 | 2/1996 |
| WO | WO 00/15609 | A1 | 5/2000 |
| WO | WO 01/24798 | A1 | 4/2001 |
| WO | WO 01/029007 | A1 | 4/2001 |
| WO | WO 01/032629 | A1 | 5/2001 |
| WO | WO 01/032663 | A2 | 5/2001 |
| WO | WO 01/58450 | A2 | 8/2001 |
| WO | WO 01/85092 | A2 | 11/2001 |
| WO | WO02053565 | | 7/2002 |
| WO | WO 02/076949 | A1 | 10/2002 |
| WO | WO 03/006007 | A1 | 1/2003 |
| WO | WO 03/007887 | A2 | 1/2003 |
| WO | WO 03/018060 | A1 | 3/2003 |
| WO | WO 03/020217 | A2 | 3/2003 |
| WO | WO 03/020314 | A1 | 3/2003 |
| WO | WO 03/026647 | A1 | 4/2003 |
| WO | WO 03/026648 | A1 | 4/2003 |
| WO | WO 03/027069 | A1 | 4/2003 |
| WO | WO 03/027076 | A2 | 4/2003 |
| WO | WO 03/027114 | A1 | 4/2003 |
| WO | WO 03/040107 | A1 | 5/2003 |
| WO | WO 03/051850 | A1 | 6/2003 |
| WO | WO 03/051851 | A1 | 6/2003 |
| WO | WO 03/075660 | A1 | 9/2003 |
| WO | WO 03/077847 | A2 | 9/2003 |
| WO | WO 03/078413 | A1 | 9/2003 |
| WO | WO 03/082190 | A2 | 10/2003 |
| WO | WO 03/082191 | A2 | 10/2003 |
| WO | WO 03/082256 | A2 | 10/2003 |
| WO | WO 03/082833 | A1 | 10/2003 |
| WO | WO 03/084943 | A2 | 10/2003 |
| WO | WO 03/086288 | A2 | 10/2003 |
| WO | WO 03/087037 | A1 | 10/2003 |
| WO | WO03095455 | | 11/2003 |

OTHER PUBLICATIONS

Hollander et al. Diabetes Care 21 (8): 1288.*

Fujioka, K., et al., Diabetes, Obesity and Metabolism vol. 2 p. 175-187 May 2000.*

Tanju, Ken-ichi, et al., *Heterocycles*, "Purines. IX.1 Reation of 9-Phenyl-9H-Purine—2-Carbonitriles with Grignard Reagents", vol. 30, (1), pp. 435-440 (1990).

Halpern, et al., *Obesity Reviews*, "Treatment of Obesity: An Update On Anti-Obesity Medications", vol. 4, pp. 25-42 (2003).

Chorvat, et al., *J. Med. Chem.*, "Synthesis, Corticortropin-Releasing Factor Receptor Binding Affinity, and Pharmacokinetic Properties of Triazolo,-Imidazo-, and Pyrrolopyrimidines and —Pyridines", vol. 42, pp. 833-848 (1999).

Legraverend, et al., *Bioorganic & Medicinal Chemistry Letters*, "Synthesis of C2 Alkylnylated Purines, A New Family of Potent Inhibitors of Cyclin-Dependent Kinases", vol. 8, pp. 793-798 (1998).

Camaionl, et al., *Bioorganic & Medicinal Chemistry*, "New Substituted 9-Alkylpurines as Adenosine Receptor Ligands", vol. 6, pp. 523-533 (1998).

Young, et al., *J. Med. Chem.*, "Purine Derivatives as Competitive Inhibitors of Human Erythrocyte Membrane Phosphatitdylinositol 4-Kinase", vol. 33, pp. 2073-2080 (1990).

Montgomery, et al., *Journal of the American Chemical Society*, "Synthesis of Potential Anticancer Agents. XXVI. The Alkylation of 6-Choloropurine", vol. 83, pp. 630-635 (1960).

Koppel, et al., *Journal of Organic Chemistry*, "Potential Purine Antagonists. XIII. Synthesis of Some 8-Methylpurines", vol. 23, pp. 1457-1460 (Oct. 1958).

Ding, et al., *Tetrahedron Letters*, "Expanding the Diversity of Purine Libraries", vol. 42, pp. 8751-8755 (2001).

Tzavara, E.T., et al., "The CB1 Receptor Antagonist SR141716A selectively increases monoaminergic neurotransmission in the medical prefrontal cortex: Implications for Therapeutic Actions," *J Pharmacol*, 138, 544-553 (2003).

Racz, I., et al., "A Critical Role for the Cannabinoid CB1 Receptors in Alcohol Dependence and Stress-Stimulated Ethanol Drinking," *J Neurosci*, 23(6), 2453-2458 (2003).

Croci, T., et al., "Role of Cannabinoid CB1 Receptors and Tumor Necrosis Factor-$\alpha$ in the gut and systemic anti-inflammatory activity of SR 141716 (Rimonabant) in rodents," *Brit J Pharmacol*, 140, 115-122 (2003).

DaSilva, G.E., et al., "Potentiation of Penile Erection and Yawning Responses to Apomorphine by Cannabinoid Receptor Antagonists in Rats," *Neurosci Let*, 349, 49-52 (2003).

Wang, L., et al., "Endocannabinoid Signaling via Cannabinoid Receptor 1 is Involved in Ethanol Preference and its Age-Dependent Decline in Mice," *PNAS*, 100(3), 1393-1398 (2003).

Ruiu, S., et al., "Synthesis and Charaterization of NESS 0327: A Novel Putative Antagonist of the CB1 Cannabinoid Receptor," *J Pharmacol Exp Therap*, 306, 363-370 (2003).

Howlett, A.C., et al., "International Union of Pharmacology. XXVII. Classification of Cannabinoid Receptors," *Pharmacol Rev*, 54, 161-202 (2002).

Gomez, R., et al., "A Peripheral Mechanism for CB1 Cannabinoid Receptor-Dependent Modulation of Feeding," *J. Neurosci*, 22(21), 9612-9617 (2002).

Wiley, J.L., et al., "Novel Pyrazole Cannabinoids: Insights into CB1 Receptor Recognition and Activation," *J Pharmacol Exp Therap*, 296(3), 1013-1022 (2001).

Lellemand, F., et al., "Effects of CB1 Cannabinoid Receptor Blockade on Ethanol Preference After Chronic Ethanol Administration," *Alcohol Clin Exp Res*, 25(9), 1317-1323 (2001).

Pertwee, R.G., "Cannabinoids and the Gastrointestinal Tract," *Gut*, 48, 859-867 (2001).

Pertwee, R.G., "Cannabinoid Receptor Ligands: Clinical and Neuropharmacological Considerations, Relevant to Future Drug Discovery and Development," *Exp. Opin. Invest. Drugs*, 9(7), 1573-1571 (2000).

Hungund, B.L and B.S. Basavarajappa, "Are Anadamide and Cannabinoid Receptors involved in Ethanol Tolerance? A Review of the Evidence," *Alcohol & Alcoholism*. 35(2) 126-133, (2000).

Freedland, C.S., et al., "Effects of SR141716A, a Central Cannabinoid Receptor Antagonist , on Food-maintained Responding," *Pharmacol Biochem Behav*, 67, 265-270 (2000).

Lan, R., et al., "Structure-Activity Relationships of Pyrazole Derivatives as Cannabinoid Receptor Antagonists" *J. Med. Che.m*, 42, 769-776 (1999).

Pertwee, R.G., "Pharmacology of Cannabinoid Receptor Ligands" *Curr Med Chem*, 6, 635-664 (1999).

Basavarajappa, B.S., et al., "Chronic Ethanol Administration Downregulates Cannabinoid Receptors in Mouse Brain Synaptic Plasma Membrane," *Brain Res*, 793, 212-218 (1998).

Thomas, B.F., et al., "Comparative Receptor Binding Analyses of Cannabinoid Agonists and Antagonists," *J Pharmacol Exp Therap*, 285, 285-292 (1998).

Colombo, G., et al., "Appetite Suppression and Weight Loss after the Cannabinoid Antagonist SR141716," *Life Sci.*, 63, PL113-PL117 (1998).

Simiand, J., et al., "SR141716, a CB1 Cannabinoid Receptor Antagonist, Selectively Reduces Sweet Food Intake in Marmose," *Behav. Pharmacol.*, 9, 179-181 (1998).

Chaperon, F., et al., "Involvement of Central Cannabinoid (CB1) Receptors in the Establishment of Place Conditioning in Rats," *Psychopharmacology*, 135, 324-332 (1998).

Arnone, M., et al., "Selective Inhibition of Sucrose and Ethanol Intake by SR141716, an Antagonist of Central Cannabinoid (CB1) Receptors," *Psychopharmacol*, 132, 104-106 (1997).

Savontaus, e., et al., "Anti-Obesity Effect of MPV-1743 A III, a Novel Imidazoline Derivative, in Genetic Obesity," *Eur J Pharmacol*, 328, 207-215 (1997).

Sanudo-Pena, M.C., et al., "Endogenous Cannabinoids as an Aversive or Counter-rewarding System in the Rat," *Neurosci Let*, 223, 125-128 (1997).

Gifford, A.N., et al., "Electrically Evoked Acetylcholine Relase from Hippocampal Silices is Inhibited by the Cannabinoid Antagonist, SR 141716A," *J Pharmacol Exp Ther*, 277, 1431-1436 (1996).
Compton, D.R., et al., "In Vivo Characterization of a Specific Cannabinoid Receptor Antagonist (SR141716A); Inhibition of Delta-9-Tetrahydrocannabinol-Induced Responses and Apparent Agonist Activity," *J Pharmacol Exp Ther*, 277, 586-594 (1996).
Mansbach, R.S., et al., "Effects of the Cannabinoid CB1 Receptor Antagonist SR141716A on the Behavior of Pigeons and Rats," *Psychopharmacology*, 124, 315-322 (1996).
Lichtman, A.H. et al., "Delta-9-Tetrahydrocannabinol Impairs Spatial Memory through a Cannabinoid Receptor Mechanism," *Psychopharmacology*, 126, 125-131 (1996).
Perio, A., et al., "Central Mediation of the Cannabinoid Cue: Activity of a Selective CB1 Antagonist, SR141716A," *Behavioral Pharmacology*, 7, 65-71 (1996).
Rinaldi-Carmona, M., et al., "Biochemical and Pharmacological Characterization of SR141716A, The First Potent and Selective Brain Cannabinoid Receptor Antagonist," *Life Sci*, 56, 1941-1947 (1995).
Pertwee, R., et al., "AM630, A Competitive Cannabinoid Receptor Antagonist," *Life Sci*, 56, 1949-1955 (1995).
Rinaldi-Carmona, M., et al., "SR141716A, a Patent and Selective Antagonist of the Brain Cannabinoid Receptor," *FEBS Letters*, 350, 240-244 (1994).
Dutta, A., et al., "The Synthesis and Pharmacological Evaluation of the Cannabinoid Antagonist SR 141716A", *Med. Chem. Rev.* 5, 54-62 (1994).
Drummond, J., et al., "Evaluation and Synthesis of Aminohydroxyisoxazoles and Pyrazoles as Potential Glycine Agonists," *J. Med. Chem*, 32, 2116-2128 (1989).
Murray, W., et al., "A Simple Regioselective Synthesis of Ethyl 1,5-Diarylpyrazole-3-carboxylates" *J. Heterocyclic Chem*, 26, 1389 (1989).
Dewey, W.L. "Cannabinoid Pharmacology," *Pharmacological Reviews*, 38(2)m 151-178 (1986).
Tewari, R.S., et al., "1,3-Dipolar Cycloaddition and Nucleophylic Substitution Reactions of C-Acetyl and C-Ethoxycarbonyl Derivative of Hydrazidoyl Bromides" *Tetrahedron*, 29(1) 129-136 (1983).
Birkofer, L. and K. Richtzenhain, "Silyl-Derivate von Pyrazol, Isoxazol und 1,2,3-Triazol" *Chem. Ber.* 112, 2829-2836 (1979).
Franke, H. et al., "Polare Cycloadditionen von elektronenreichen Mehrfach-bindungssystemen an 1,3,4-oxadiazolium-Salze: Synthese von 3aH-[1,3,4]Oxadiazolo[3,2-a]chinolinen" *Chem. Ber.* 112, 3623-3636 (1979).
Sucrow, W., et al., "Bimolekulare Cyclisierung von 2-(1-Methylhydrazino)maleinsaure-dimethylester" *Chem. Ber.* 112, 1712-1718 (1979).
Bastaki, S., *Int. J. Diabetes & Metabolism*, "Diabetes Mellitus and Its Treatment", vol. 13, pp. 111-134 (2005).

* cited by examiner

PURINE COMPOUNDS AND USES THEREOF

This application claims the benefit of U.S. Provisional Application No. 60/421,874 filed on Oct. 28, 2002 and incorporated herein by reference in its entirety.

FIELD OF THE INVENTION

The present invention relates to purine compounds and intermediates useful in the synthesis of the purine compounds. The purine compounds are useful as cannabinoid receptor ligands, in particular as CB-1 receptor antagonists. As a result, the present invention also relates to the use of the purine compounds in treating diseases, conditions and disorders modulated by cannabinoid receptor ligands including pharmaceutical compositions for such use.

BACKGROUND

Obesity is a major public health concern because of its increasing prevalence and associated health risks. Obesity and overweight are generally defined by body mass index (BMI), which is correlated with total body fat and estimates the relative risk of disease. BMI is calculated by weight in kilograms divided by height in meters squared ($kg/^2$). Overweight is typically defined as a BMI of 25–29.9 $kg/^2$, and obesity is typically defined as a BMI of 30 $kg/m^2$. See, e.g., National Heart, Lung, and Blood Institute, Clinical Guidelines on the Identification, Evaluation, and Treatment of Overweight and Obesity in Adults, The Evidence Report, Wash., D.C.: U.S. Department of Health and Human Services, NIH publication no.98-4083 (1998).

The increase in obesity is of concern because of the excessive health risks associated with obesity, including coronary heart disease, strokes, hypertension, type 2 diabetes mellitus, dyslipidemia, sleep apnea, osteoarthritis, gall bladder disease, depression, and certain forms of cancer (e.g., endometrial, breast, prostate, and colon). The negative health consequences of obesity make it the second leading cause of preventable death in the United States and impart a significant economic and psychosocial effect on society. See, McGinnis M, Foege W H., “Actual Causes of Death in the United States,” *JAMA,* 270, 2207–12 (1993).

Obesity is now recognized as a chronic disease that requires treatment to reduce its associated health risks. Although weight loss is an important treatment outcome, one of the main goals of obesity management is to improve cardiovascular and metabolic values to reduce obesity-related morbidity and mortality. It has been shown that 5–10% loss of body weight can substantially improve metabolic values, such as blood glucose, blood pressure, and lipid concentrations. Hence, it is believed that a 5–10% intentional reduction in body weight may reduce morbidity and mortality.

Currently available prescription drugs for managing obesity generally reduce weight by inducing satiety or decreasing dietary fat absorption. Satiety is achieved by increasing synaptic levels of norepinephrine, serotonin, or both. For example, stimulation of serotonin receptor subtypes 1B, 1D, and 2C and 1- and 2-adrenergic receptors decreases food intake by regulating satiety. See, Bray G A, “The New Era of Drug Treatment. Pharmacologic Treatment of Obesity: Symposium Overview,” *Obes Res.,* 3(suppl 4), 415s–7s (1995). Adrenergic agents (e.g., diethylpropion, benzphetamine, phendimetrazine, mazindol, and phentermine) act by modulating central norepinephrine and dopamine receptors through the promotion of catecholamine release. Older adrenergic weight-loss drugs (e.g., amphetamine, methamphetamine, and phenmetrazine), which strongly engage in dopamine pathways, are no longer recommended because of the risk of their abuse. Fenfluramine and dexfenfluramine, both serotonergic agents used to regulate appetite, are no longer available for use.

More recently, CB1 cannabinoid receptor antagonists/inverse agonists have been suggested as potential appetite suppressants. See, e.g., Arnone, M., et al., “Selective Inhibition of Sucrose and Ethanol Intake by SR141716, an Antagonist of Central Cannabinoid (CB1) Receptors,” *Psychopharmacol,* 132, 104–106 (1997); Colombo, G., et al., “Appetite Suppression and Weight Loss after the Cannabinoid Antagonist SR141716,” *Life Sci.,* 63, PL113–PL117 (1998); Simiand, J., et al., “SR141716, a CB1 Cannabinoid Receptor Antagonist, Selectively Reduces Sweet Food Intake in Marmose,” *Behav. Pharmacol.,* 9, 179–181 (1998); and Chaperon, F., et al., “Involvement of Central Cannabinoid (CB1) Receptors in the Establishment of Place Conditioning in Rats,” *Psychopharmacology,* 135, 324–332 (1998). For a review of cannabinoid CB1 and CB2 receptor modulators, see Pertwee, R. G., “Cannabinoid Receptor Ligands: Clinical and Neuropharmacological Considerations, Relevant to Future Drug Discovery and Development,” *Exp. Opin. Invest. Drugs,* 9(7), 1553–1571 (2000).

Although investigations are on-going, there still exists a need for a more effective and safe therapeutic treatment for reducing or preventing weight-gain.

In addition to obesity, there also exists an unmet need for treatment of alcohol abuse. Alcoholism affects approximately 10.9 million men and 4.4 million women in the United States. Approximately 100,000 deaths per year have been attributed to alcohol abuse or dependence. Health risks associated with alcoholism include impaired motor control and decision making, cancer, liver disease, birth defects, heart disease, drug/drug interactions, pancreatitis and interpersonal problems. Studies have suggested that endogenous cannabinoid tone plays a critical role in the control of ethanol intake. The endogenous CB1 receptor antagonist SR-141716A has been shown to block voluntary ethanol intake in rats and mice. See, Arnone, M., et al., “Selective Inhibition of Sucrose and Ethanol Intake by SR141716, an Antagonist of Central Cannabinoid (CB1) Receptors,” *Psychopharmacol,* 132, 104–106 (1997). For a review, see Hungund, B. L and B. S. Basavarajappa, “Are Anadamide and Cannabinoid Receptors involved in Ethanol Tolerance? A Review of the Evidence,” *Alcohol & Alcoholism.* 35(2) 126–133, 2000.

Current treatments for alcohol abuse or dependence generally suffer from non-compliance or potential hepatotoxicity; therefore, there is a high unmet need for more effective treatment of alcohol abuse/dependence.

SUMMARY

The present invention provides compounds of Formula (I) that act as cannabinoid receptor ligands (in particular, CB1 receptor antagonists)

(I)

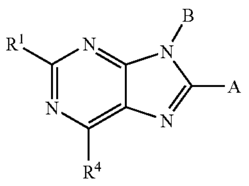

wherein

A is an optionally substituted aryl or an optionally substituted heteroaryl (preferably, A is a substituted phenyl, more preferably a phenyl substituted with one to three substituents independently selected from the group consisting of halo (preferably, chloro or fluoro), $(C_1-C_4)$alkoxy, $(C_1-C_4)$alkyl, halo-substituted $(C_1-C_4)$alkyl (preferably fluoro-substituted alkyl), and cyano, most preferably, A is 2-chlorophenyl, 2-fluorophenyl, 2,4-dichlorophenyl, 2-fluoro-4-chlorophenyl, 2-chloro-4-fluorophenyl, or 2,4-difluorophenyl);

B is an optionally substituted aryl or an optionally substituted heteroaryl (preferably, B is a substituted phenyl, more preferably a phenyl substituted with one to three substituents independently selected from the group consisting of halo (preferably, chloro or fluoro), $(C_1-C_4)$alkoxy, $(C_1-C_4)$alkyl, halo-substituted $(C_1-C_4)$alkyl (preferably fluoro-substituted alkyl), and cyano, most preferably, B is 4-chlorophenyl or 4-fluorophenyl);

$R^1$ is hydrogen, $(C_1-C_4)$alkyl, halo-substituted $(C_1-C_4)$alkyl, or $(C_1-C_4)$alkoxy;

$R^4$ is (i) a group having Formula (IA) or Formula (IB)

(IA)

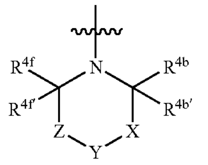

(IB)

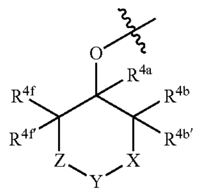

where $R^{4a}$ is hydrogen or $(C_1-C_3)$alkyl;

$R^{4b}$ and $R^{4b'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4$alkyl$)_2$N—C(O)—, $(C_1-C_6)$alkylamino-, $((C_1-C_4)$alkyl$)_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3- to 6-membered heterocycle, and a partially or fully saturated 3- to 8-membered carbocyclic ring, where the moiety is optionally substituted, or either $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, $—CH_2CH_2—$ or $—C(R^{4c})(R^{4c'})—$, where $R^{4c}$ and $R^{4c'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3- to 6-membered heterocycle, and a partially or fully saturated 3- to 8-membered carbocyclic ring, where the moiety is optionally substituted, or either $R^{4c}$ or $R^{4c'}$ taken together with $R^{4e}$, $R^{4e'}$, $R^{4f}$, or $R^{4f'}$ forms a bond, a methylene bridge or an ethylene bridge;

Y is oxygen, sulfur, —C(O)—, —C(=N—OH)—, or $—C(R^{4d})(R^{4d'})—$, where $R^{4d}$ and $R^{4d'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, HO—NH—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3- to 6-membered heterocycle, and a partially or fully saturated 3- to 8-membered carbocyclic ring, where the moiety is optionally substituted, or $R^{4d}$ and $R^{4d'}$ taken together form a partially or fully saturated, 3- to 6-membered heterocyclic ring, a 5- or 6-membered lactone ring, or a 4- to 6-membered lactam ring, where the heterocyclic ring, the lactone ring and the lactam ring are optionally substituted and the lactone ring and the lactam ring optionally contain an additional heteroatom selected from oxygen, nitrogen or sulfur, or Y is $—NR^{4d''}—$, where $R^{4d''}$ is a hydrogen or a chemical moiety selected from the group consisting of $(C_1-C_6)$alkyl, $(C_3-C_6)$cycloalkyl, $(C_1-C_3)$alkylsulfonyl-, $(C_1-C_3)$alkylaminosulfonyl-, di$(C_1-C_3)$alkylaminosulfonyl-, acyl, $(C_1-C_6)$alkyl-O—C(O)—, aryl, and heteroaryl, where the moiety is optionally substituted;

Z is a bond, $—CH_2CH_2—$, or $—C(R^{4e})(R^{4e'})—$, where $R^{4e}$ and $R^{4e'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3- to 6-membered heterocycle, and a partially or fully saturated 3- to 8-membered carbocyclic ring, where the moiety is optionally substituted, or either $R^{4e}$ or $R^{4e'}$ taken together with $R^{4b}$, $R^{4b'}$, $R^{4c}$, or $R^{4c'}$ forms a bond, a methylene bridge or an ethylene bridge; and $R^{4f}$ and $R^{4f'}$ are each independently hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)$alkyl$)_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3- to 6-membered heterocycle, and a partially or fully saturated 3- to 8-membered carbocyclic ring, where the moiety is optionally substituted, or either $R^{4f}$ or $R^{4f'}$ taken together with $R^{4b}$, $R^{4b'}$, $R^{4c}$, or $R^{4c'}$ forms a bond, a methylene bridge or an ethylene bridge;

provided that when $R^4$ is a group of Formula (IA), then (a) at least one of $R^{4b}$, $R^{4b'}$, $R^{4c}$, $R^{4c'}$, $R^{4d}$, $R^{4d'}$, $R^{4d''}$, $R^{4e}$, $R^{4e'}$, $R^{4f}$ and $R^{4f'}$ and is other than hydrogen, $(C_1-C_4)$alkyl, or halo-substituted $(C_1-C_4)$alkyl; and (b) Y is not oxygen, sulfur or —NH—, when X and Z are a bond, —$CH_2$— or —$CH_2CH_2$—, and $R^{4b}$, $R^{4b'}$, $R^{4f}$ and $R^{4f'}$ are hydrogen; or (ii) a group having Formula (IC)

(IC)

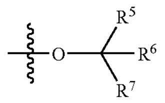

where $R^5$ and $R^6$ are each independently hydrogen or $(C_1-C_4)$alkyl, and $R^7$ is $(C_1-C_4)$alkyl-, halo-substituted $(C_1-C_4)$alkyl-, $(C_1-C_4)$alkoxy$(C_1-C_4)$alkyl-, $(C_1-C_4)$alkylamino$(C_1-C_4)$alkyl-, di$(C_1-C_4)$alkylamino$(C_1-C_4)$alkyl-, or a partially or fully saturated 4- to 6-membered heterocylic ring containing 1 to 2 heteroatoms independently selected from oxygen, sulfur or nitrogen, or $R^5$ and $R^6$ or $R^5$ and $R^7$ taken together form a 5- or 6-membered lactone, 4- to 6-membered lactam, or a 4- to 6-membered partially or fully saturated heterocycle containing 1 to 2 heteroatoms independently selected from oxygen, sulfur or nitrogen, where the lactone, the lactam and the heterocycle are optionally substituted;

a pharmaceutically acceptable salt thereof, a prodrug of the compound or the salt, or a solvate or hydrate of the compound, the salt or the prodrug.

A preferred compound of the present invention is a compound of Formula (I) where $R^4$ is a group of Formula (IA). Preferably, $R^{4b}$ and $R^{4b'}$ are each independently hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a partially or fully saturated 3- to 6-membered heterocycle, and a partially or fully saturated 3- to 8-membered carbocyclic ring, where the moiety is optionally substituted, or $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, —$CH_2CH_2$— or —$C(R^{4c})(R^{4c'})$—, where $R^{4c}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl)$_2$N—C(O)—, $(C_1-C_6)$alkylamino-, $((C_1-C_4)$alkyl)$_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3- to 6-membered heterocycle, and a partially or fully saturated 3- to 8-membered carbocyclic ring, where the moiety is optionally substituted, or $R^{4c}$ taken together with $R^{4e}$, $R^{4e'}$, $R^{4f}$, or $R^{4f'}$ forms a bond, a methylene bridge, or an ethylene bridge, and $R^{4c'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a partially or fully saturated 3- to 6-membered heterocycle, and a partially or fully saturated 3- to 8-membered carbocyclic ring, where the moiety is optionally substituted, or $R^{4c'}$ taken together with $R^{4e}$, $R^{4e'}$, $R^{4f}$, or $R^{4f'}$ forms a bond, a methylene bridge, or an ethylene bridge;

Y is oxygen, sulfur, —C(O)—, or —$C(R^{4d})(R^{4d'})$—, where $R^{4d}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl)$_2$N—C(O)—, $(C_1-C_6)$alkylamino-, $((C_1-C_4)$alkyl)$_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3- to 6-membered heterocycle, and a partially or fully saturated 3- to 8-membered carbocyclic ring, where the moiety is optionally substituted, and $R^{4d'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a partially or fully saturated 3- to 6-membered heterocycle, and a partially or fully saturated 3- to 8-membered carbocyclic ring, where the moiety is optionally substituted, or $R^{4d}$ and $R^{4d'}$ taken together form a partially or fully saturated, 3- to 6-membered heterocyclic ring, a 5- or 6-membered lactone ring, or a 4- to 6-membered lactam ring, where the heterocyclic ring, the lactone ring and the lactam ring are optionally substituted and the lactone ring and the lactam ring optionally contain an additional heteroatom selected from oxygen, nitrogen or sulfur, or Y is —$NR^{4d''}$—, where $R^{4d''}$ is a hydrogen or a chemical moiety selected from the group consisting of $(C_1-C_6)$alkyl, $(C_3-C_6)$cycloalkyl, $(C_1-C_3)$alkylsulfonyl-, $(C_1-C_3)$alkylaminosulfonyl-, di$(C_1-C_3)$alkylaminosulfonyl-, acyl, $(C_1-C_6)$alkyl-O—C(O)—, aryl, and heteroaryl, where the moiety is optionally substituted;

Z is a bond, —$CH_2CH_2$—, or —$C(R^{4e})(R^{4e'})$—, where $R^{4e}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl)$_2$N—C(O)—, $(C_1-C_6)$alkylamino-, $((C_1-C_4)$alkyl)$_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3- to 6-membered heterocycle, and a partially or fully saturated 3- to 8-membered carbocyclic ring, where the moiety is optionally substituted, or $R^{4e}$ taken together with $R^{4b}$, $R^{4b'}$, $R^{4c}$, or $R^{4c'}$ forms a bond, a methylene bridge, or an ethylene bridge, and $R^{4e'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a partially or fully saturated 3- to 6-membered heterocycle, and a partially or fully saturated 3- to 8-membered carbocyclic ring, where the moiety is optionally substituted, or $R^{4e'}$ taken together with $R^{4b}$, $R^{4b'}$, $R^{4c}$, or $R^{4c'}$ forms a bond, a methylene bridge, or an ethylene bridge; and $R^{4f}$ and $R^{4f'}$ are each independently hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)$alkyl)$_2$N—C(O)—, aryl, heteroaryl, a partially or fully saturated 3- to 6-membered heterocycle, and a partially or fully saturated 3- to 8-membered carbocyclic ring, where the moiety is optionally substituted, or $R^{4f}$ or $R^{4f'}$ taken together with $R^{4b}$, $R^{4b'}$, $R^{4c}$, or $R^{4c'}$ forms a bond, a methylene bridge, or an ethylene bridge;

a pharmaceutically acceptable salt thereof, a prodrug of the compound or the salt, or a solvate or hydrate of the compound, the salt or the prodrug.

Preferably, $R^{4b}$ is hydrogen, an optionally substituted $(C_1–C_3)$alkyl, or taken together with $R^{4e}$, $R^{4e'}$, $R^{4f}$, or $R^{4f'}$ forms a bond, a methylene bridge, or an ethylene bridge; $R^{4b'}$ is hydrogen, an optionally substituted $(C_1–C_3)$alkyl, or taken together with $R^{4e}$, $R^{4e'}$, $R^{4f}$, or $R^{4f'}$ forms a bond, a methylene bridge, or an ethylene bridge; $R^{4f}$ is hydrogen, an optionally substituted $(C_1–C_3)$alkyl, or taken together with $R^{4b}$, $R^{4b'}$, $R^{4c}$, or $R^{4c'}$ forms a bond, a methylene bridge, or an ethylene bridge; and $R^{4f'}$ is hydrogen, an optionally substituted $(C_1–C_3)$alkyl, or taken together with $R^{4b}$, $R^{4b'}$, $R^{4c}$, or $R^{4c'}$ forms a bond, a methylene bridge, or an ethylene bridge, and even more preferably, $R^{4b}$, $R^{4b'}$, $R^{4f}$, and $R^{4f'}$ are all hydrogen.

When Y is —$NR^{4d''}$—, then $R^{4d''}$ is preferably a hydrogen or a chemical moiety selected from the group consisting of $(C_1–C_6)$alkyl, $(C_3–C_6)$cycloalkyl, $(C_1–C_3)$alkylsulfonyl, $(C_1–C_3)$alkylaminosulfonyl, di$(C_1–C_3)$alkylaminosulfonyl, acyl, $(C_1–C_6)$alkyl-O—C(O)—, aryl, and heteroaryl, where the moiety is optionally substituted (more preferably, $R^{d''}$ is a hydrogen or a chemical moiety selected from the group consisting of $(C_1–C_3)$alkylsulfonyl, $(C_1–C_3)$alkylaminosulfonyl, di$(C_1–C_3)$alkylaminosulfonyl, acyl, $(C_1–C_6)$alkyl-O—C(O)—, and heteroaryl, where the moiety is optionally substituted (preferably the $(C_1–C_3)$alkylsulfonyl, $(C_1–C_3)$alkylaminosulfonyl, di$(C_1–C_3)$alkylaminosulfonyl, acyl, and $(C_1–C_6)$alkyl-O—C(O)— are optionally substituted with 1 to 3 fluorines, and the heteroaryl is optionally substituted with 1 to 2 substituents independently selected from the group consisting of chloro, fluoro, $(C_1–C_3)$alkoxy, $(C_1–C_3)$alkyl, and fluoro-substituted $(C_1–C_3)$alkyl);

X is —$C(R^{4c})(R^{4c'})$—, where $R^{4c}$ and $R^{4c'}$ are each independently hydrogen, $H_2NC(O)$—, an optionally substituted $(C_1–C_6)$alkyl, $(C_1–C_4)$alkyl-NH—C(O)—, or $((C_1–C_4)alkyl)_2N$—C(O)—, or either $R^{4c}$ or $R^{4c'}$ taken together with $R^{4e}$, $R^{4e'}$, $R^{4f}$, or $R^{4f'}$ forms a bond, a methylene bridge or an ethylene bridge; and Z is —$C(R^{4e})(R^{4e'})$—, where $R^{4e}$ and $R^{4e'}$ are each independently hydrogen, $H_2NC(O)$—, an optionally substituted $(C_1–C_6)$alkyl, $(C_1–C_4)$alkyl-NH—C(O)—, or $((C_1–C_4)alkyl)_2N$—C(O)—, or either $R^{4e}$ or $R^{4e'}$ taken together with $R^{4b}$, $R^{4b'}$, $R^{4c}$, or $R^{4c'}$ forms a bond, a methylene bridge or an ethylene bridge.

When Y is —$C(R^{4d})(R^{4d'})$—, then $R^{4d}$ is hydrogen, cyano, hydroxy, amino, $H_2NC(O)$—, or a chemical moiety selected from the group consisting of $(C_1–C_6)$alkyl, $(C_1–C_6)$alkoxy, acyloxy, acyl, $(C_1–C_3)$alkyl-O—C(O)—, $(C_1–C_4)$alkyl-NH—C(O)—, $(C_1–C_4)alkyl)_2N$—C(O)—, $(C_1–C_6)$alkylamino-, $((C_1–C_4)alkyl)_2$amino-, $(C_3–C_6)$cycloalkylamino-, acylamino-, aryl$(C_1–C_4)$alkylamino-, heteroaryl$(C_1–C_4)$alkylamino-, aryl, heteroaryl, a partially or fully saturated 3- to 6membered heterocycle, and a partially or fully saturated 3- to 8-membered carbocyclic ring, where the moiety is optionally substituted (preferably, $R^{4d}$ is amino, $(C_1–C_6)$alkylamino, di$(C_1–C_4)$alkylamino, $(C_3–C_6)$cycloalkylamino, acylamino, aryl$(C_1–C_4)$alkylamino-, or heteroaryl$(C_1–C_4)$alkylamino, more preferably, $R^{4d}$ is amino, $(C_1–C_6)$alkylamino, di$(C_1–C_4)$alkylamino, $(C_3–C_6)$cycloalkylamino), and $R^{4d'}$ is hydrogen, $H_2NC(O)$—, or a chemical moiety selected from the group consisting of $(C_1–C_6)$alkyl, acyl, $(C_1–C_3)$alkyl-O—C(O)—, $(C_1–C_4)$alkyl-NH—C(O)—, $(C_1–C_4)alkyl)_2N$—C(O)—, aryl, heteroaryl, a partially or fully saturated 3- to 6-membered heterocycle, and a partially or fully saturated 3- to 8-membered carbocyclic ring, where the moiety is optionally substituted (preferably, $R^{4d'}$ is $(C_1–C_6)$alkyl, $H_2NC(O)$—, $(C_1–C_4)$alkyl-NH—C(O)—, or $((C_1–C_4)alkyl)_2N$—C(O)—, or aryl, more preferably, $R^{4d'}$ is $H_2NC(O)$—, $(C_1–C_4)$alkyl-NH—C(O)—, or $((C_1–C_4)alkyl)_2$ N—C(O)—), or $R^{4d}$ and $R^{4d'}$ taken together form a partially or fully saturated, 3- to 6-membered heterocyclic ring, a 5- to 6-membered lactone ring, or a 4- to 6-membered lactam ring, where the heterocyclic ring, the lactone ring and the lactam ring are optionally substituted and the lactone ring and the lactam ring optionally contain an additional heteroatom selected from oxygen, nitrogen or sulfur;

X is a bond or —$C(R^{4c})(R^{4c'})$—, where $R^{4c}$ and $R^{4c'}$ are each hydrogen; and Z is a bond or —$C(R^{4e})(R^{4e'})$—, where $R^{4e}$ and $R^{4e'}$ are each hydrogen.

Another preferred embodiment is a compound where Y is —$C(R^{4d})(R^{4d'})$—, $R^{4b}$, $R^{4b'}$, $R^{4f}$, and $R^{4f'}$ are all hydrogen; $R^{4d}$ is hydrogen, hydroxy, amino, or a chemical moiety selected from the group consisting of $(C_1–C_6)$alkyl, $(C_1–C_6)$alkoxy, acyloxy, acyl, $(C_1–C_3)$alkyl-O—C(O)—, $(C_1–C_6)$alkylamino-, and di$(C_1–C_4)$alkylamino-, where the moiety is optionally substituted (preferably, $R^{4d}$ is hydrogen, hydroxy, amino, or a chemical moiety selected from the group consisting of $(C_1–C_6)$alkoxy, acyl, $(C_1–C_6)$alkylamino-, and di$(C_1–C_4)$alkylamino-); and $R^{4d'}$ is hydrogen, or a chemical moiety selected from the group consisting of $(C_1–C_6)$alkyl, aryl and heteroaryl, where the moiety is optionally substituted (preferably, $R^{4d'}$ is hydrogen, or a chemical moiety selected from the group consisting of $(C_1–C_6)$alkyl and aryl, where the moiety is optionally substituted). In this embodiment, X is preferably —$C(R^{4c})(R^{4c'})$—, where $R^{4c}$ and $R^{4c'}$ are each independently hydrogen or an optionally substituted $(C_1–C_6)$alkyl, or either $R^{4c}$ or $R^{4c'}$ taken together with $R^{4e}$ or $R^{4e'}$ forms a bond, a methylene bridge or an ethylene bridge (preferably, $R^{4c}$ and $R^{4c'}$ are each hydrogen or either $R^{4c}$ or $R^{4c'}$ taken together with $R^{4e}$ or $R^{4e'}$ forms a bond); and Z is preferably —$C(R^{4e})(R^{4e'})$—, where $R^{4e}$ and $R^{4e'}$ are each independently hydrogen or an optionally substituted $(C_1–C_6)$alkyl, or either $R^{4e}$ or $R^{4e'}$ taken together with $R^{4c}$ or $R^{4c'}$ forms a bond, a methylene bridge or an ethylene bridge (preferably, $R^{4e}$ and $R^{4e'}$ are each hydrogen or either $R^{4e}$ or $R^{4e'}$ taken together with $R^{4c}$ or $R^{4c'}$ forms a bond).

Yet another preferred embodiment is a compound where Y is —$C(R^{4d})(R^{4d'})$—, $R^{4b}$, $R^{4b'}$, $R^{4f}$, and $R^{4f'}$ are all hydrogen; and $R^{4d}$ and $R^{4d'}$ taken together form a partially or fully saturated 3- to 6-membered heterocyclic ring, a 5- to 6-membered lactone ring, or a 4- to 6-membered lactam ring, where the heterocyclic ring, the lactone ring and the lactam ring are optionally substituted and the lactone ring or the lactam ring optionally contains an additional heteroatom selected from oxygen, nitrogen or sulfur (preferably, $R^{4d}$ and $R^{4d'}$ taken together form a 5 to 6 membered lactam ring, where the lactam ring is optionally substituted and optionally contains an additional heteroatom selected from nitrogen or oxygen). In this embodiment, X is preferably a bond, —$CH_2CH_2$— or —$C(R^{4c})(R^{4c'})$—, where $R^{4c}$ and $R^{4c'}$ are each independently hydrogen or an optionally substituted $(C_1–C_6)$alkyl, or either $R^{4c}$ or $R^{4c'}$ taken together with $R^{4e}$ or $R^{4e'}$ forms a bond, a methylene bridge or an ethylene bridge (more preferably, X is a bond or —$C(R^{4c})(R^{4c'})$—, where $R^{4c}$ and $R^{4c'}$ are each hydrogen); and Z is preferably a bond, —$CH_2CH_2$— or —$C(R^{4e})(R^{4e'})$—, where $R^{4e}$ and $R^{4e'}$ are each independently hydrogen or an optionally substituted $(C_1–C_6)$alkyl, or either $R^{4e}$ or $R^{4e'}$ taken together with $R^{4c\ or\ R4c'}$ forms a bond, a methylene bridge or an ethylene bridge (more preferably, Z is a bond or —$C(R^{4e})(R^{4e'})$—, where $R^{4e}$ and $R^{4e'}$ are each hydrogen).

Another preferred compound of the present invention is a compound of Formula (I) where $R^4$ is a group of Formula (IB) where where $R^{4a}$ is as defined above, $R^{4b}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)alkyl)_2$N—C(O)—, $(C_1-C_6)$alkylamino-, $((C_1-C_4)alkyl)_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3- to 6-membered heterocycle, and a partially or fully saturated 3- to 8-membered carbocyclic ring, where the moiety is optionally substituted, $R^{4b'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $((C_1-C_4)alkyl)_2$N—C(O)—, aryl, heteroaryl, a partially or fully saturated 3- to 6-membered heterocycle, and a partially or fully saturated 3- to 8-membered carbocyclic ring, where the moiety is optionally substituted, or $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, $—CH_2CH_2—$ or $—C(R^{4c})(R^{4c'})—$, where $R^{4c}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)alkyl)_2$N—C(O)—, $(C_1-C_6)$alkylamino-, $((C_1-C_4)alkyl)_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3- to 6-membered heterocycle, and a partially or fully saturated 3- to 8-membered carbocyclic ring, where the moiety is optionally substituted, or $R^{4c}$ taken together with $R^{4e}$, $R^{4e'}$, $R^{4f}$, or $R^{4f'}$ forms a bond, a methylene bridge, or an ethylene bridge, and $R^{4c'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $((C_1-C_4)alkyl)_2$N—C(O)—, aryl, heteroaryl, a partially or fully saturated 3- to 6-membered heterocycle, and a partially or fully saturated 3- to 8-membered carbocyclic ring, where the moiety is optionally substituted, or $R^{4c'}$ taken together with $R^{4e}$, $R^{4e'}$, $R^{4f}$, or $R^{4f'}$ forms a bond, a methylene bridge, or an ethylene bridge (preferably, X is a bond, $—CH_2CH_2—$ or $—C(R^{4c})(R^{4c'})—$, where $R^{4c}$ and $R^{4c'}$ are each independently hydrogen or $(C_1-C_6)$alkyl);

Y is oxygen, sulfur, —C(O)—, or $—C(R^{4d})(R^{4d'})—$, where $R^{4d}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)alkyl)_2$N—C(O)—, $(C_1-C_6)$alkylamino-, $((C_1-C_4)alkyl)_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3- to 6-membered heterocycle, and a partially or fully saturated 3- to 8-membered carbocyclic ring, where the moiety is optionally substituted, and $R^{4d'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $((C_1-C_4)alkyl)_2$N—C(O)—, aryl, heteroaryl, a partially or fully saturated 3- to 6-membered heterocycle, and a partially or fully saturated 3- to 8-membered carbocyclic ring, where the moiety is optionally substituted, or $R^{4d}$ and $R^{4d'}$ taken together form a partially or fully saturated, 3- to 6-membered heterocyclic ring, a 5- or 6-membered lactone ring, or a 4- to 6-membered lactam ring, where the heterocyclic ring, the lactone ring and the lactam ring are optionally substituted and the lactone ring and the lactam ring optionally contain an additional heteroatom selected from oxygen, nitrogen or sulfur, or Y is $—NR^{4d''}—$, where $R^{4d''}$ is a hydrogen or a chemical moiety selected from the group consisting of $(C_1-C_6)$alkyl, $(C_3-C_6)$cycloalkyl, $(C_1-C_3)$alkylsulfonyl-, $(C_1-C_3)$alkylaminosulfonyl-, di$(C_1-C_3)$alkylaminosulfonyl-, acyl, $(C_1-C_6)$alkyl-O—C(O)—, aryl, and heteroaryl, where the moiety is optionally substituted (preferably, Y is $—NR^{4d''}—$, where $R^{4d''}$ is a hydrogen or a chemical moiety selected from the group consisting of $(C_1-C_6)$alkyl, $(C_3-C_6)$cycloalkyl, $(C_1-C_3)$alkylsulfonyl-, $(C_1-C_3)$alkylaminosulfonyl-, di$(C_1-C_3)$alkylaminosulfonyl-, acyl, $(C_1-C_6)$alkyl-O—C(O)—, aryl, and heteroaryl, where the moiety is optionally substituted);

Z is a bond, $—CH_2CH_2—$, or $—C(R^{4e})(R^{4e'})—$, where $R^{4e}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)alkyl)_2$N—C(O)—, $(C_1-C_6)$alkylamino-, $((C_1-C_4)alkyl)_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3- to 6-membered heterocycle, and a partially or fully saturated 3- to 8-membered carbocyclic ring, where the moiety is optionally substituted, or $R^{4e}$ taken together with $R^{4b}$, $R^{4b'}$, $R^{4c}$, or $R^{4c'}$ forms a bond, a methylene bridge, or an ethylene bridge, and $R^{4e'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $((C_1-C_4)alkyl)_2$N—C(O)—, aryl, heteroaryl, a partially or fully saturated 3- to 6-membered heterocycle, and a partially or fully saturated 3- to 8-membered carbocyclic ring, where the moiety is optionally substituted, or $R^{4e'}$ taken together with $R^{4b}$, $R^{4b'}$, $R^{4c}$, or $R^{4c'}$ forms a bond, a methylene bridge, or an ethylene bridge (preferably, Z is a bond, $—CH_2CH_2—$ or $—C(R^{4c})(R^{4c'})—$, where $R^{4c}$ and $R^{4c'}$ are each independently hydrogen or $(C_1-C_6)$alkyl);

$R^{4f}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)alkyl)_2$N—C(O)—, $(C_1-C_6)$alkylamino-, $((C_1-C_4)alkyl)_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3- to 6-membered heterocycle, and a partially or fully saturated 3- to 8-membered carbocyclic ring, where the moiety is optionally substituted; and $R^{4f'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $((C_1-C_4)alkyl)_2$N—C(O)—, aryl, heteroaryl, a partially or fully saturated 3- to 6-membered heterocycle, and a partially or fully saturated 3- to 8-membered carbocyclic ring, where the moiety is optionally substituted, or $R^{4f}$ or $R^{4f'}$ taken together with $R^{4b}$, $R^{4b'}$, $R^{4c}$, or $R^{4c'}$ forms a bond, a methylene bridge, or an ethylene bridge;

a pharmaceutically acceptable salt thereof, a prodrug of the compound or the salt, or a solvate or hydrate of the compound, the salt or the prodrug.

Yet another preferred compound of the present invention is a compound of Formula (I) where $R^4$ is a group of Formula (IC), where where $R^5$ and $R^6$ are each independently hydrogen or $(C_1-C_4)$alkyl, and $R^7$ is $(C_1-C_4)$alkyl-, halo-substituted $(C_1-C_4)$alkyl-, $(C_1-C_4)$alkoxy$(C_1-C_4)$alkyl-, $C_1-C_4)$alkylamino$(C_1-C_4)$alkyl,- di$(C_1-C_4)$alkylamino($C_1$–$C_4$)alkyl-, or a partially or fully saturated 4- to 6-membered heterocylic ring containing 1 to 2 heteroatoms independently selected from oxygen, sulfur or nitrogen, or $R^5$ and $R^6$ or $R^5$ and $R^7$ taken together form a 5- to 6-membered lactone, 4- to 6-membered lactam, or a partially or fully saturated 4- to 6-membered heterocycle containing 1 to 2 heteroatoms independently selected from oxygen, sulfur or nitrogen, where the lactone, the lactam and the heterocycle are optionally substituted; a pharmaceutically acceptable salt thereof, a prodrug of the compound or the salt, or a solvate or hydrate of the compound, the salt or the prodrug. Preferably, $R^5$ and $R^6$ are each independently hydrogen or ($C_1$–$C_4$)alkyl, and $R^7$ is ($C_1$–$C_4$)alkyl.

Preferred compounds of the present invention include: 1-[9-(4-chloro-phenyl)-8-(2-chlorophenyl)-9H-purin-6-yl]-3-ethylamino-azetidine-3-carboxylic acid amide; 1-[9-(4-chlorophenyl)-8-(2-chlorophenyl)-9H-purin-6-yl]-3-isopropylaminoazetideine-3carboxylic acid amide; 1-{1-[9-(4-chloro-phenyl)-8-(2-chlorophenyl)-9H-purin-6-yl]-4-phenylpiperidin-4-yl}-ethanone; {3-[9-(4-chlorophenyl)-8-(2,4-dichlorophenyl)-9H-purin-6-yl]-3-(1α,5α,6α)-azabicyclo[3.1.0]hex-6-yl}-dimethylamine; 6-(1-benzylpyrrolidin-3-yloxy)-9-(4-chlorophenyl)-8-(2,4-dichlorophenyl)-9H-purine; 9-(4-chlorophenyl)-6-(1cyclohexylazetidin-3-yloxy)-8-(2,4-dichlorophenyl)-9H-purine; 6-tert-butoxy-9-(4-chlorophenyl)-8-(2,4-dichlorophenyl)-9H-purine; 9-(4-chlorophenyl)-8-(2,4-dichlorophenyl)-6-isopropoxy-9H-purine; 1-[9-(4-chlorophenyl)-8-(2,4-dichlorophenyl)-9H-purin-6-yl]-4-propylaminopiperidine-4-carboxylic acid amide; 1-[9-(4-chlorophenyl)-8-(2-fluorophenyl)-9H-purin-6-yl]-4propylaminopiperidine-4-carboxylic acid amide; 1-[9-(4-chlorophenyl)-8-(2chlorophenyl)-9H-purin-6-yl]-4-propylaminopiperidine-4-carboxylic acid amide; 1-[9-(4-chlorophenyl)-8-(2-fluorophenyl)-2-methyl-]H-purin-6-yl]-4-isopropylaminopiperidine-4-carboxylic acid amide; 1-[9-(4-chlorophenyl)-8-(2-chlorophenyl)-9H-purin-6-yl]-4-pyrrolidin-1-yl-piperidine-4-carboxylic acid amide; 1-[9-(4-chlorophenyl)-8-(2-chlorophenyl)-9H-purin-6-yl]-4-ethylamino-piperidine-4-carboxylic acid amide; 1-[9-(4-chlorophenyl)-8-(2-chlorophenyl)-9H-purin-6-yl]-4-isopropylaminopiperidine-4-carboxylic acid amide; 4-amino-1-[9-(4-chlorophenyl)-8-(2-chlorophenyl)-9H-purin-6-yl]-piperidine-4-carboxylic acid amide; 1-[9-(4-chlorophenyl)-8-(2,4-dichlorophenyl)-9H-purin-6-yl]-4-methylaminopiperidine-4-carboxylic acid amide; 1-[9-(4-chlorophenyl)-8-(2-fluorophenyl)-9H-purin-6-yl]-4-isopropylaminopiperidine-4-carboxylic acid amide; 8-[9-(4-chlorophenyl)-8-(2-chlorophenyl)-9H-purin-6-yl]-1-isopropyl-1,3,8-triazaspiro[4.5]decan-4-one; 9-[9-(4-chlorophenyl)-8-(2-chlorophenyl)-9H-purin-6-yl]-1-methyl-4-oxa-1,9-diazaspiro[5.5]undecan-2-one; 8-[9-(4-chlorophenyl)-8-(2,4-dichlorophenyl)-9H-purin-6-yl]-1-isopropyl-1,3,8-triazaspiro[4.5]decan-4-one; 1-[9-(4-chlorophenyl)-8-(2-chlorophenyl)-9H-purin-6-yl]-4-(4-fluorophenyl)-piperidin-4-ol; 1-[9-(4-chlorophenyl)-8-(2-chlorophenyl)-9H-purin-6-yl]-4-phenylpiperidin-4-ol; 4-benzyl-1-[9-(4-chloro-phenyl)-8-(2-chlorophenyl)-9H-purin-6-yl]-piperidin-4-ol; 4-[9-(4-chloro-phenyl)-8-(2-chlorophenyl)-9H-purin-6-yl]-piperazine-2-carboxylic acid methylamide; 9-(4-chlorophenyl)-8-(2,4-dichlorophenyl)-6-(4-pyridin-2-yl-piperazin-1-yl)-9H-purine; and 9-(4-chlorophenyl)-8-(2,4-dichlorophenyl)-6-(4-pyrimidin-2-yl-piperazin-1-yl)-9H-purine; a pharmaceutically acceptable salt thereof, or a solvate or hydrate of the compound or the salt. More preferred compounds include 4-amino-[9-(4-chlorophenyl)-8-(2-chlorophenyl)-9H-purin-6-yl]-piperidine-4-carboxylic acid amide; and 1-[9-(4-chlorophenyl)-8-(2-chlorophenyl)-9H-purin-6-yl]-4-ethylaminopiperidine-4-carboxylic acid amide (including the pharmaceutically acceptable salts thereof (preferably the mesylate, besylate or hydrochloride salt) or a solvate or hydrate of the compound per se or the salt).

Another embodiment of the present invention includes intermediates (1c/d) and (1b) which are useful in the synthesis of the compounds of the present invention:

(1c/d)

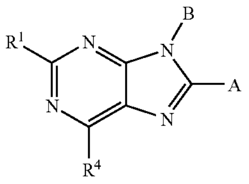

wherein A and B are each independently a phenyl substituted with 1 to 3 substituents independently selected from the group consisting of halo, ($C_1$–$C_4$)alkoxy, ($C_1$–$C_4$)alkyl, halo-substituted ($C_1$–$C_4$)alkyl, and cyano; $R^1$ is hydrogen, ($C_1$–$C_4$)alkyl, halo-substituted ($C_1$–$C_4$)alkyl, or ($C_1$–$C_4$) alkoxy; and $R^4$ is hydroxy or halo; and (1b)

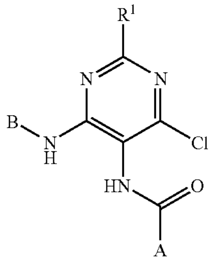

wherein A and B are each independently a phenyl substituted with 1 to 3 substituents independently selected from the group consisting of halo, ($C_1$–$C_4$)alkoxy, ($C_1$–$C_4$)alkyl, halo-substituted ($C_1$–$C_4$)alkyl, and cyano; and $R^1$ is hydrogen, ($C_1$–$C_4$)alkyl, halo-substituted ($C_1$–$C_4$)alkyl, or ($C_1$–$C_4$)alkoxy.

Preferably, A and B are each independently a phenyl substituted with 1 to 2 substituents independently selected from the group consisting of chloro, fluoro, ($C_1$–$C_4$)alkoxy, ($C_1$–$C_4$)alkyl, fluoro-substituted ($C_1$–$C_4$)alkyl), and cyano. More preferably, A is 2chlorophenyl, 2-fluorophenyl, 2,4-dichlorophenyl, 2-fluoro-4-chlorophenyl, 2-chloro-4-fluorophenyl, or 2,4-difluorophenyl; and B is 4-chlorophenyl or 4-fluorophenyl.

Yet another embodiment of the present invention includes a pharmaceutical composition comprising (1) a compound of the present invention and (2) a pharmaceutically acceptable excipient, diluent, or carrier. Preferably, the composition comprises a therapeutically effective amount of a compound of the present invention. The composition may also contain at least one additional pharmaceutical agent (described herein). Preferred agents include nicotine receptor partial agonists, opioid antagonists (e.g., naltrexone and nalmefene), dopaminergic agents (e.g., apomorphine), attention deficit disorder (ADD/ADHD) agents (e.g., Ritalin™, Strattera™, Concerta™ and Adderall™), and anti-obesity agents (described herein below).

Yet another embodiment of the present invention includes a method for treating a disease, condition or disorder modulated by a cannabinoid receptor (in particular, a CB1 receptor) antagonist in animals comprising the step of administering to an animal in need of such treatment a therapeutically effective amount of a compound of Formula (II) (or a pharmaceutical composition thereof).

(II)

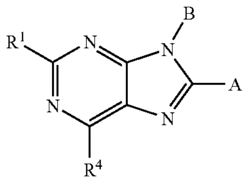

wherein

A is an optionally substituted aryl or an optionally substituted heteroaryl; B is an optionally substituted aryl or an optionally substituted heteroaryl; $R^1$ is hydrogen, $(C_1–C_4)$alkyl, halo-substituted $(C_1–C_4)$alkyl, or $(C_1–C_4)$alkoxy;

$R^4$ is (i) a group having Formula (IA) or Formula (IB)

(IA)

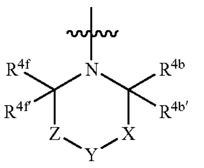

(IB)

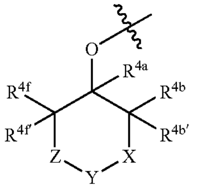

where $R^{4a}$ is hydrogen or $(C_1–C_3)$alkyl;

$R^{4b}$ and $R^{4b'}$ are each independently hydrogen, cyano, hydroxy, amino, $H_2NC(O)$—, or a chemical moiety selected from the group consisting of $(C_1–C_6)$alkyl, $(C_1–C_6)$alkoxy, acyloxy, acyl, $(C_1–C_3)$alkyl-O—C(O)—, $(C_1–C_4)$alkyl-NH—C(O)—, $(C_1–C_4)$alkyl)$_2$N—C(O)—, $(C_1–C_6)$alkylamino-, $((C_1–C_4)$alkyl)$_2$amino-, $(C_3–C_6)$cycloalkylamino-, acylamino-, aryl$(C_1–C_4)$alkylamino-, heteroaryl$(C_1–C_4)$alkylamino-, aryl, heteroaryl, a partially or fully saturated 3- to 6-membered heterocycle, and a partially or fully saturated 3- to 8-membered carbocyclic ring, where the moiety is optionally substituted, or either $R^{4b}$ or $R^{4b'}$ taken together with $R^{4e}$, $R^{4e'}$, $R^{4f}$, or $R^{4f'}$ forms a bond, a methylene bridge, or an ethylene bridge;

X is a bond, —$CH_2CH_2$— or —$C(R^{4c})(R^{4c'})$—, where $R^{4c}$ and $R^{4c'}$ are each independently hydrogen, cyano, hydroxy, amino, $H_2NC(O)$—, or a chemical moiety selected from the group consisting of $(C_1–C_6)$alkyl, $(C_1–C_6)$alkoxy, acyloxy, acyl, $(C_1–C_3)$alkyl-O—C(O)—, $(C_1–C_4)$alkyl-NH—C(O)—, $((C_1–C_4)$alkyl)$_2$N—C(O)—, $(C_1–C_6)$alkylamino-, di$(C_1–C_4)$alkylamino-, $(C_3–C_6)$cycloalkylamino-, acylamino-, aryl$(C_1–C_4)$alkylamino-, heteroaryl$(C_1–C_4)$alkylamino-, aryl, heteroaryl, a partially or fully saturated 3- to 6-membered heterocycle, and a partially or fully saturated 3- to 8-membered carbocyclic ring, where the moiety is optionally substituted, or either $R^{4c}$ or $R^{4c'}$ taken together with $R^{4e}$, $R^{4e'}$, $R^{4f}$, or $R^{4f'}$ forms a bond, a methylene bridge or an ethylene bridge;

Y is oxygen, sulfur, —C(O)—, or —$C(R^{4d})(R^{4d'})$—, where $R^{4d}$ and $R^{4d'}$ are each independently hydrogen, cyano, hydroxy, amino, $H_2NC(O)$—, or a chemical moiety selected from the group consisting of $(C_1–C_6)$alkyl, $(C_1–C_6)$alkoxy, acyloxy, acyl, $(C_1–C_3)$alkyl-O—C(O)—, $(C_1–C_4)$alkyl-NH—C(O)—, $((C_1–C_4)$alkyl)$_2$N—C(O)—, $(C_1–C_6)$alkylamino-, di$(C_1–C_4)$alkylamino-, $(C_3–C_6)$cycloalkylamino-, acylamino-, aryl$(C_1–C_4)$alkylamino-, heteroaryl$(C_1–C_4)$alkylamino-, aryl, heteroaryl, a partially or fully saturated 3- to 6-membered heterocycle, and a partially or fully saturated 3- to 8-membered carbocyclic ring, where the moiety is optionally substituted, or $R^{4d}$ and $R^{4d'}$ taken together form a partially or fully saturated, 3- to 6-membered heterocyclic ring, a 5- or 6-membered lactone ring, or a 4- to 6-membered lactam ring, where the heterocyclic ring, the lactone ring and the lactam ring are optionally substituted and the lactone ring and the lactam ring optionally contain an additional heteroatom selected from oxygen, nitrogen or sulfur, or Y is —$NR^{4d''}$—, where $R^{4d''}$ is a hydrogen or a chemical moiety selected from the group consisting of $(C_1–C_6)$alkyl, $(C_3–C_6)$cycloalkyl, $(C_1–C_3)$alkylsulfonyl-, $(C_1–C_3)$alkylaminosulfonyl-, di$(C_1–C_3)$alkylaminosulfonyl-, acyl, $(C_1–C_6)$alkyl-O—C(O)—, aryl, and heteroaryl, where the moiety is optionally substituted;

Z is a bond, —$CH_2CH_2$—, or —$C(R^{4e})(R^{4e'})$—, where $R^{4e}$ and $R^{4e'}$ are each independently hydrogen, cyano, hydroxy, amino, $H_2NC(O)$—, or a chemical moiety selected from the group consisting of $(C_1–C_6)$alkyl, $(C_1–C_6)$alkoxy, acyloxy, acyl, $(C_1–C_3)$alkyl-O—C(O)—, $(C_1–C_4)$alkyl-NH—C(O)—, $((C_1–C_4)$alkyl)$_2$N—C(O)—, $(C_1–C_6)$alkylamino-, di$(C_1–C_4)$alkylamino-, $(C_3–C_6)$cycloalkylamino-, acylamino-, aryl$(C_1–C_4)$alkylamino-, heteroaryl$(C_1–C_4)$alkylamino-, aryl, heteroaryl, a partially or fully saturated 3- to 6-membered heterocycle, and a partially or fully saturated 3- to 8-membered carbocyclic ring, where the moiety is optionally substituted, or either $R^{4e}$ or $R^{4e'}$ taken together with $R^{4b}$, $R^{4b'}$, $R^{4c}$, or $R^{4c'}$ forms a bond, a methylene bridge or an ethylene bridge; and $R^{4f}$ and $R^{4f'}$ are each independently hydrogen, cyano, hydroxy, amino, $H_2NC(O)$—, or a chemical moiety selected from the group consisting of $(C_1–C_6)$alkyl, $(C_1–C_6)$alkoxy, acyloxy, acyl, $(C_1–C_3)$alkyl-O—C(O)—, $(C_1–C_4)$alkyl-NH—C(O)—, $((C_1–C_4)$alkyl)$_2$N—C(O)—, $(C_1–C_6)$alkylamino-, di$(C_1–C_4)$alkylamino-, $(C_3–C_6)$cycloalkylamino-, acylamino-, aryl$(C_1–C_4)$alkylamino-, heteroaryl$(C_1–C_4)$alkylamino-, aryl, heteroaryl, a partially or fully saturated 3- to 6-membered heterocycle, and a partially or fully saturated 3- to 8-membered carbocyclic ring, where the moiety is optionally substituted, or either $R^{4f}$ or $R^{4f'}$ taken together with $R^{4b}$, $R^{4b'}$, $R^{4c}$, or $R^{4c'}$ forms a bond, a methylene bridge or an ethylene bridge; or (ii) a group having Formula (IC)

(IC)

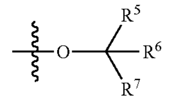

where $R^5$ and $R^6$ are each independently hydrogen or $(C_1-C_4)$alkyl, and $R^7$ is $(C_1-C_4)$alkyl-, halo-substituted $(C_1-C_4)$alkyl-, $(C_1-C_4)$alkoxy$(C_1-C_4)$alkyl-, $(C_1-C_4)$alkylamino$(C_1-C_4)$alkyl-, di$(C_1-C_4)$alkylamino$(C_1-C_4)$alkyl-, or a partially or fully saturated 4- to 6-membered heterocylic ring containing 1 or 2 heteroatoms independently independently selected from oxygen, sulfur or nitrogen, or $R^5$ and $R^6$ or $R^5$ and $R^7$ taken together form a 5- or 6-membered lactone, 4- to 6-membered lactam, or a partially or fully saturated 4- to 6-membered heterocycle containing 1 or 2 heteroatoms independently selected from oxygen, sulfur or nitrogen, where the lactone, the lactam and the heterocycle are optionally substituted;

(iii) an amino group substituted with one or more substituents independently selected from the group consisting of $(C_1-C_8)$alkyl, aryl$(C_1-C_4)$alkyl, a partially or fully saturated $(C_3-C_8)$cycloalkyl, hydroxy$(C_1-C_6)$alkyl, $(C_1-C_3)$alkoxy $(C_1-C_6)$alkyl, heteroaryl$(C_1-C_3)$alkyl, and a fully or partially saturated heterocycle; or (iv) an $(C_1-C_6)$alkyl group substituted with one or more substituents independently selected from the group consisting of hydroxy, $(C_1-C_6)$alkoxy, amino, $(C_1-C_6)$alkylamino, di($(C_1-C_6)$alkyl)amino $(C_1-C_3)$alkylsulfonyl, $(C_1-C_3)$ alkylsulfamyl, di($(C_1-C_3)$alkyl)sulfamyl, acyloxy, a fully or partially saturated heterocycle, and a fully or partially saturated cycloalkyl;

a pharmaceutically acceptable salt thereof, a prodrug of the compound or the salt, or a solvate or hydrate of the compound, the salt or the prodrug.

Diseases, conditions, and/or disorders modulated by cannabinoid receptor antagonists include eating disorders (e.g., binge eating disorder, anorexia, and bulimia), weight loss or control (e.g., reduction in calorie or food intake, and/or appetite suppression), obesity, depression, atypical depression, bipolar disorders, psychoses, schizophrenia, behavioral addictions, suppression of reward-related behaviors (e.g., conditioned place avoidance, such as suppression of cocaine- and morphine-induced conditioned place preference), substance abuse, addictive disorders, impulsivity, alcoholism (e.g., alcohol abuse, addiction and/or dependence including treatment for abstinence, craving reduction and relapse prevention of alcohol intake), tobacco abuse (e.g., smoking addiction, cessation and/or dependence including treatment for craving reduction and relapse prevention of tobacco smoking), dementia (including memory loss, Alzheimer's disease, dementia of aging, vascular dementia, mild cognitive impairment, age-related cognitive decline, and mild neurocognitive disorder), sexual dysfunction in males (e.g., erectile difficulty), seizure disorders, epilepsy, gastrointestinal disorders (e.g., dysfunction of gastrointestinal motility or intestinal propulsion), attention deficit disorders (ADD) or attention deficit hyperactivity disorders (ADHD), Parkinson's disease, and type II diabetes. In a preferred embodiment, the method is used in the treatment of obesity, bulimia, ADHD, alcoholism, and/or tobacco abuse.

Compounds of the present invention may be administered in combination with other pharmaceutical agents. Preferred pharmaceutical agents include nicotine receptor partial agonists, opioid antagonists (e.g., naltrexone (including naltrexone depot), antabuse, and nalmefene), dopaminergic agents (e.g., apomorphine), ADHD agents (e.g., methylphenidate hydrochloride (e.g., Ritalin™ and Concerta™), atomoxetine (e.g., Strattera™), and amphetamines (e.g., Adderall™)) and anti-obesity agents, such as apo-B/MTP inhibitors, 11β-hydroxy steroid dehydrogenase-1 (11β-HSD type 1) inhibitors, peptide $YY_{3-36}$ and analogs thereof, MCR-4 agonists, CCK-A agonists, monoamine reuptake inhibitors, sympathomimetic agents, $\beta_3$ adrenergic receptor agonists, dopamine receptor agonists, melanocyte-stimulating hormone receptor analogs, 5-HT2c receptor agonists, melanin concentrating hormone receptor antagonists, leptin, leptin analogs, leptin receptor agonists, galanin receptor antagonists, lipase inhibitors, bombesin receptor agonists, neuropeptide-Y receptor antagonists, thyromimetic agents, dehydroepiandrosterone or analogs thereof, glucocorticoid receptor antagonists, orexin receptor antagonists, glucagon-like peptide-1 receptor agonists, ciliary neurotrophic factors, human agouti-related protein antagonists, ghrelin receptor antagonists, histamine 3 receptor antagonists or inverse agonists, and neuromedin U receptor agonists, and the like.

The combination therapy may be administered as (a) a single pharmaceutical composition which comprises a compound of the present invention, at least one additional pharmaceutical agent described herein and a pharmaceutically acceptable excipient, diluent, or carrier; or (b) two separate pharmaceutical compositions comprising (i) a first composition comprising a compound of the present invention and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions may be administered simultaneously or sequentially and in any order.

Yet another aspect of the present invention includes a pharmaceutical kit for use by a consumer to treat diseases, conditions or disorders modulated by cannabinoid receptor antagonists in an animal. The kit comprises a) a suitable dosage form comprising a compound of the present invention; and b) instructions describing a method of using the dosage form to treat diseases, conditions or disorders that are modulated by cannabinoid receptor (in particular, the CB1 receptor) antagonists.

Another embodiment includes a pharmaceutical kit comprising: a) a first dosage form comprising (i) a compound of the present invention and (ii) a pharmaceutically acceptable carrier, excipient or diluent; b) a second dosage form comprising (i) an additional pharmaceutical agent described herein, and (ii) a pharmaceutically acceptable carrier, excipient or diluent; and c) a container.

DEFINITIONS

As used herein, the term "alkyl" refers to a hydrocarbon radical of the general formula $C_nH_{2n+1}$. The alkane radical may be straight or branched. For example, the term "$(C_1-C_6)$alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). Similarly, the alkyl portion (i.e., alkyl moiety) of an alkoxy, acyl (e.g., alkanoyl), alkylamino, dialkylamino, and alkylthio group have the same definition as above. When indicated as being "optionally substituted", the alkane radical or alkyl moiety may be unsubstituted or substituted with one or more substituents (generally, one to three substituents except in the case of halogen substituents such as perchloro or perfluoroalkyls) independently selected from the group of substituents listed below in the definition for "substituted." "Halo-substituted alkyl" refers to an alkyl group substituted with one or more halogen atoms (e.g., fluoromethyl, difluoromethyl, trifluoromethyl, perfluoroethyl, and the like). When substituted, the alkane radicals or alkyl moieties are preferably substituted with 1 to 3 fluoro substituents, or 1 or 2 substituents independently selected from $(C_1–C_3)$alkyl, $(C_3–C_6)$cycloalkyl, $(C_2–C_3)$alkenyl, aryl, heteroaryl, 3- to 6-membered heterocycle, chloro, cyano, hydroxy, $(C_1–C_3)$ alkoxy, aryloxy, amino, $(C_1–C_6)$alkyl amino, di-$(C_1–C_4)$ alkyl amino, aminocarboxylate (i.e., $(C_1–C_3)$alkyl-O—C (O)—NH—), hydroxy$(C_2–C_3)$alkylamino, or keto (oxo), and more preferably, 1 to 3 fluoro groups, or 1 substituent selected from $(C_1–C_3)$alkyl, $(C_3–C_6)$cycloalkyl, $(C_6)$aryl, 6-membered-heteroaryl, 3- to 6-membered heterocycle, $(C_1–C_3)$alkoxy, $(C_1–C_4)$alkyl amino or di-$(C_1–C_2)$alkyl amino.

The terms "partially or fully saturated carbocyclic ring" (also referred to as "partially or fully saturated cycloalkyl") refers to nonaromatic rings that are either partially or fully hydrogenated and may exist as a single ring, bicyclic ring or a spiral ring. Unless specified otherwise, the carbocyclic ring is generally a 3- to 8-membered ring (preferably, 3- to 6-membered ring). For example, partially or fully saturated carbocyclic rings (or cycloalkyl) include groups such as cyclopropyl, cyclopropenyl, cyclobutyl, cyclobutenyl, cyclopentyl, cyclpentenyl, cyclopentadienyl, cyclohexyl, cyclohexenyl, cyclohexadienyl, norbornyl (bicyclo[2.2.1] heptyl), norbornenyl, bicyclo[2.2.2]octyl, and the like. When designated as being "optionally substituted", the partially saturated or fully saturated cycloalkyl group may be unsubstituted or substituted with one or more substituents (typically, one to three substituents) independently selected from the group of substituents listed below in the definition for "substituted." A substituted carbocyclic ring also includes groups wherein the carbocyclic ring is fused to a phenyl ring (e.g., indanyl). The carbocyclic group may be attached to the chemical entity or moiety by any one of the carbon atoms within the carbocyclic ring system. When substituted, the carbocyclic group is preferably substituted with 1 or 2 substituents independently selected from $(C_1–C_3)$alkyl, $(C_2–C_3)$alkenyl, $(C_1–C_6)$alkylidenyl, aryl, heteroaryl, 3- to 6-membered heterocycle, chloro, fluoro, cyano, hydroxy, $(C_1–C_3)$alkoxy, aryloxy, amino, $(C_1–C_6)$ alkyl amino, di-$(C_1–C_4)$alkyl amino, aminocarboxylate (i.e., $(C_1–C_3)$alkyl-O—C(O)—NH—), hydroxy$(C_2–C_3)$alkylamino, or keto (oxo), and more preferably 1 or 2 from substituents independently selected from $(C_1–C_2)$alkyl, 3- to 6-membered heterocycle, fluoro, $(C_1–C_3)$alkoxy, $(C_1–C_4)$ alkyl amino or di-$(C_1–C_2)$alkyl amino. Similarly, any cycloalkyl portion of a group (e.g., cycloalkylalkyl, cycloalkylamino, etc.) has the same definition as above.

The term "partially saturated or fully saturated heterocyclic ring" (also referred to as "partially saturated or fully saturated heterocycle") refers to nonaromatic rings that are either partially or fully hydrogenated and may exist as a single ring, bicyclic ring or a spiral ring. Unless specified otherwise, the heterocyclic ring is generally a 3- to 6-membered ring containing 1 to 3 heteroatoms (preferably 1 or 2 heteroatoms) independently independently selected from sulfur, oxygen or nitrogen. Partially saturated or fully saturated heterocyclic rings include groups such as epoxy, aziridinyl, tetrahydrofuranyl, dihydrofuranyl, dihydropyridinyl, pyrrolidinyl, N-methylpyrrolidinyl, imidazolidinyl, imidazolinyl, piperidinyl, piperazinyl, pyrazolidinyl, 2H-pyranyl, 4H-pyranyl, 2H-chromenyl, oxazinyl, morpholino, thiomorpholino, tetrahydrothienyl, tetrahydrothienyl 1,1-dioxide, and the like. When indicated as being "optionally substituted", the partially saturated or fully saturated heterocycle group may be unsubstiuted or substituted with one or more substituents (typically, one to three substituents) independently selected from the group of substituents listed below in the definition for "substituted." A substituted heterocyclic ring includes groups wherein the heterocyclic ring is fused to an aryl or heteroaryl ring (e.g., 2,3-dihydrobenzofuranyl, 2,3-dihydroindolyl, 2,3-dihydrobenzothiophenyl, 2,3-dihydrobenzothiazolyl, etc.). When substituted, the heterocycle group is preferably substituted with 1 or 2 substituents independently selected from $(C_1–C_3)$alkyl, $(C_3–C_6)$cycloalkyl, $(C_2–C_4)$alkenyl, aryl, heteroaryl, 3- to 6-membered heterocycle, chloro, fluoro, cyano, hydroxy, $(C_1–C_3)$alkoxy, aryloxy, amino, $(C_1–C_6)$ alkyl amino, di-$(C_1–C_3)$alkyl amino, aminocarboxylate (i.e., $(C_1–C_3)$alkyl-O—C(O)—NH—), or keto (oxo), and more preferably with 1 or 2 substituents independently selected from $(C_1–C_3)$alkyl, $(C_3–C_6)$cycloalkyl, $(C_6)$aryl, 6-membered-heteroaryl, 3- to 6-membered heterocycle, or fluoro. The heterocyclic group may be attached to the chemical entity or moiety by any one of the ring atoms within the heterocyclic ring system. Similarly, any heterocycle portion of a group (e.g., heterocycle-substituted alkyl, heterocycle carbonyl, etc.) has the same definition as above.

The term "aryl" or "aromatic carbocyclic ring" refers to aromatic moieties having a single (e.g., phenyl) or a fused ring system (e.g., naphthalene, anthracene, phenanthrene, etc.). A typical aryl group is a 6- to 10-membered aromatic carbocyclic ring(s). When indicated as being "optionally substituted", the aryl groups may be unsubstituted or substituted with one or more substituents (preferably no more than three substituents) independently selected from the group of substituents listed below in the definition for "substituted." Substituted aryl groups include a chain of aromatic moieties (e.g., biphenyl, terphenyl, phenylnaphthalyl, etc.). When substituted, the aromatic moieties are preferably substituted with 1 or 2 substituents independently selected from $(C_1–C_4)$alkyl, $(C_2–C_3)$alkenyl, aryl, heteroaryl, 3- to 6-membered heterocycle, bromo, chloro, fluoro, iodo, cyano, hydroxy, $(C_1–C_4)$alkoxy, aryloxy, amino, $(C_1–C_6)$alkyl amino, di-$(C_1–C_3)$alkyl amino, or aminocarboxylate (i.e., $(C_1–C_3)$alkyl-O—C(O)—NH—), and more preferably, 1 or 2 substituents independently selected from $(C_1–C_4)$alkyl, chloro, fluoro, cyano, hydroxy, or $(C_1–C_4)$alkoxy. The aryl group may be attached to the chemical entity or moiety by any one of the carbon atoms within the aromatic ring system. Similarly, the aryl portion (i.e., aromatic moiety) of an aroyl or aroyloxy (i.e., (aryl)-C(O)—O—) has the same definition as above.

The term "heteroaryl" or "heteroaromatic ring" refers to aromatic moieties containing at least one heteratom (e.g., oxygen, sulfur, nitrogen or combinations thereof) within a 5- to 10-membered aromatic ring system (e.g., pyrrolyl, pyridyl, pyrazolyl, indolyl, indazolyl, thienyl, furanyl, benzofuranyl, oxazolyl, imidazolyl, tetrazolyl, triazinyl, pyrimidyl, pyrazinyl, thiazolyl, purinyl, benzimidazolyl, quinolinyl, isoquinolinyl, benzothiophenyl, benzoxazolyl, etc.). The heteroaromatic moiety may consist of a single or fused ring system. A typical single heteroaryl ring is a 5- to 6-membered ring containing one to three heteroatoms independently selected from oxygen, sulfur and nitrogen and a typical fused heteroaryl ring system is a 9- to 10-membered ring system containing one to four heteroatoms independently selected from oxygen, sulfur and nitrogen. When indicated as being "optionally substituted", the heteroaryl groups may be unsubstituted or substituted with one or more substituents (preferably no more than three substituents) independently selected from the group of substituents listed below in the definition for "substituted." When substituted, the heteroaromatic moieties are preferably substituted with 1 or 2 substituents independently selected from $(C_1–C_4)$ alkyl, $(C_2–C_3)$alkenyl, aryl, heteroaryl, 3- to 6-membered heterocycle, bromo, chloro, fluoro, iodo, cyano, hydroxy, $(C_1–C_4)$alkoxy, aryloxy, amino, $(C_1–C_6)$alkyl amino, di-$(C_1–C_3)$alkyl amino, or aminocarboxylate (i.e., $(C_1–C_3)$ alkyl-O—C(O)—NH—), and more preferably, 1 or 2 substituents independently selected from $(C_1–C_4)$alkyl, chloro, fluoro, cyano, hydroxy, $(C_1–C_4)$alkoxy, $(C_1–C_4)$alkyl amino or di-$(C_1–C_2)$alkyl amino. The heteroaryl group may be attached to the chemical entity or moiety by any one of the atoms within the aromatic ring system (e.g., imidazol-1-yl, imidazol-2-yl, imidazol-4-yl, imidazol-5-yl, pyrid-2-yl, pyrid-3-yl, pyrid-4-yl, pyrid-5-yl, or pyrid-6-yl). Similarly, the heteroaryl portion (i.e., heteroaromatic moiety) of a heteroaroyl or heteroaroyloxy (i.e., (heteroaryl)-C(O)—O—) has the same definition as above.

The term "acyl" refers to alkyl, partially saturated or fully saturated cycloalkyl, partially saturated or fully saturated heterocycle, aryl, and heteroaryl substituted carbonyl groups. For example, acyl includes groups such as $(C_1–C_6)$ alkanoyl (e.g., formyl, acetyl, propionyl, butyryl, valeryl, caproyl, t-butylacetyl, etc.), $(C_3–C_6)$cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions above. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "substituted" specifically envisions and allows for one or more substitutions that are common in the art. However, it is generally understood by those skilled in the art that the substituents should be selected so as to not adversely affect the pharmacological characteristics of the compound or adversely interfere with the use of the medicament. Suitable substituents for any of the groups defined above include $(C_1–C_6)$alkyl, $(C_3–C_7)$cycloalkyl, $(C_2–C_6)$ alkenyl, $(C_1–C_6)$alkylidenyl, aryl, heteroaryl, 3- to 6-membered heterocycle, halo (e.g., chloro, bromo, iodo and fluoro), cyano, hydroxy, $(C_1–C_6)$alkoxy, aryloxy, sulfhydryl (mercapto), $(C_1–C_6)$alkylthio, arylthio, amino, mono- or di-$(C_1–C_6)$alkyl amino, quaternary ammonium salts, amino $(C_1–C_6)$alkoxy, aminocarboxylate (i.e., $(C_1–C_6)$alkyl-O—C(O)—NH—), hydroxy$(C_2–C_6)$alkylamino, amino$(C_1–C_6)$alkylthio, cyanoamino, nitro, $(C_1–C_6)$carbamyl, keto (oxo), acyl, $(C_1–C_6)$alkyl-$CO_2$—, glycolyl, glycyl, hydrazino, guanyl, sulfamyl, sulfonyl, sulfinyl, thio$(C_1–C_6)$alkyl-C(O)—, thio$(C_1–C_6)$alkyl-$CO_2$—, and combinations thereof. In the case of substituted combinations, such as "substituted aryl $(C_1–C_6)$alkyl", either the aryl or the alkyl group may be substituted, or both the aryl and the alkyl groups may be substituted with one or more substituents (typically, one to three substituents except in the case of perhalo substitutions). An aryl or heteroaryl substituted carbocyclic or heterocyclic group may be a fused ring (e.g., indanyl, dihydrobenzofuranyl, dihydroindolyl, etc.).

The term "halo" refers to a chloro, bromo, fluoro or iodo group.

The term "solvate" refers to a molecular complex of a compound represented by Formula (I) or (II) (including prodrugs and pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The phrase "pharmaceutically acceptable" indicates that the substance or composition must be compatible chemically and/or toxicologically, with the other ingredients comprising a formulation, and/or the mammal being treated therewith.

The term "protecting group" or "Pg" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, *Protective Groups in Organic Synthesis*, John Wiley & Sons, New York, 1991.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans (male or female), companion animals (e.g., dogs, cats and horses), food-source animals, zoo animals, marine animals, birds and other similar animal species. "Edible animals" refers to food-source animals such as cows, pigs, sheep and poultry. A preferred animal is a human.

The terms "treating", "treat", or "treatment" embrace both preventative, i.e., prophylactic, and palliative treatment.

The terms "modulated by a cannabinoid receptor" or "modulation of a cannabinoid receptor" refers to the activation or deactivation of a cannabinoid receptor. For example, a ligand may act as an agonist, partial agonist, inverse agonist, antagonist, or partial antagonist.

The term "antagonist" includes both full antagonists and partial antagonists, as well as inverse agonists.

The term "CB-1 receptor" refers to the G-protein coupled type 1 cannabinoid receptor.

The term "compounds of the present invention" (unless specifically identified otherwise) refer to compounds of Formula (I) and Formula (II), prodrugs thereof, pharmaceutically acceptable salts of the compounds, and/or prodrugs, and hydrates or solvates of the compounds, salts, and/or prodrugs, as well as, all stereoisomers (including diastereoisomers and enantiomers), tautomers and isotopically labeled compounds. Unless specified otherwise, the term "compounds of the present invention" does not include intermediates (1c/d) or (1b).

DETAILED DESCRIPTION

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1–19, Wiley, New York (1967–1999 ed.), or *Beilsteins Handbuch der organischen Chemie,* 4, Aufl. ed. Springer-Verlag, Berlin, including supplements (also available via the *Beilstein* online database)).

For illustrative purposes, the reaction schemes depicted below demonstrate potential routes for synthesizing the compounds of the present invention including key intermediates. For a more detailed description of the individual reaction steps, see the Examples section below. Those skilled in the art will appreciate that other synthetic routes may be used to synthesize the compounds of the present invention (including the inventive intermediates). Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, *Protective Groups in Organic Synthesis*, John Wiley & Sons, New York, 1991.

Compounds of Formula (I) and (II) can be prepared using the general procedures described by R. J. Chorvat, et al. in *J. Med. Chem,* 42, 833–848 (1999) and depicted in Scheme I below.

Scheme I

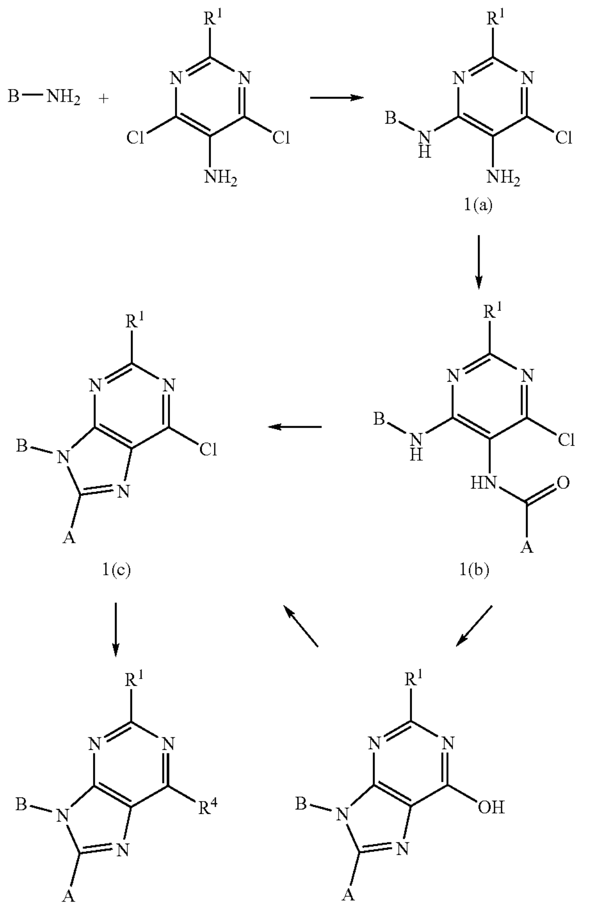

1(a)

1(c)

1(b)

(I) or (II)

1(d)

Intermediate 1(a) may be prepared by reacting the desired amino compound (B—$NH_2$, where B is as defined above) with 4,6-dichloro-5-aminopyrimidine (available from Sigma-Aldrich, St. Louis, Mo.) in refluxing aqueous hydrochloric acid (A. Miyashita et al. in *Chem. Pharm. Bull.,* 46, 390–399 (1998)) or ethoxyethanol at elevated temperatures. Suitable amino compounds (B—$NH_2$) include those compounds where B is aryl (e.g., aniline) or substituted aryl (e.g., 2-chloroaniline, 2-fluoroaniline, 2,4-dichloroaniline, 2-fluoro-4-chloroaniline, 2-chloro-4-flurooaniline, 2,4-difluoroaniline, and other substituted arylamines). Other commercially available derivatives of 4,6-dichloro-5-aminopyrimidine may be used as a starting material for those compounds of Formula (I) or (II) where $R^1$ is other than hydrogen (e.g., 2-methyl-4,6-dichloro-5-aminopyrimidine and 2-ethyl-4,6-dichloro-5aminopyrimidine). For representative literature syntheses of 4,6-dichloro-5-aminopyrimidine derivatives see: A. Albert et al. in *J. Chem. Soc.,* 3832 (1954) and W. E. Hymans in *J. Heterocycl. Chem.,* 13, 1141 (1976).

Intermediate 1(a) can then be acylated using conventional chemistry well-known to those skilled in the art. For example, intermediate 1(a) may be reacted with the desired aroyl or heteroaroyl chloride in a basic solvent (e.g., pyridine) to produce intermediate 1(b). Alternatively, intermediate 1(a) may be reacted with the desired aroyl or heteroaroyl chloride in a reaction inert solvent (e.g., tetrahydrofuran, methylene chloride, N,N-dimethylacetamide). The addition of a suitable base (e.g., triethylamine, diisopropylethylamine) may help facilitate the reaction. Suitable aroyl chlorides include benzoyl chloride, o-chlorobenzoyl chlorides, o-fluorobenzoyl chloride, p-chlorobenzoyl chloride, p-fluorobenzoyl chloride, 2,4-dichlorobenzoyl chloride, 2,4-difluorobenzoyl chloride, and the like.

Intermediate 1(b) may then be cyclized to the 6-chloropurine intermediate 1(c) by treatment with a condensation agent using analogous procedures and conditions described in U.S. Pat. No.4,728,644, incorporated herein by reference. In a preferred method, intermediate 1(b) can be refluxed in a weak acid (e.g., acetic acid) or sulfuric acid in an appropriate solvent (e.g., isopropyl alcohol, toluene) to provide the hydroxy purine intermediate 1(d) followed by refluxing in phosphorous oxychloride, toluene in the presence of phosphorous oxychloride and triethylamine, or 2,6-lutidine in phosphorous oxychloride to give intermediate 1(c). In another preferred method, 1(b) may be directly converted to 1(c) by refluxing in phosphorous oxychloride; an appropriate co-solvent (e.g., toluene) and/or base (e.g., pyridine, triethylamine) may be added to aid in the condensation.

Finally, the $R^4$ group can be introduced by displacing the chloride on the purine ring at the 6 position.

For compounds of Formula (I) and (11) where $R^4$ is an amino group, intermediate 1(c) is generally stirred with the desired amine (e.g., substituted or unsubstituted aryl($C_1$–$C_4$) alkylamine, substituted or unsubstituted 2-indanylamine, substituted or unsubstituted cyclohexylamine, substituted or unsubstituted cyclopentylamine, substituted or unsubstituted norboranylamine, hydroxy($C_1$–$C_6$)alkylamine, substituted or unsubstituted heteroarylamine, heteroaryl($C_1$–$C_3$)alkylamine, and substituted or unsubstituted 5- to 6-membered heterocyclic amine (i.e., an amine of Formula (Ia) defined above)). The amine may act as the solvent or a solvent (e.g., ethanol, methylene chloride, etc.) may be added to assist in solubilization of the reactants and/or provide a media having the appropriate refluxing temperature to complete the substitution. The reaction may be heated to accelerate the process. In addition, a suitable base such as triethyl amine may be employed to quench the acid produced in the process. Suitable amino compounds can be either purchased commercially or easily prepared using standard procedures well-known to those skilled in the art.

Compounds of Formula (I) above where $R^4$ is a primary or secondary amine can be alkylated, sulfonated and/or acylated to provide additional derivatives (e.g., alkylamines, dialkylamines, sulfonamides, amides, carbamates, ureas, etc.) using standard procedures well-known to those skilled in the art.

Compounds of Formula (I) above where $R^4$ is an amino acid may be prepared as described by A. M. Shalaby et al. in *J. Chem. Res.*, 134–135 (1998). These materials may be further elaborated to amides and esters using standard procedures well-known to those skilled in the art.

Numerous amine compounds of Formula (IA) are available from commercial sources or prepared by known methods readily available to those skilled in the art. Representative preparations of amine compounds of Formula (IA) are illustrated in the Examples below. The preparation of 4-aminopiperidine-4-carboxamide groups of Formula (IA) and 4-amino-4-cyano piperidine groups of Formula (IA) and their benzyl protected precursors are described by P. A. J. Janssen in U.S. Pat. No. 3,161,644, C. van de Westeringh et al. in *J. Med. Chem.*, 7, 619–623 (1964), and K. A. Metwally et al. in *J. Med. Chem.*, 41, 5084–5093 (1998) where the above 4-amino groups are unsubstituted, monosubstituted, disubstituted, or part of a heterocyclic ring. Related bicyclic derivatives are described by K. Frohlich et al. in *Tetrahedron*, 54, 13115–13128 (1998) and references contained therein. Spiro-substituted piperidines of formula (IA) are described by P. A. J. Janssen in U.S. Pat. No. 3,155,670, K. A. Metwally et al. in *J. Med Chem.*, 41, 5084–5093 (1998), T. Toda et al. in *Bull. Chem. Soc. Japan*, 44, 3445–3450 (1971), and W. Brandau and S. Samnick in WO 9522544. The preparation of 3-aminoazetidine-3-carboxamide is described by A. P. Kozikowski and A. H. Fauq in *Synlett*, 783–784 (1991). The preparation of preferred 4-alkylaminopiperidine-4-carboxamide groups of Formula (IA) are depicted in Scheme II below.

Scheme II

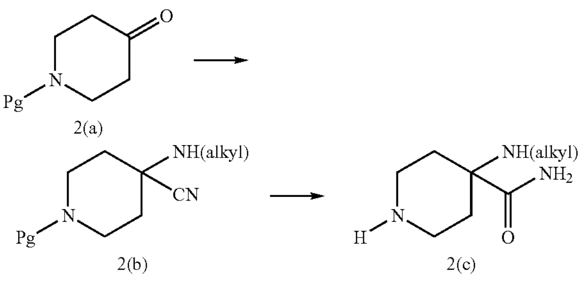

The amino group of 4-piperidinone is first protected to provide intermediate 2(a). A useful protection group is benzyl. 4-piperidinone and derivatives thereof may be purchased commercially from a variety of sources (e.g., Interchem Corporation, Paramus, N.J. and Sigma-Aldrich Co., St. Louis, Mo.). Piperidinone 2(a) is then reacted with the desired alkylamine and potassium cyanide in an aqueous HCl/ethanol solvent mixture at about 0–30° C. The cyano group is converted to the corresponding amide with acid and water. The protecting group is then removed using conventional methods for the particular protecting group employed. For example, a benzyl protecting group may be removed by hydrogenation in the presence of Pd/C.

For compounds of Formula (I) and (II) where $R^4$ is an aminoalkyl, alkylaminoalkyl, or dialkylaminoalkyl group, the chlorine in intermediate 1(c) may first be displaced with a cyano group (e.g., treating with tetrabutylammonium cyanide in the presence of 1,4-diazabicyclo[2.2.2]octane (DABCO) in an aprotic solvent (e.g., acetonitrile) at room temperature). See, e.g., Hocek, et al. *Collect. Czech. Chem. Commun.* 60, 1386 (1995). The cyano can then reduced to the alkyl amine using standard reduction methods well-known to those skilled in the art (e.g., treating with DIBAL or hydrogen in the presence of Pd/C). The amino group can then be alkylated using standard reductive alkylation procedures. Generally, a Schiff base is formed by reacting the amine with the desired ketone or aldehyde in a polar solvent at a temperature from about 10° C. to about 140° C. for about 2 to about 24 hours in the presence of 3 Å molecular sieves. Typically, an equivalent or a slight excess of the amino compound is added to the ketone or aldehyde. Suitable polar solvents include methylene chloride, 1,2-dichloroethane, dimethylsulfoxide, dimethylformamide, alcohols (e.g., methanol or ethanol), or mixtures thereof. A preferred solvent is methanol. In the same reaction vessel, the imine may then be reduced to the secondary amine in the presence of a reducing agent at a temperature from about 0° C. to about 10° C. and then warmed to a temperature from about 20° C. to about 40° C. for about 30 minutes to about 2 hours. Suitable reducing agents include pyridine•borane complex and metal borohydrides, such as sodium borohydride, sodium triacetoxy borohydride and sodium cyanoborohydride. Suitable aldehydes or ketones include paraformaldehyde, acetaldehyde, acetone, benzaldehyde, and the like.

Alternatively, the amino alkyl group may be introduced using the methods described by Hocek, et al. in *Tetrahedron,* 53(6), 2291–2302 (1997). The 6-chloropurine intermediate 1(c) is converted to the 6-acetylpurine compound by reacting intermediate 1(c) with 1-ethoxyvinyl)tri-n-butyltin under $Pd(PPh_3)_4$ catalysis followed by hydrolysis using a mixture of acetone and aqueous HCl (or DMF/aq. HCl mixture) at reflux temperatures to give the acetylated purine. The acetyl group is then easily converted to an amine or substituted amine by reductive amination, a process well-known to those skilled in the art. An examplary procedure employs the desired amine salt (e.g., ammonium chloride, methylammonium chloride, allylammonium chloride, cyclopropylammonium chloride, cyclohexylammonium chloride, dimethylammonium chloride, benzylammonium chloride, etc.) and a reducing agent (e.g., $NaBH_4$, $NaBH_3CN$, or triacetoxyborohydride) in polar solvent at room temperature. See Abdel-Magid, et al., *J. Org. Chem.,* 61, 3849–3862 (1996) for a wide variety of aldehydes, ketones and amines that may be used in either the reductive alkylation of the 6-aminopurine or the reductive amination of the 6-acetylpurine.

For those compounds of Formula (I) and (II) where $R^4$ is an unsubstituted or substituted alkoxy group, intermediate I(c) may be treated with the desired alcohol in the presence of a base (e.g., potassium t-butoxide) and an aprotic solvent (e.g., THF). Suitable alcohols can be either purchased commercially or easily prepared using standard procedures well-known to those skilled in the art.

Alternatively, compounds of Formula (I) or (II) where $R^4$ is a hydroxy or alkoxy substituted alkyl group may be produced by replacing the chlorine group of intermediate 1(c) with the desired electrophile using procedures described by Sugimoto, et al., in *Tetrahedron Letters,* 40, 2139–2140 (1999). The 6-chloropurine intermediate 1(c) is reacted with lithium n-butanetellurolate (tellurium reacted with n-butyllithium) in an aprotic solvent (e.g., THF) at −78° C. followed by the addition of the desired electrophile (e.g., acetaldehyde, benzaldehyde, acetone, methylethyl ketone, etc.) and then warmed to room temperature to form the desired hydroxyalkyl derivative. Alternately, the hydroxy derivative may be formed using the procedures described by Leonard, et al, in *J. Org. Chem.,* 44(25), 4612–4616 (1979). The 6-chloropurine intermediate 1(c) is treated with n-butyl lithium to form the carbanion at −78° C. followed by reaction with the desired electrophile (e.g., ketone or aldehyde) to form the hydroxyalkyl derivative.

In yet another approach, a 6-aroylpurine compound can be prepared by the procedures described by Miyashita, et al, in *Chem. Pharm. Bull,* 46(30), 390–399 (1998). The aroyl group can then be reduced to the corresponding secondary alcohol by treating with a reducing agent such as lithium alumunium hydride. The tertiary alcohol can be obtained upon treatment with an alky metal reagent, such as an alkyl Grignard reagent, in a suitable solvent (e.g., tetrahydrofuran, diethyl ether). Finally, an amine could be introduced by reductive amination (see above).

In the above examples, the resultant hydroxyalkyl group can then be alkylated or acylated to form the desired alkoxy or acylate (e.g., (alkyl)-C(O)—O—, (aryl)-C(O)—O—, (heteroaryl)-C(O)—O—, etc.) using standard procedures well-known to those skilled in the art. Alternatively, the hydroxy group may be condensed with other moieties to provide a variety of substituents (e.g., sulfamyl, sulfonyl, etc.). The aminoalkyl group could be modified in a similar fashion to give amides, sulfonamides, etc.

The $R^4$ group may be attached to the pyrimidine moiety either after (as described above) or prior to cyclization to the purine. Scheme III below illustrates the introduction of the $R^4$ group prior to cyclization to the purine.

Scheme III

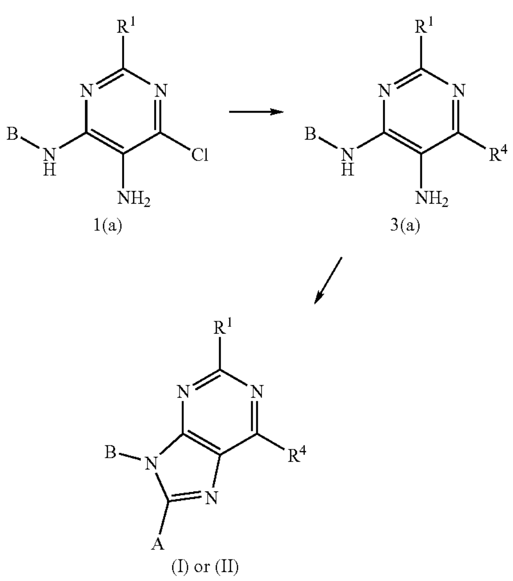

The chlorine group of the pyrimidine intermediate 1(a) may be displaced with the desired nucleophile (e.g., amino compound, alcohol, etc.) to form intermediate 3(a). Intermediate 3(a) can then be condensed with an aryl or heteroaryl carboxylic acid or derivative (eg., acid chloride, ester, etc.) to give purine compound (I). The cyclization may be accomplished using the procedures described by Young, et al, in *J. Med. Chem,* 33, 2073–2080 (1990). For example, intermediate 3(a) is heated with benzoic acid in the presence of polyphosphoric acid (PPA) to a temperature of about 150° C. to about 170° C. for about 1 hour. Alternatively, the desired purine (I) may obtained after the diamine and aryl carboxylic acid are heated to a temperature of about 100° C. in the presence of a dehydrating agent (e.g., propane phosphonic acid cyclic anhydride) in an appropriate solvent (e.g., dioxane).

The B group may be attached directly to the purine moiety as illustrated in Scheme IV below.

Scheme IV

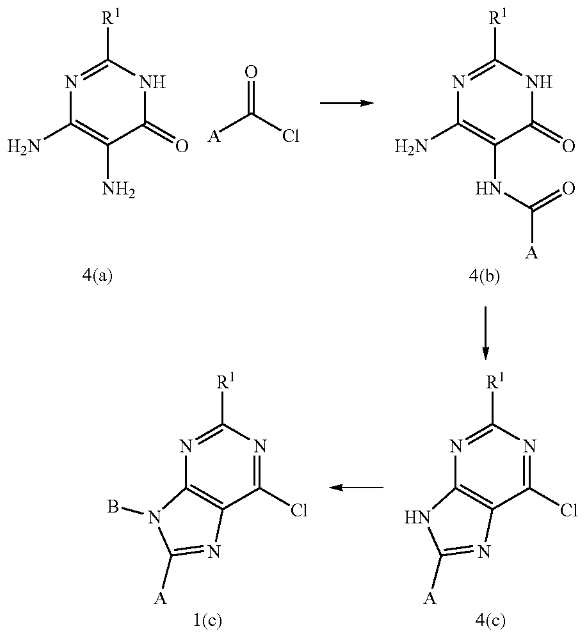

4(a) 4(b) 1(c) 4(c)

Intermediate 4(a) can be first acylated with an acid chloride. Suitable acid chlorides (A-COCl) include those compounds where A is aryl (e.g., benzoyl chloride), substituted aryl (e.g., 2-chlorobenzoyl chloride, 4-chlorobenzoyl chloride, and other substituted aryl acid chlorides), heteroaryl, or substituted heteroaryl. Compound 4(b) may be converted to intermediate 4(c) using with dehydrating agents like $POCl_3$ using procedures described by H. C. Koppel in *J. Org. Chem.*, 23, 1457 (1958) and in *J. Chem. Soc., Perkin Trans. I,* 879 (1984). The B group, where B is aryl, substituted aryl, heteroaryl or substituted heteroaryl, may then be introduced using reagents like $R^1$—$B(OH)_2$, $R^1$—Br or $R^1$—I and Pd catalysts (see Y. Wan et al. in *Synthesis,* 1597–1600 (2002), and references contained therein) or copper(II) catalysts such as cupric acetate or cupric bromide (see S. Ding et al. in *Tetrahedron Lett.,* 42, 8751–8755 (2001), A. Klapars et al. *J. Am. Chem. Soc.* 123, 7727–7729 (2001), and references contained therein). The SNAr reaction may also be useful for introducing electron deficient heterocycles (see M. Medebielle in *New. J. Chem.,* 19, 349 (1995)).

Conventional methods and/or techniques of separation and purification known to one of ordinary skill in the art can be used to isolate the compounds of the present invention, as well as the various intermediates related thereto. Such techniques will be well-known to one of ordinary skill in the art and may include, for example, all types of chromatography (high pressure liquid chromatography (HPLC), column chromatography using common adsorbents such as silica gel, and thin-layer chromatography), recrystallization, and differential (i.e., liquid—liquid) extraction techniques.

The compounds of the present invention may be isolated and used per se or in the form of its pharmaceutically acceptable salt, solvate and/or hydrate. In some instances, the free base is preferred. As used herein the term "free base" refers to an amino group having a lone pair of electrons. The term "salts" refers to inorganic and organic salts of a compound of the present invention which may be incorporated into the molecule via an ionic bond or as a complex. These salts can be prepared in situ during the final isolation and purification of a compound, or by separately reacting the compound or prodrug with a suitable organic or inorganic acid or base and isolating the salt thus formed. Representative salts include the hydrobromide, hydrochloride, hydroiodide, sulfate, bisulfate, nitrate, acetate, trifluoroacetate, oxalate, besylate, palmitiate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate, and laurylsulfonate salts, and the like. Preferred salts include hydrochloride, mesylate and besylate salts. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, e.g., Berge, et al., *J. Pharm. Sci.,* 66, 1–19 (1977).

The term "prodrug" means a compound that is transformed in vivo to yield a compound of Formula (I) or a pharmaceutically acceptable salt, hydrate or solvate of the compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the present invention contains a carboxylic acid functional group, a prodrug can comprise an ester formed by the replacement of the hydrogen atom of the acid group with a group such as $(C_1–C_8)$ alkyl, $(C_2–C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1–C_2)$alkylamino $(C_2–C_3)$alkyl (such as β-dimethylaminoethyl), carbamoyl-$(C_1–C_2)$alkyl, N,N-di$(C_1–C_2)$alkylcarbamoyl-$(C_1–C_2)$alkyl and piperidino-, pyrrolidino- or morpholino$(C_2–C_3)$alkyl.

Similarly, if a compound of the present invention contains an alcohol functional group, a prodrug can be formed by the replacement of the hydrogen atom of the alcohol group with a group such as $(C_1–C_6)$alkanoyloxymethyl, 1-($(C_1–C_6)$ alkanoyloxy)ethyl, 1-methyl-1-($(C_1–C_6)$alkanoyloxy)ethyl, $(C_1–C_6)$alkoxycarbonyloxymethyl, N-$(C_1–C_6)$alkoxycarbonylaminomethyl, succinoyl, $(C_1–C_6)$alkanoyl, α-amino $(C_1–C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, $P(O)(O(C_1–C_6)alkyl)_2$ or glycosyl (the radical resulting from the removal of a hydroxyl group of the hemiacetal form of a carbohydrate).

If a compound of the present invention incorporates an amine functional group, a prodrug can be formed by the replacement of a hydrogen atom in the amine group with a group such as R-carbonyl, RO-carbonyl, NRR'-carbonyl where R and R' are each independently $(C_1–C_{10})$alkyl, ($C_3$–$C_7$)cycloalkyl, benzyl, or R-carbonyl is a natural α-aminoacyl or natural α-aminoacyl-natural α-aminoacyl, —C(OH)C(O)OY' wherein Y' is H, ($C_1$–$C_6$)alkyl or benzyl, —C($OY_0$)$Y_1$ wherein $Y_0$ is ($C_1$–$C_4$) alkyl and $Y_1$ is ($C_1$–$C_6$) alkyl, carboxy($C_1$–$C_6$)alkyl, amino($C_1$–$C_4$)alkyl or mono-N- or di-N,N-($C_1$–$C_6$)alkylaminoalkyl, —C($Y_2$)$Y_3$ wherein $Y_2$ is H or methyl and $Y_3$ is mono-N- or di-N,N-($C_1$–$C_6$) alkylamino, morpholino, piperidin-1-yl or pyrrolidin-1-yl.

The compounds of the present invention (including the inventive intermediates) may contain asymmetric or chiral centers; therefore, the compounds and intermediates may exist in different stereoisomeric forms (e.g., enantiomers and diasteroisomers). It is intended that all stereoisomeric forms of the intermediates and compounds of the present invention as well as mixtures thereof, including racemic mixtures, form a part of the present invention. In addition, the present invention embraces all geometric and positional isomers. For example, if an intermediate or compound of the present invention incorporates a double bond or a fused ring, both the cis- and trans- forms, as well as mixtures, are embraced within the scope of the invention.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

The compounds of the present invention may exist in unsolvated as well as solvated forms with pharmaceutically acceptable solvents such as water, ethanol, and the like, and it is intended that the invention embrace both solvated and unsolvated forms.

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons.

The present invention also embraces isotopically-labeled compounds of the present invention (including intermediates) which are identical to those recited herein, but for the fact that one or more atoms are replaced by an atom having an atomic mass or mass number different from the atomic mass or mass number usually found in nature. Examples of isotopes that can be incorporated into the intermediates or compounds of the invention include isotopes of hydrogen, carbon, nitrogen, oxygen, phosphorus, sulfur, fluorine, iodine, and chlorine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{123}I$, $^{125}I$ and $^{36}Cl$, respectively.

Certain isotopically-labeled compounds of the present invention (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Compounds of the present invention are useful for treating diseases, conditions and disorders modulated by cannabinoid receptor antagonists; therefore, another embodiment of the present invention is a pharmaceutical composition comprising a therapeutically effective amount of a compound of the present invention and a pharmaceutically acceptable excipient, diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present invention further provides a method of treating diseases, conditions and/or disorders modulated by cannabinoid receptor antagonists in an animal that includes administering to an animal in need of such treatment a therapeutically effective amount of a compound of the present invention or a pharmaceutical composition comprising an effective amount of a compound of the present invention and a pharmaceutically acceptable excipient, diluent, or carrier. The method is particularly useful for treating diseases, conditions and/or disorders modulated by cannabinoid receptor (in particular, CB1 receptor) antagonists.

Preliminary investigations have indicated that the following diseases, conditions, and/or disorders are modulated by cannabinoid receptor antagonists: eating disorders (e.g., binge eating disorder, anorexia, and bulimia), weight loss or control (e.g., reduction in calorie or food intake, and/or appetite suppression), obesity, depression, atypical depression, bipolar disorders, psychoses, schizophrenia, behavioral addictions, suppression of reward-related behaviors (e.g., conditioned place avoidance, such as suppression of cocaine- and morphine-induced conditioned place preference), substance abuse, addictive disorders, impulsivity, alcoholism (e.g., alcohol abuse, addiction and/or dependence including treatment for abstinence, craving reduction and relapse prevention of alcohol intake), tobacco abuse (e.g., smoking addiction, cessation and/or dependence including treatment for craving reduction and relapse prevention of tobacco smoking), dementia (including memory loss, Alzheimer's disease, dementia of aging, vascular dementia, mild cognitive impairment, age-related cognitive decline, and mild neurocognitive disorder), sexual dysfunction in males (e.g., erectile difficulty), seizure disorders, epilepsy, gastrointestinal disorders (e.g., dysfunction of gastrointestinal motility or intestinal propulsion), attention deficit disorders (ADD which includes attention hyperactivity disorder (ADHD)), Parkinson's disease, and type II diabetes.

Accordingly, the compounds of the present invention described herein are useful in treating diseases, conditions, or disorders that are modulated by cannabinoid receptor antagonists. Consequently, the compounds of the present invention (including the compositions and processes used therein) may be used in the manufacture of a medicament for the therapeutic applications described herein.

Other diseases, conditions and/or disorders for which cannabinoid receptor antagonists may be effective include: premenstrual syndrome or late luteal phase syndrome, migraines, panic disorder, anxiety, post-traumatic syndrome, social phobia, cognitive impairment in non-demented individuals, non-amnestic mild cognitive impairment, post operative cognitive decline, disorders associated with impulsive behaviours (such as, disruptive behaviour disorders (e.g., anxiety/depression, executive function improvement, tic disorders, conduct disorder and/or oppositional defiant disorder), adult personality disorders (e.g., borderline personality disorder and antisocial personality disorder), diseases associated with impulsive behaviours (e.g., substance abuse, paraphilias and self-mutilation), and impulse control disorders (e.g., intermittene explosive disorder, kleptomania, pyromania, pathological gambling, and trichotillomania)), obsessive compulsive disorder, chronic fatigue syndrome, sexual dysfunction in males (e.g., premature ejaculation), sexual dysfunction in females, disorders of sleep (e.g., sleep apnea), autism, mutism, neurodengenerative movement disorders, spinal cord injury, damage of the central nervous system (e.g., trauma), stroke, neurodegenerative diseases or toxic or infective CNS diseases (e.g., encephalitis or meningitis), cardiovascular disorders (e.g., thrombosis), and diabetes.

The compounds of the present invention can be administered to a patient at dosage levels in the range of from about 0.7 mg to about 7,000 mg per day. For an adult human having a body weight of about 70 kg, a dosage in the range of from about 0.01 mg to about 100 mg per kilogram body weight is typically sufficient. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include anti-obesity agents such as apolipoprotein-B secretion/microsomal triglyceride transfer protein (apo-B/MTP) inhibitors (such as edipatapide or dirlotapide), 11β-hydroxy steroid dehydrogenase-1 (11β-HSD type 1) inhibitors, peptide $YY_{3-36}$ and analogs thereof, MCR-4 agonists, cholecystokinin-A (CCK-A) agonists, monoamine reuptake inhibitors (such as sibutramine), sympathomimetic agents, $\beta_3$ adrenergic receptor agonists, dopamine receptor agonists (such as bromocriptine), melanocyte-stimulating hormone receptor analogs, 5HT2c receptor agonists, melanin concentrating hormone antagonists, leptin (the OB protein), leptin analogs, leptin receptor agonists, galanin antagonists, lipase inhibitors (such as tetrahydrolipstatin, i.e. orlistat), anorectic agents (such as a bombesin agonist), Neuropeptide-Y receptor antagonists, thyromimetic agents, dehydroepiandrosterone or an analog thereof, glucocorticoid receptor agonists or antagonists, orexin receptor antagonists, glucagon-like peptide-1 receptor agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, ghrelin receptor antagonists, histamine 3 receptor antagonists or inverse agonists, neuromedin U receptor agonists and the like. Other anti-obesity agents, including the preferred agents set forth hereinbelow, are well known, or will be readily apparent in light of the instant disclosure, to one of ordinary skill in the art.

Especially preferred are anti-obesity agents selected from the group consisting of orlistat, sibutramine, bromocriptine, ephedrine, leptin, peptide $YY_{3-36}$ and analogs thereof, and pseudoephedrine. Preferably, compounds of the present invention and combination therapies are administered in conjunction with exercise and a sensible diet.

Representative anti-obesity agents for use in the combinations, pharmaceutical compositions, and methods of the invention can be prepared using methods known to one of ordinary skill in the art, for example, sibutramine can be prepared as described in U.S. Pat. No. 4,929,629; bromocriptine can be prepared as described in U.S. Pat. Nos. 3,752,814 and 3,752,888; orlistat can be prepared as described in U.S. Pat. Nos. 5,274,143; 5,420,305; 5,540,917; and 5,643,874; and $PYY_{3-36}$ (including analogs) can be prepared as described in US Publication No. 2002/0141985 and WO 03/027637. All of the above recited U.S. patents are incorporated herein by reference.

Other suitable pharmaceutical agents that may be administered in combination with the compounds of the present invention include agents designed to treat tobacco abuse (e.g., nicotine receptor partial agonists, bupropion hypochloride (also known under the tradename Zyban™) and nicotine replacement therapies), agents to treat erectile dysfunction (e.g., dopaminergic agents, such as apomorphine), ADD/ADHD agents (e.g., Ritalin™, Strattera™, Concerta™ and Adderall™), and agents to treat alcoholism, such as opioid antagonists (e.g., naltrexone (also known under the tradename ReVia™) and nalmefene), disulfiram (also known under the tradename Antabuse™), and acamprosate (also known under the tradename Campral™)). In addition, agents for reducing alcohol withdrawal symptoms may also be co-administered, such as benzodiazepines, beta-blockers, clonidine, carbamazepine, pregabalin, and gabapentin (Neurontin™). Treatment for alcoholism is preferably administered in combination with behavioral therapy including such components as motivational enhancement therapy, cognitive behavioral therapy, and referral to self-help groups, including Alcohol Anonymous (AA).

Other pharmaceutical agents that may be useful include COX-2 inhibitors; antihypertensive agents; antidepressants (e.g., fluoxetine hydrochloride (Prozac™)); cognitive improvement agents (e.g., donepezil hydrochloride (Aircept™) and other acetylcholinesterase inhibitors); neuroprotective agents (e.g., memantine); antipsychotic medications (e.g., ziprasidone (Geodon™), risperidone (Risperdal™), and olanzapine (Zyprexa™)); insulin and insulin analogs (e.g., LysPro insulin); GLP-1 (7-37) (insulinotropin) and GLP-1 (7-36)-$NH_2$; sulfonylureas and analogs thereof: chlorpropamide, glibenclamide, tolbutamide, tolazamide, acetohexamide, Glypizide®, glimepiride, repaglinide, meglitinide; biguanides: mefformin, phenformin, buformin; α2-antagonists and imidazolines: midaglizole, isaglidole, deriglidole, idazoxan, efaroxan, fluparoxan; other insulin secretagogues: linogliride, A-4166; glitazones: ciglitazone, Actos® (pioglitazone), englitazone, troglitazone, darglitazone, Avandia® (BRL49653); fatty acid oxidation inhibitors: clomoxir, etomoxir; α-glucosidase inhibitors: acarbose, miglitol, emiglitate, voglibose, MDL-25,637, camiglibose, MDL-73,945; β-agonists: BRL 35135, BRL 37344, RO 16-8714, ICI D7114, CL 316,243; phosphodiesterase inhibitors: L-386,398; lipid-lowering agents: benfluorex: fenfluramine; vanadate and vanadium complexes (e.g., Naglivan®) and peroxovanadium complexes; amylin antagonists; glucagon antagonists; gluconeogenesis inhibitors; somatostatin analogs; antilipolytic agents: nicotinic acid, acipimox, WAG 994, pramlintide (Symlin™), AC 2993, nateglinide, aldose reductase inhibitors (e.g., zopolrestat), glycogen phosphorylase inhibitors, sorbitol dehydrogenase inhibitors, sodium-hydrogen exchanger type 1 (NHE-1) inhibitors and/or cholesterol biosynthesis inhibitors or cholesterol absorption inhibitors, especially a HMG-CoA reductase inhibitor, or a HMG-CoA synthase inhibitor, or a HMG-CoA reductase or synthase gene expression inhibitor, a CETP inhibitor, a bile acid sequesterant, a fibrate, an ACAT inhibitor, a squalene synthetase inhibitor, an anti-oxidant or niacin. The compounds of the present invention may also be administered in combination with a naturally occurring compound that acts to lower plasma cholesterol levels. Such naturally occurring compounds are commonly called nutraceuticals and include, for example, garlic extract, Hoodia plant extracts, and niacin.

The dosage of the additional pharmaceutical agent is generally dependent upon a number of factors including the health of the subject being treated, the extent of treatment desired, the nature and kind of concurrent therapy, if any, and the frequency of treatment and the nature of the effect desired. In general, the dosage range of the additional pharmaceutical agent is in the range of from about 0.001 mg to about 100 mg per kilogram body weight of the individual per day, preferably from about 0.1 mg to about 10 mg per kilogram body weight of the individual per day. However, some variability in the general dosage range may also be required depending upon the age and weight of the subject being treated, the intended route of administration, the particular anti-obesity agent being administered and the like. The determination of dosage ranges and optimal dosages for a particular patient is also well within the ability of one of ordinary skill in the art having the benefit of the instant disclosure.

According to the methods of the invention, a compound of the present invention or a combination of a compound of the present invention and at least one additional pharmaceutical agent is administered to a subject in need of such treatment, preferably in the form of a pharmaceutical composition. In the combination aspect of the invention, the compound of the present invention and at least one other pharmaceutical agent (e.g., anti-obesity agent, nicotine receptor partial agonist, ADD/ADHD agent, dopaminergic agent, or opioid antagonist) may be administered either separately or in the pharmaceutical composition comprising both. It is generally preferred that such administration be oral. However, if the subject being treated is unable to swallow, or oral administration is otherwise impaired or undesirable, parenteral or transdermal administration may be appropriate.

According to the methods of the invention, when a combination of a compound of the present invention and at least one other pharmaceutical agent are administered together, such administration can be sequential in time or simultaneous with the simultaneous method being generally preferred. For sequential administration, a compound of the present invention and the additional pharmaceutical agent can be administered in any order. It is generally preferred that such administration be oral. It is especially preferred that such administration be oral and simultaneous. When a compound of the present invention and the additional pharmaceutical agent are administered sequentially, the administration of each can be by the same or by different methods.

According to the methods of the invention, a compound of the present invention or a combination of a compound of the present invention and at least one additional pharmaceutical agent (referred to herein as a "combination") is preferably administered in the form of a pharmaceutical composition. Accordingly, a compound of the present invention or a combination can be administered to a patient separately or together in any conventional oral, rectal, transdermal, parenteral, (for example, intravenous, intramuscular, or subcutaneous) intracisternal, intravaginal, intraperitoneal, intravesical, local (for example, powder, ointment or drop), or buccal, or nasal, dosage form.

Compositions suitable for parenteral injection generally include pharmaceutically acceptable sterile aqueous or nonaqueous solutions, dispersions, suspensions, or emulsions, and sterile powders for reconstitution into sterile injectable solutions or dispersions. Examples of suitable aqueous and nonaqueous carriers or diluents (including solvents and vehicles) include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain excipients such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, powders, and granules. In such solid dosage forms, a compound of the present invention or a combination is admixed with at least one inert customary pharmaceutical excipient (or carrier) such as sodium citrate or dicalcium phosphate or (a) fillers or extenders (e.g., starches, lactose, sucrose, mannitol, silicic acid and the like); (b) binders (e.g., carboxymethylcellulose, alginates, gelatin, polyvinylpyrrolidone, sucrose, acacia and the like); (c) humectants (e.g., glycerol and the like); (d) disintegrating agents (e.g., agar-agar, calcium carbonate, potato or tapioca starch, alginic acid, certain complex silicates, sodium carbonate and the like); (e) solution retarders (e.g., paraffin and the like); (f) absorption accelerators (e.g., quaternary ammonium compounds and the like); (g) wetting agents (e.g., cetyl alcohol, glycerol monostearate and the like); (h) adsorbents (e.g., kaolin, bentonite and the like); and/or (i) lubricants (e.g., talc, calcium stearate, magnesium stearate, solid polyethylene glycols, sodium lauryl sulfate and the like). In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well known in the art. They may also contain opacifying agents, and can also be of such composition that they release the compound of the present invention and/or the additional pharmaceutical agent in a delayed manner. Examples of embedding compositions that can be used are polymeric substances and waxes. The drug can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the compound of the present invention or the combination, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed oil, groundnut oil, corn germ oil, olive oil, castor oil, sesame seed oil and the like), glycerol, tetrahydrofurfuryl alcohol, polyethylene glycols and fatty acid esters of sorbitan, or mixtures of these substances, and the like.

Besides such inert diluents, the composition can also include excipients, such as wetting agents, emulsifying and suspending agents, sweetening, flavoring, and perfuming agents.

Suspensions, in addition to the compound of the present invention or the combination, may further comprise suspending agents, e.g., ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing a compound of the present invention or a combination with suitable non-irritating excipients or carriers, such as cocoa butter, polyethylene glycol or a suppository wax which are solid at ordinary room temperature but liquid at body temperature and therefore melt in the rectum or vaginal cavity thereby releasing the active component(s).

Dosage forms for topical administration of the compounds of the present invention and combinations of the compounds of the present invention with anti-obesity agents may comprise ointments, powders, sprays and inhalants. The drugs are admixed under sterile conditions with a pharmaceutically acceptable carrier, and any preservatives, buffers, or propellants that may be required. Ophthalmic formulations, eye ointments, powders, and solutions are also intended to be included within the scope of the present invention.

The following paragraphs describe exemplary formulations, dosages, etc. useful for non-human animals. The administration of the compounds of the present invention and combinations of the compounds of the present invention with anti-obesity agents can be effected orally or non-orally (e.g., by injection).

An amount of a compound of the present invention or combination of a compound of the present invention with an anti-obesity agent is administered such that an effective dose is received. Generally, a daily dose that is administered orally to an animal is between about 0.01 and about 1,000 mg/kg of body weight, preferably between about 0.01 and about 300 mg/kg of body weight.

Conveniently, a compound of the present invention (or combination) can be carried in the drinking water so that a therapeutic dosage of the compound is ingested with the daily water supply. The compound can be directly metered into drinking water, preferably in the form of a liquid, water-soluble concentrate (such as an aqueous solution of a water-soluble salt).

Conveniently, a compound of the present invention (or combination) can also be added directly to the feed, as such, or in the form of an animal feed supplement, also referred to as a premix or concentrate. A premix or concentrate of the compound in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the compound in the finished feed with which the premix is blended. Preferably, the compound is thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carrier. It will be appreciated that the proportions of compound in the concentrate are capable of wide variation since the amount of the compound in the finished feed may be adjusted by blending the appropriate proportion of premix with the feed to obtain a desired level of compound.

High potency concentrates may be blended by the feed manufacturer with proteinaceous carrier such as soybean oil meal and other meals, as described above, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound of the present invention. The mixtures are thoroughly blended by standard procedures, such as in a twin shell blender, to ensure homogeneity.

If the supplement is used as a top dressing for the feed, it likewise helps to ensure uniformity of distribution of the compound across the top of the dressed feed.

Drinking water and feed effective for increasing lean meat deposition and for improving lean meat to fat ratio are generally prepared by mixing a compound of the present invention with a sufficient amount of animal feed to provide from about $10^{-3}$ to about 500 ppm of the compound in the feed or water.

The preferred medicated swine, cattle, sheep and goat feed generally contain from about 1 to about 400 grams of a compound of the present invention (or combination) per ton of feed, the optimum amount for these animals usually being about 50 to about 300 grams per ton of feed.

The preferred poultry and domestic pet feeds usually contain about 1 to about 400 grams and preferably about 10 to about 400 grams of a compound of the present invention (or combination) per ton of feed.

For parenteral administration in animals, the compounds of the present invention (or combination) may be prepared in the form of a paste or a pellet and administered as an implant, usually under the skin of the head or ear of the animal in which increase in lean meat deposition and improvement in lean meat to fat ratio is sought.

In general, parenteral administration involves injection of a sufficient amount of a compound of the present invention (or combination) to provide the animal with about 0.01 to about 20 mg/kg/day of body weight of the drug. The preferred dosage for poultry, swine, cattle, sheep, goats and domestic pets is in the range of from about 0.05 to about 10 mg/kg/day of body weight of drug.

Paste formulations can be prepared by dispersing the drug in a pharmaceutically acceptable oil such as peanut oil, sesame oil, corn oil or the like.

Pellets containing an effective amount of a compound of the present invention, pharmaceutical composition, or combination can be prepared by admixing a compound of the present invention or combination with a diluent such as carbowax, carnuba wax, and the like, and a lubricant, such as magnesium or calcium stearate, can be added to improve the pelleting process.

It is, of course, recognized that more than one pellet may be administered to an animal to achieve the desired dose level which will provide the increase in lean meat deposition and improvement in lean meat to fat ratio desired. Moreover, implants may also be made periodically during the animal treatment period in order to maintain the proper drug level in the animal's body.

The present invention has several advantageous veterinary features. For the pet owner or veterinarian who wishes to increase leanness and/or trim unwanted fat from pet animals, the instant invention provides the means by which this may be accomplished. For poultry, beef and swine breeders, utilization of the method of the present invention yields leaner animals that command higher sale prices from the meat industry.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), and AstraZeneca Pharmaceuticals (London, England).

General Experimental Procedures

NMR spectra were recorded on a Varian Unity™ 400 or 500 (available from Varian Inc., Palo Alto, Calif.) at room temperature at 400 and 500 MHz $^1H$, respectively. Chemical shifts are expressed in parts per million (δ) relative to residual solvent as an internal reference. The peak shapes are denoted as follows: s, singlet; d, doublet; t, triplet; q, quartet; m, multiplet; br s, broad singlet; v br s, very broad singlet; br m, broad multiplet; 2s, two singlets. In some cases only representative $^1H$ NMR peaks are given.

Mass spectra were recorded by direct flow analysis using positive and negative atmospheric pressure chemical ionization (APcI) scan modes. A Waters APcI/MS model ZMD mass spectrometer equipped with Gilson 215 liquid handling system was used to carry out the experiments.

Mass spectrometry analysis was also obtained by RP-HPLC gradient method for chromatographic separation. Molecular weight identification was recorded by positive and negative electrospray ionization (ESI) scan modes. A Waters/Micromass ESI/MS model ZMD or LCZ mass spectrometer equipped with Gilson 215 liquid handling system and HP 1100 DAD was used to carry out the experiments.

Where the intensity of chlorine or bromine-containing ions are described, the expected intensity ratio was observed (approximately 3:1 for $^{35}Cl/^{37}Cl$-containing ions and 1:1 for $^{79}Br/^{81}Br$-containing ions) and only the lower mass ion is given. MS peaks are reported for all examples.

Optical rotations were determined on a PerkinElmer™ 241 polarimeter (available from PerkinElmer Inc., Wellesley, Mass.) using the sodium D line (λ=589 nm) at the indicated temperature and are reported as follows $[\alpha]_D^{temp}$, concentration (c=g/100 ml), and solvent.

Column chromatography was performed with either Baker™ silica gel (40 μm; J. T. Baker, Phillipsburg, N.J.) or Silica Gel 50 (EM Sciences™, Gibbstown, N.J.) in glass columns or in Biotage™ columns (ISC, Inc., Shelton, Conn.) under low nitrogen pressure. Radial chromatography was performed using a Chromatotron™ (Harrison Research).

Preparation of Key Intermediates

Preparation of Intermediate 6-Chloro-N4-(4-chlorophenyl)-pyrimidine-4,5-diamine (I-(1A-1)a)

I-(1A-1)a

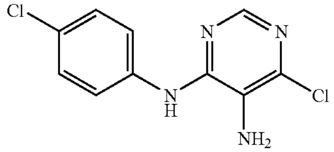

5-amino-4,6-dichloropyrimidine (5.00 g, 29 mmol) and 4-chloroaniline (4.71 g, 36 mmol) were suspended in 80 ml $H_2O$ and 12 ml ethanol. Concentrated HCl (1.2 ml, 14.5 mmol) was added at room temperature followed by warming reaction to 82° C. After stirring for 19 hours the reaction was cooled to room temperature and stirred for 60 hours. The precipitate was collected on a sintered glass funnel and rinsed with water followed by hexanes. After drying under vacuum, I-(1A-1)a was obtained as an off-white solid (7.38 g, 98%): +ESI MS (M+1) 255.3; $^1$H NMR: (400 MHz, $CD_3OD$): δ 7.87 (s, 1H), 7.66 (d, J=8.7 Hz, 2 H), 7.30 (d, J=8.7 Hz, 2 H).

Preparation of Intermediate 2,4-Dichloro-N-[4-chloro-6-(4-chlorophenyl-amino)-pyrimidin-5-yl]-benzamide (I-(1A-1)b)

I-(1A-1)b

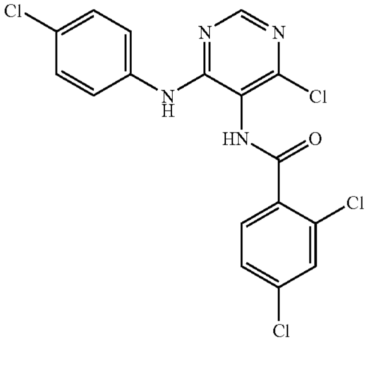

6-Chloro-N4-(4-chlorophenyl)-pyrimidine-4,5-diamine I-(1A-1)a (34 g, 134 mmol) in pyridine (150 ml) was cooled to 0° C. and to it was added 2,4-dichlorobenzoyl chloride (25 ml, 178 mmol). The reaction was allowed to warm to ambient temperature overnight. The solid precipitate was collected by vacuum filtration and dried under high vacuum to yield the title compound I-(1A-1)b as a colorless solid (14 g, 25%). The pyridine solution was concentrated under reduced pressure and then triturated with methanol (500 ml) to provide additional material (35 g, 60%): +ESI MS (M+1) 427.4; $^1$H NMR: (400 MHz, DMSO-$d_6$): δ 10.08 (s, 1H), 9.16 (s, 1H), 8.38 (s, 1H), 7.97 (d, J=8.7 Hz, 1H), 7.75 (d, J=2.0 Hz, 2H), 7.64–7.60 (m, 3H), 7.40 (d, J=8.7 Hz, 2H).

Preparation of Intermediate 9-(4-Chlorophenyl)-8-(2,4-dichlorophenyl)-9H-purin-6-ol (I-(1A-1)c)

I-(1A-1)c

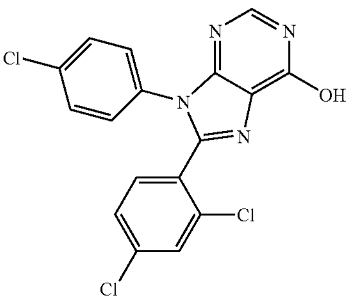

A suspension of 2,4-dichloro-N-[4-chloro-6-(4-chlorophenylamino)-pyrimidin-5-yl]-benzamide I-(1A-1)b (48 g, 0.11 mol) in acetic acid (1 l) was heated to reflux for 7 hours. The reaction mixture was cooled to 0° C., the product (colorless needles) was collected by vacuum filtration, and the solid was washed with additional acetic acid, ethyl acetate, and then ether. The product was dried overnight under high vacuum to afford the title compound I-(1A-1)c (32 g, 73%) as a colorless, fluffy solid. The mother liquor was concentrated under reduced pressure and the solid crystallized from methanol to provide additional material (16 g) as a colorless solid: mp 314–315° C.; +ESI MS (M+1) 391.3; $^1$H NMR: (400 MHz, $CD_3OD$): δ 8.06 (s, 1H), 7.61 (d, J=8.3 Hz, 1H), 7.52 (d, J=2.1 Hz, 1H), 7.48–7.41 (m, 3H), 7.31 (d, J=8.7 Hz, 2H).

Preparation of Intermediate 6-Chloro-9-(4-chlorophenyl)-8-(2,4-dichloro-phenyl)-9H-purine (I-(1A-1)d)

I-(1A-1)d

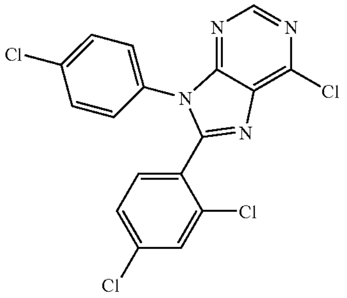

9-(4-Chlorophenyl)-8-(2,4-dichlorophenyl)-9H-purin-6-ol I-(1A-1)c (6.5 g, 17 mmol) was heated to reflux in $POCl_3$ (3 ml) overnight. The reaction mixture was concentrated under reduced pressure and the residue was dissolved into chloroform and poured onto ice. The organic layer was separated and washed with saturated aqueous $NaHCO_3$; the organic layers were combined, dried ($Na_2SO_4$), filtered, and concentrated under reduced pressure. The residue was taken up in 1:1 methylene chloride/diethyl ether (200 ml) and was then filtered to remove residual starting material. Concentration of the organic layer gave the title compound I-(1A-1)d as a yellow foam (5.8 g, 85%): +ESI MS (M+1) 411.4;

$^1H$ NMR: (400 MHz, DMSO-$d_6$): δ 8.83 (s, 1H), 7.79–7.75 (m, 2H), 7.63–7.58 (m, 1H), 7.56 (d, J=8.7 Hz, 2H), 7.42 (d, J=6.7 Hz, 2H).

Preparation of Intermediate 2-Chloro-N-[4-chloro-6-(4-chlorophenylamino)-pyrimidin-5-yl]-benzamide (I-(4A-7)a)

I-(4A-7)a

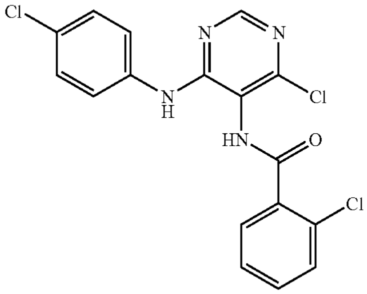

6-Chloro-N4-(4-chlorophenyl)-pyrimidine-4,5-diamine I-(1A-1)a (1.00 g, 3.92 mmol) was dissolved in 6 ml of N,N-dimethylacetamide giving a clear brown solution. After cooling to 5° C., neat 2-chlorobenzoyl chloride (0.80 g, 4.34 mmol) was added over 1 minute. The solution was warmed to room temperature and stirred for 4 hours. Addition of water (15 ml) caused white precipitate to come out of solution. The mixture was stirred for an additional 30 minutes at room temperature, then the precipitate was collected by vacuum filtration, rinsing with $H_2O$ and then hexanes. The solid was further dried under vacuum to give I-(4A-7)a as a colorless solid (1.27 g, 82%): +ACPI MS (M+1) 393.1; $^1H$ NMR (400 MHz, DMSO-$d_6$) δ 10.02 (s, 1H), 9.11 (s, 1H), 8.40 (s, 1H), 7.93 (dd, J=7.4, 1.6 Hz, 1H), 7.66–7.40 (m, 7H).

Preparation of Intermediate 9-(4-Chlorophenyl)-8-(2-chlorophenyl)-9H-purin-6-ol (I-(4A-7)b)

I-(4A-7)b

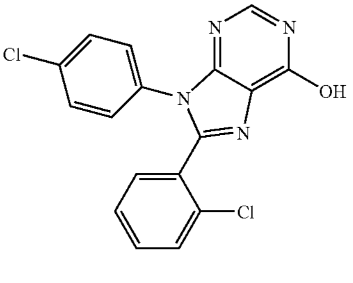

To a suspension of 2-chloro-N-[4-chloro-6-(4-chlorophenylamino)-pyrimidin-5-yl]-benzamide I-(4A-7)a (1.00 g, 2.54 mmol) in isopropanol (20 ml) was added neat $H_2SO_4$ (410 μl, 7.4 mmol) at room temperature. The reaction was refluxed for 8 hours followed by cooling to room temperature and stirring for 16 hr. To the heterogeneous solution was added 20 ml of water to promote further product precipitation. After stirring for 1 an additional hour at room temperature, the solid was collected on a sintered glass funnel, rinsing with water followed by hexanes. The product was further dried under reduced pressure to give I-(4A-7)b as a colorless solid (0.72 g, 80%): $^1H$ NMR: (400 MHz, DMSO-$d_6$): δ 12.57 (s, 1H), 8.08 (d, J=4.1 Hz, 1 H), 7.66 (dd, J=7.4, 1.2 Hz, 1H), 7.51–7.41 (m, 5H), 7.33–7.29 (m, 2H).

Preparation of Intermediate 6-chloro-9-(4-chlorophenyl)-8-(2-chlorophenyl)-9H-purine (I-(4A-7)c)

I-(4A-7)c

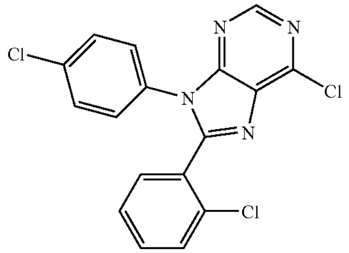

9-(4-Chlorophenyl)-8-(2-chlorophenyl)-9H-purin-6-ol I-(4A-7)b (2.49 g, 6.97 mmol) was suspended in 50 ml of toluene. Triethylamine (1.07 ml, 7.68 mmol) was added followed by addition of $POCl_3$ (720 μl, 7.72 mmol) at room temperature. The reaction was warmed to reflux and stirred for 23 hours to give a clear orange solution. After cooling the reaction to room temperature it was concentrated under reduced pressure, diluted with isopropanol (50 ml) and then concentrated further under reduced pressure until copious amount of precipitate came out of solution. The concentrated suspension was cooled in an ice bath and stirred for 2 hours. The precipitate was collected on a sintered glass funnel and rinsed with cold isopropanol to afford, after drying in vacuo, I-(4A-7)c as an off-white solid (2.13 g, 82%): +ESI MS (M+1) 375.1; $^1H$ NMR (400 MHz, DMSO-$d_6$) δ 8.84 (s, 1H), 7.76 (dd, J=7.46, 1.2 Hz, 1H), 7.58–7.40 (m, 7H).

Preparation of Intermediate 6-Chloro-N4-(4-chlorophenyl)-2-methyl-pyrimidine-4,5-diamine (I-(7A-80)a)

I-(7A-80)a

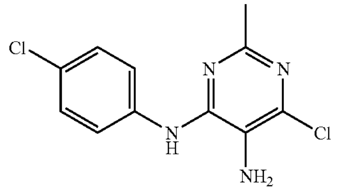

4,6-Dichloro-2-methylpyrimidin-5-ylamine (100 mg, 0.56 mmol) and 4-chlorophenylamine (86 mg, 0.68 mmol) were combined in $H_2O$ (1.5 ml) and 10:1 ethanol/HCl (0.24 ml) and heated to reflux for 6 hours. The reaction mixture was cooled and $H_2O$ added to it. The product was collected by filtration and dried on high vacuum to give the desired compound I-(7A-80)a as a tan solid (173 mg) that was carried on crude: +ESI MS (M+1) 269.2.

Preparation of Intermediate N-[4-Chloro-6-(4-chlorophenylamino)-2-methylpyrimidin-5-yl]-2-fluorobenzamide (I-(7A-80)b)

I-(7A-80)b

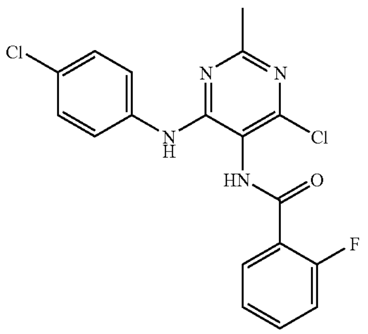

2-Fluorobenzoyl chloride (93 µl, 0.78 mmol) was added to 6-chloro-N4-(4-chlorophenyl)-2-methylpyrimidine-4,5-diamine I-(7A-80)a (173 mg) and pyridine (1 ml) and stirred at room temperature for 7 h. The reaction was incomplete at this time so an additional 1.5 equivalents of 2-fluorobenzoyl chloride was added to the reaction mixture and continued stirring overnight at room temperature. The reaction was extracted from saturated $NaHCO_3$ solution into ethyl acetate. The organic layers were combined, dried ($Na_2SO_4$), filtered, and concentrated to dryness to afford the desired crude product I-(7A-80)b (0.25 g): +ESI MS (M+1) 391.2.

Preparation of Intermediate 6-Chloro-9-(4-chlorophenyl)-8-(2-fluorophenyl)-2-methyl-9H-purine (I-(7A-80)c)

I-(7A-80)c

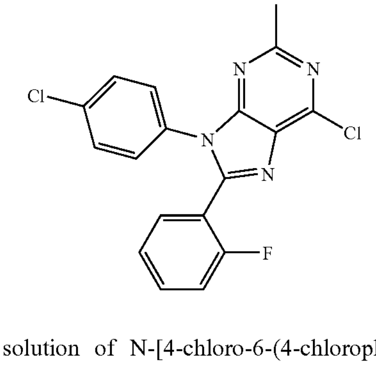

A solution of N-[4-chloro-6-(4-chlorophenylamino)-2-methylpyrimidin-5-yl]-2-fluorobenzamide I-(7A-80)b (0.25 g) in dioxane (6 ml) was treated with 50% propanephosphoric acid cyclic anhydride (PPM) in ethyl acetate (0.6 ml) and heated to reflux overnight. It was determined that the product was a mixture of desired product and the hydroxy compound (displacement of the chlorine atom). The reaction was therefore concentrated under reduced pressure and heated overnight in refluxing $POCl_3$ (6 ml). The reaction mixture was concentrated to dryness, diluted with ethyl acetate, and poured onto ice. Saturated $NaHCO_3$ solution was added next and the mixture stirred. The organic layer was separated, washed with brine, dried ($Na_2SO_4$), filtered, and concentrated to dryness. The crude product was purified via TLC preparative plate using 5% methanol/methylene chloride as the solvent to obtain the desired compound I-(7A-80)c (88 mg, 42% from 4,6-dichloro-2-isopropylpyrimidin-5-ylamine) as a solid: +ESI MS (M+1) 373.2; $^1H$ NMR (400 MHz, $CDCl_3$) δ 7.80–6.90 (m, 8H), 2.76 (s, 3H).

Preparation of Intermediate 1-Benzyl-4-ethylaminopiperidine-4-carbonitrile (I-(7A-80)d)

I-(7A-80)d

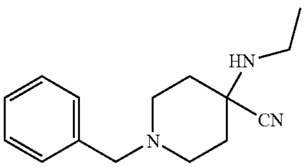

To a solution of 4-N-benzylpiperidone (5.69 g, 29.5 mmol) in ethanol (4.2 ml) cooled in an ice bath was added ethylamine hydrochloride (2.69 g, 32.3 mmol) in water (3 ml), keeping the internal temperature of the reaction below 10° C. A solution of KCN (2.04 g, 31.3 mmol) in water (7 ml) was added to reaction solution over 10 minutes keeping the internal temperature below 10° C. The reaction was then warmed to room temperature and stirred 18 hr. Isopropanol (10 ml) was added to the reaction mixture to give two distinct layers: lower colorless aqueous layer and an orange organic upper layer. The organic layer was separated and stirred with water (30 ml) for 30 minutes. The organic layer was separated (orange organic layer now the bottom layer) and the orange oil was diluted in $CH_2Cl_2$ (30 ml). The organic layer was washed with brine, dried ($Na_2SO_4$), filtered and concentrated, in vacuo, to give I-(7A-80)d as an orange oil (6.05 g, 84%): +APCI MS (M+1) 244.2; $^1H$ NMR (400 MHz, $CD_2Cl_2$) δ 7.32 (d, J=4.1 Hz, 4H), 7.29–7.23 (m, 1H), 3.54 (s, 2H), 2.81–2.76 (m, 2H), 2.75 (q, J=7.1 Hz, 2H), 2.35–2.29 (m, 2H), 2.01–1.98 (m, 2H), 1.74–1.68 (m, 2H), 1.14 (t, J=7.1 Hz, 3H).

Preparation of Intermediate 1-Benzyl-4-ethylaminopiperidine-4-carboxylic Acid Amide (I-(7A-80)e)

I-(7A-80)e

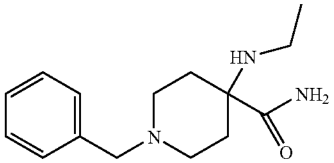

A solution of 1-benzyl-4-ethylaminopiperidine-4-carbonitrile 1-(7A-80)d (0.58 g, 2.38 mmol) in methylene chloride (2 ml) cooled in an ice bath was treated with $H_2SO_4$ (1.8 ml, 33 mmol), dropwise, while keeping the internal temperature below 20° C. The reaction was then warmed to room temperature and stirred for 19 hr. After stirring was discontinued, the thick pale orange $H_2SO_4$ bottom layer was separated, cooled in an ice bath and then carefully quenched with concentrated $NH_4OH$ keeping internal temperature below 55° C. The aqueous layer was extracted with methylene chloride (2×10 ml), the combined organic layers were washed with brine (20 ml), dried ($Na_2SO_4$), and then concentrated in vacuo to afford I-(7A-80)e as a pale orange oil that solidifies to a peach colored solid upon standing (0.54 g, 87%): +APCI MS (M+1) 262.2; $^1$H NMR (400 MHz, $CD_2Cl_2$) δ 7.34–7.30 (m, 4H), 7.29–7.21 (m, 1H), 7.16 (br s, 1H), 3.48 (s, 2H), 2.71–2.68 (m, 2H), 2.47 (q, J=7.0 Hz, 2H), 2.17–2.02 (m, 4H), 1.62–1.58 (m, 2H), 1.41 (br s, 1H), 1.09 (t, J=7.0 Hz, 3H).

Preparation of Intermediate 4-Ethylaminopiperidine-4-carboxylic Acid Amide (I-(7A-80)f)

I-(7A-80)f

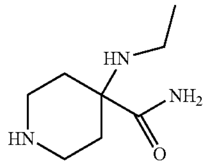

To a solution of 1-benzyl-4-ethylaminopiperidine-4-carboxylic acid amide I-(7A-80)e (7.39 g, 28.3 mmol) in methanol (100 ml) was added 20% $Pd(OH)_2$ on carbon (50% water; 1.48 g). The mixture was place on a Parr® shaker and was reduced (50 psi $H_2$) at room temperature overnight. The mixture was filtered through a pad of Celite®, and then concentrated to a colorless solid (4.84 g, quantitative): +ACPI MS (M+1) 172.2; $^1$H NMR (400 MHz, $CD_2Cl_2$) δ 2.89 (ddd, J=12.9, 8.7, 3.3 Hz, 2H), 2.75 (ddd, J=12.9, 6.6, 3.7 Hz, 2H), 2.45 (q, J=7.2 Hz, 2H), 1.95 (ddd, J=13.7, 8.3, 3.7 Hz, 2H), 1.55 (ddd, J=13.7, 6.6, 3.3 Hz, 2h), 1.08 (t, J=7.1 Hz, 3H).

Preparation of Intermediate 4-Chloro-N-[4-chloro-6-(4-chlorophenylamino)-pyrimidin-5-yl]-2-fluorobenzamide (I-(7A-91)a)

I-(7A-91)a

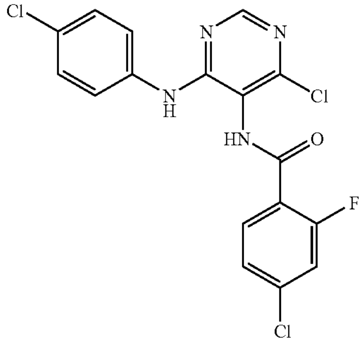

6-Chloro-N4-(4-chlorophenyl)-pyrimidine-4,5-diamine I-(1A-1)a (6.6 g, 26 mmol) in pyridine (30 ml) was cooled to 0° C. and to it was added 4-chloro-2-fluorobenzoyl chloride (5 g, 26 mmol). The reaction was then allowed to warm to ambient temperature overnight. The heterogeneous reaction was diluted with ethanol (50 ml) and the resulting solid collected by filtration. The solids were slurried in toluene, which was then removed under reduced pressure to remove residual ethanol. The solid was slurried in diethyl ether and then collected by filtration to give I-(7A-91)a (8.3 g, 78%): +ACPI MS (M+1) 409.0; $^1$H NMR (400 MHz, $CD_3OD$) δ 10.60 (s, 1H), 10.10 (s, 1H), 9.19 (s, 1H), 8.74 (t, J=8.1 Hz, 1H), 8.46–8.40 (m, 3H), 8.28 (dd, J=8.7, 2.1 Hz, 1H), 8.20 (d, J=8.7 Hz, 2H).

Preparation of Intermediate 6-chloro-8-(4-chloro-2-fluorophenyl)-9-(4-chloro-phenyl)-9H-purine (I-(7A-91)b)

I-(7A-91)b

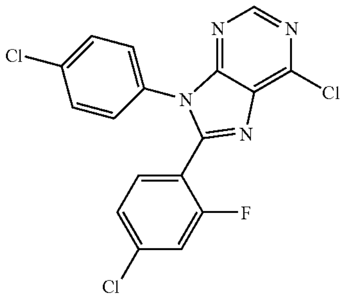

A suspension of 4-chloro-N-[4-chloro-6-(4-chlorophenylamino)-pyrimidin-5-yl]-2-fluorobenzamide I-(7A-91)a (8.3 g, 20 mmol) in $POCl_3$ (100 ml) was heated to reflux. The light brown reaction became homogeneous over 2 hours. After refluxing 3 hours, the reaction mixture was cooled and concentrated under reduced pressure to give a viscous oil. The residue was diluted with ethyl acetate and poured over ice/aqueous sodium bicarbonate. The organic layer was separated, washed with brine, dried ($Na_2SO_4$), and concentrated. Crystallization from diethyl ether afforded product I-(7A-91)b (5.8 g, 73%) as an off-white solid: +ESI MS (M+1) 393.0; $^1$H NMR (400 MHz, DMSO-$d_6$) δ 8.81 (s, 1H), 7.72 (t, J=8.1 Hz, 1H), 7.60–7.55 (m, 3H), 7.50–7.42 (m, 3H).

Preparation of Intermediate 1-Benzhydryl-3-isopropylaminoazetidine-3-carbonitrile (I-(7A-106)a)

I-(7A-106)a

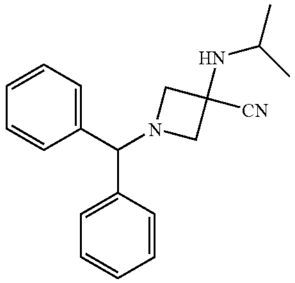

To a solution of 1-benzhydrylazetidin-3-one (3.20 g, 13.5 mmol) in ethanol (100 ml) cooled in an ice bath was added isopropylamine (1.26 ml, 14.8 mmol), followed by dropwise addition of concentrated aqueous HCl (1.23 ml, 14.8 mmol). After stirring for 15 minutes, a solution of NaCN (0.727 g, 14.8 mmol) in water (30 ml) was added to reaction mixture over 7 minutes. The reaction was then warmed to room temperature and stirred overnight. After concentrating the reaction to half volume, in vacuo, it was then extracted from saturated aqueous sodium bicarbonate with ethyl acetate. The combined organic layers were washed with brine, dried ($Na_2SO_4$), filtered and concentrated, in vacuo, to give an oil (3.17 g) that was 2:1 cyanohydrin to ketone as judged by $^1H$ NMR and LCMS. A solution of the residue in methanol (17 ml) was treated with isopropylamine (2.3 mmol, 27 mmol) and then acetic acid (1.6 ml, 27 mmol) at room temperature. After stirring for 30 minutes, solid NaCN (330 mg, 6.7 mmol) was added and the mixture was heated to reflux overnight. The reaction was concentrated, in vacuo, and then extracted from saturated aqueous sodium bicarbonate with ethyl acetate. The combined organic layers were washed with brine, dried ($Na_2SO_4$), filtered and concentrated, in vacuo, to give I-(7A-106)a as a dark foam (3.41 g, 83%): +ACPI MS (M+1) 306.4; $^1H$ NMR (400 MHz, $CD_2Cl_2$) δ 7.45–7.42 (m, 4H), 7.31–7.18 (m, 6H), 4.42 (s, 1H), 3.68 (d, J=8.3 Hz, 2H), 3.11 (septuplet, J=6.2 Hz, 1H), 3.07 (d, J=8.3 Hz, 2H), 1.01 (d, J=6.2 Hz, 6H).

Preparation of Intermediate 1-Benzhydryl-3-isopropylaminoazetidine-3-carboxylic Acid Amide (I-(7A-106)b)

I-(7A-106)b

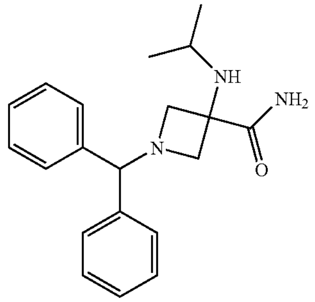

A solution of 1-benzhydryl-3-isopropylaminoazetidine-3-carbonitrile (I-(7A-106)a; 3.40 g, 11.1 mmol) in methylene chloride (25 ml) cooled in an ice bath was treated with $H_2SO_4$ (5.95 ml, 111 mmol), dropwise. After the reaction mixture was allowed to warm to room temperature and stir overnight, it was cooled in an ice bath and then carefully quenched with concentrated $NH_4OH$ to pH 11. The mixture was extracted with methylene chloride, the combined organic layers were dried ($Na_2SO_4$) and then concentrated, in vacuo, to afford a crude foam (3.3 g) that was then purified on a Biotage™ Flash 40M column using 0–2% methanol in methylene chloride as eluant to afford the title compound I-(7A-106)b (2.32 g, 64%) as a brown solid: +ESI MS (M+1) 324.4; $^1H$ NMR (400 MHz, $CD_3OD$) δ 7.40 (d, J=7.5 Hz, 4H), 7.24 (t, J=7.5 Hz, 4H), 7.15 (t, J=7.1 Hz, 2H), 4.46 (s, 1H), 3.53 (d, J=8.7 Hz, 2H), 3.06 (d, J=8.7 Hz, 2H), 2.90 (septuplet, J=6.4 Hz, 1H), 0.97 (d, J=6.6 Hz, 6H).

Preparation of Intermediate 3-Isopropylaminoazetidine-3-carboxylic Acid Amide, Hydrochloride Salt (I-(7A-106)c)

I-(7A-106)c

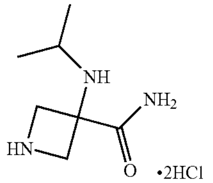

To a solution of 1-benzhydryl-3-isopropylaminoazetidine-3-carboxylic acid amide (I-(7A-106)b; 2.28 g, 7.05 mmol) in methanol (100 ml) was added 1M HCl in ether (14.8 ml, 14.8 mmol) and then water (10 ml). After the addition of 20% $Pd(OH)_2$ on carbon (60% water; 1.43 g), the mixture was placed on a Parr® shaker and then reduced (50 psi $H_2$) at room temperature overnight. The mixture was filtered through a pad of Celite®, and then concentrated, in vacuo. The residue was then concentrated, in vacuo, from toluene (2×), acetonitrile (2×) and then methanol to give I-(7A-106)c (1.59 g, 98%) as a tan solid: +ACPI MS (M+1) 158.1; $^1H$ NMR (400 MHz, $CD_3OD$) δ 4.71 (d, J=13.3 Hz, 2H), 4.60 (d, J=13.3 Hz, 2H), 3.49 (septuplet, J=6.6 Hz, 1H), 1.34 (d, J=6.6 Hz, 6H).

Preparation of Intermediate 1-Benzhydryl-3-benzylaminoazetidine-3-carbonitrile (I-(13A-9)a)

I-(13A-9)a

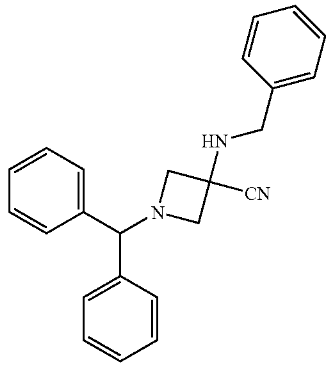

To a solution of 1-benzhydrylazetidin-3-one (3.3 g, 14 mmol) in methanol (35 ml) was added benzylamine (1.6 ml, 15 mmol) and then acetic acid (0.88 ml, 15 mmol) at room temperature. After stirring for 45 minutes, solid NaCN (0.76 g, 15 mmol) was added in portions over 2 minutes and the mixture was heated to reflux overnight. The reaction, which now contained a precipitate, was cooled and then stirred at room temperature. The solid were collected by vacuum filtration, rinsed with a small volume of cold methanol, and then dried, in vacuo, to give I-(13A-9)a as a solid (3.56 g, 72%): +ACPI MS (M+1) 354.4; $^1H$ NMR (400 MHz, $CD_3OD$) δ 7.40 (d, J=7.5 Hz, 4H), 7.35 (d, J=7.5 Hz, 2H), 7.31–7.20 (m, 7H), 7.16 (t, J=7.3 Hz, 2H), 4.44 (s, 1H), 3.76 (s, 2H), 3.48 (d, J=8.3 Hz, 2H), 3.05 (d, J=8.3 Hz, 2H).

Preparation of Intermediate 1-Benzhydryl-3-benzylaminoazetidine-3-carboxylic Acid Amide (I-(13A-9)b)

I-(13A-9)b

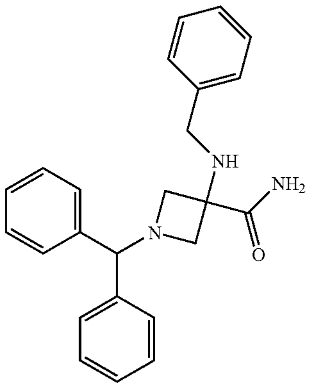

A solution of 1-benzhydryl-3-benzylaminoazetidine-3-carbonitrile I-(13A-9)a (3.45 g, 9.76 mmol) in methylene chloride (55 ml) cooled in an ice bath was treated with $H_2SO_4$ (8.1 ml, 0.15 mol), dropwise. After the reaction mixture was allowed to warm to room temperature and stir overnight, it was cooled in an ice bath and then carefully quenched with concentrated $NH_4OH$ to pH 10. The mixture was extracted with methylene chloride and then the combined organic layers were washed with brine, dried ($Na_2SO_4$) and concentrated, in vacuo, to afford a brown solid. Trituration of this material from hexanes/diethyl ether afforded a light tan solid which were collected by vacuum filtration, washed with additional hexanes and dried, in vacuo, to give I-(13A-9)b (3.34 g, 92%): +ESI MS (M+1) 372.4; $^1H$ NMR (400 MHz, $CD_3OD$) δ 7.41 (d, J=7.5 Hz, 4H), 7.35 (d, J=7.5 Hz, 2H), 7.31–7.22 (m, 7H), 7.16 (t, J=7.7 Hz, 2H), 4.50 (s, 1H), 3.60 (s, 2H), 3.48 (d, J=8.3 Hz, 2H), 3.16 (d, J=8.3 Hz, 2H).

Preparation of Intermediate 1-Benzhydryl-3-(benzylethylamino)-azetidine-3-carboxylic Acid Amide, Hydrochloride Salt (I-(13A-9)c)

I-(13A-9)c

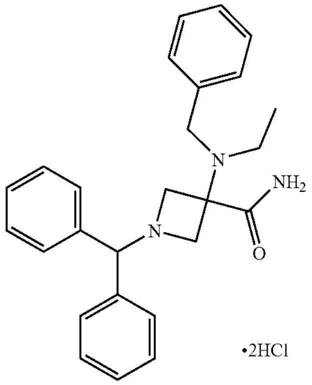

•2HCl

A suspension of 1-benzhydryl-3-benzylaminoazetidine-3-carboxylic acid amide I-(13A-9)b (3.06 g, 8.24 mmol) in methanol (80 ml) cooled in an ice bath was treated with acetic acid (2.4 ml, 41 mmol), sodium acetate (6.8 g, 82 mmol) and acetaldehyde (1.8 ml, 41 mmol). After stirring for 10 minutes, $NaCNBH_3$ (6.24 mg, 9.9 mmol) was added, portionwise. After stirring for 45 minutes, the mixture was then allowed to warm to room temperature and stir overnight. The reaction was concentrated, in vacuo, and the residue then extracted from saturated aqueous sodium bicarbonate with ethyl acetate, the combined organic layers were washed with brine, dried ($MgSO_4$), and then concentrated, in vacuo, to afford the crude product (3.8 g): +ACPI MS (M+1) 400.5; $^1H$ NMR (400 MHz, $CD_2Cl_2$) δ 7.41–7.37 (m, 6H), 7.29–7.22 (m, 6H), 7.20–7.12 (m, 3H), 4.44 (s, 1H), 3.74 (s, 2H), 3.47 (d, J=8.3 Hz, 2H), 3.12 (d, J=8.3 Hz, 2H), 2.56 (q, J=7.2 Hz, 2H), 0.85 (t, J=7.1 Hz, 3H).

For purification, a solution of the free base in methanol (75 ml) was treated with 1M HCl in diethyl ether (21 ml), dropwise over 5 minutes. After stirring for 20 minutes, the mixture was concentrated under reduced pressure followed by concentration from addition methanol (2×) and then ethanol. The residue was then suspended and stirred in isopropanol (3 ml) while diethyl ether (50 ml) was slowly added. After stirring for 45 minutes, the solids were then isolated by vacuum filtration, were washed with ether and dried, in vacuo, to provide I-(13A-9)c (4.4 g, quantitative): +ACPI MS (M+1) 400.5; $^1H$ NMR (400 MHz, $CD_3OD$) δ 7.55–7.25 (br m, 15H), 5.76 (br s, 1H), 4.21 (br s, 4H), 3.93 (v br s, 2H), 1.02 (br s, 3H).

Preparation of Intermediate 1-Benzhydryl-3-ethylaminoazetidine-3-carbonitrile (I-(13A-9)d)

I-(13A-9)d

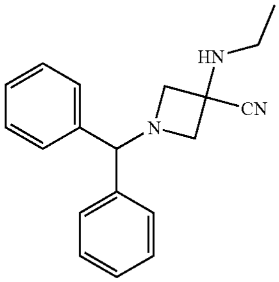

To a mixture of 1-benzhydrylazetidin-3-one (9.5 g, 40 mmol) in methanol (30 ml) was added ethylamine hydrochloride (4.2 g, 52 mmol) and then acetic acid (3.0 ml, 52 mmol) at room temperature. After stirring for 15 minutes, solid KCN (3.4 g, 52 mmol) was added and the homogeneous mixture was heated at 60° C., overnight. The reaction was cooled and then concentrated, in vacuo. The residue was then extracted from saturated aqueous sodium bicarbonate with ethyl acetate, the combined organic layers were washed with brine, dried ($MgSO_4$), and then concentrated, in vacuo, to afford I-(13A-9)d as a colorless solid (11.7 g, quantitative): +ES MS (M+1) 292.2; $^1H$ NMR (400 MHz, $CD_3OD$) δ 7.42 (d, J=7.5 Hz, 4H), 7.26 (t, J=7.5 Hz, 4H), 7.17 (t, J=7.3 Hz, 2H), 4.47 (s, 1H), 3.54 (d, J=8.3 Hz, 2H), 3.25 (d, J=8.3 Hz, 2H), 2.61 (s, J=7.2 Hz, 2H), 1.11 (t, J=7.3 Hz, 3H).

Preparation of Intermediate 1-Benzhydryl-3-ethylaminoazetidine-3-carboxylic Acid Amide (I-(13A-9)e)

I-(13A-9)e

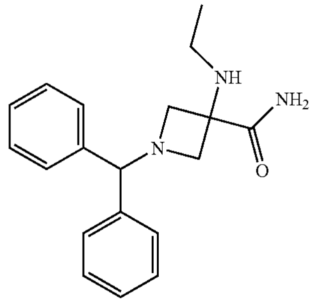

A vigorously stirred solution of 1-benzhydryl-3-ethylaminoazetidine-3-carbonitrile (I-(13A-9)d; 11.7 g, 40 mmol) in methylene chloride (150 ml) cooled in an ice bath was treated with $H_2SO_4$ (22 ml, 0.4 mol), dropwise. After the reaction mixture was allowed to warm to room temperature and stir overnight, it was cooled in an ice bath and then carefully quenched with concentrated $NH_4OH$ to pH 11. The off-white solids that formed during the quench were collected by vacuum filtration. The aqueous mixture was then extracted with methylene chloride, the combined organic layers were washed with brine, dried ($Na_2SO_4$) and then concentrated, in vacuo, to afford additional solids. The combined solids were stirred for 1 hour in ethyl acetate (150 mL) and then collected by vacuum filtration to give I-(13A-9)e (9.2 g, 74%) as a solid: +ES MS (M+1) 310.2; $^1$H NMR (400 MHz, $CD_3OD$) δ 7.41 (d, J=7.1 Hz, 4H), 7.25 (t, J=7.5 Hz, 4H), 7.16 (t, J=7.5 Hz, 2H), 4.49 (s, 1H), 3.44 (d, J=8.3 Hz, 2H), 3.11 (d, J=8.3 Hz, 2H), 2.47 (q, J=7.1 Hz, 2H), 1.10 (t, J=7.3 Hz, 3H).

Preparation of Intermediate 3-Ethylaminoazetidine-3-carboxylic Acid Amide, Hydrochloride Salt (I-(13A-9)f)

I-(13A-9)f

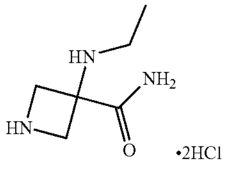

•2HCl

To a solution of 1-benzhydryl-3-(benzylethylamino)-azetidine-3-carboxylic acid amide hydrochloride salt (I-(13A-9)c; 0.66 g, 1.4 mmol) in methanol (25 ml) was added 20% $Pd(OH)_2$ on carbon (30% water; 0.13 g). The mixture was placed on a Parr® shaker and then reduced (45 psi $H_2$) at room temperature overnight. The mixture was diluted with methanol (200 ml) filtered through a 0.45 μm filter disk, and then concentrated to a solid. The residue was triturated from diethyl ether, collected by vacuum filtration, washed with ether and then dried, in vacuo, to afford I-(13A-9)f (298 mg, 98%): +ACPI MS (M+1) 144.1; $^1$H NMR (400 MHz, $CD_2Cl_2$) δ 4.56 (s, 4H), 3.00 (q, J=7.2 Hz, 2H), 1.36 (t, J=7.1 Hz, 3H).

Alternatively, a solution of 1-benzhydryl-3-ethylaminoazetidine-3-carboxylic acid amide (I-2A-1g; 9.2 g, 30 mmol) in methanol (150 ml) at 0° C. was added 1 M HCl in ether (75 ml, 75 mmol). The mixture was concentrated to ⅔ volume to remove the ether, in vacuo, and then methanol was added to bring the reaction volume to 150 mL. This was repeated a second time. After the addition of 20% $Pd(OH)_2$ on carbon (50% water; 2.3 g), the mixture was placed on a Parr® shaker and then reduced (45 psi $H_2$) at room temperature overnight. The mixture was diluted with methanol (350 ml) filtered through Celite®, rinsing with additional methanol. The methanol fractions were filtered through a 0.45 μm filter disk, and then concentrated under reduced pressure to give a solid residue that was triturated from diethyl ether, collected by vacuum filtration, washed with ether and then dried, in vacuo, to afford I-(13A-9)f (6.3 g, 91%) as a tan solid.

Preparation of Intermediate 1-[9-(4-Chlorophenyl)-8-(2,4-dichlorophenyl)-9H-purin-6-yl]-ethanone (I-(15A-1)a)

I-(15A-1)a

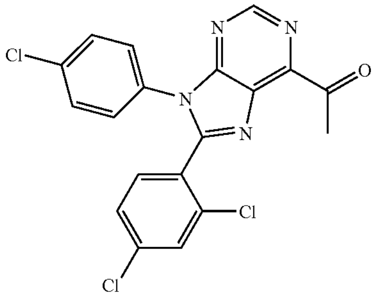

A solution of 6-chloro-9-(4-chlorophenyl)-8-(2,4-dichlorophenyl)-9H-purine I-(1A-1)d (202 mg, 0.49 mmol) and tetrakis(triphenylphosphine) palladium(0) (60 mg, 0.049 mmol) in dimethylformamide (1.5 ml) was degassed and to it was added tributyl-(1-ethoxyvinyl)-stannane (250 μl, 0.74 mmol). The reaction mixture was heated to 100° C. until completed as shown by TLC. A solution of 2:1 of $H_2O$/conc. HCl (1.5 ml) was added to the reaction mixture and the heating continued for 1 hour. The reaction was diluted with ethyl acetate and washed with water. The organic layers were combined, dried ($Na_2SO_4$), filtered, and concentrated to dryness. The crude material was purified via TLC preparative plate using 30% ethyl acetate/hexanes as the solvent to afford the desired product I-(15A-1)a (50 mg, 25%): +ESI MS (M+1) 417.3; $^1$H NMR (400 MHz, $CDCl_3$) δ 9.11 (s, 1H), 7.58 9 (d, J=8.7 Hz, 1H), 7.43–7.30 (m, 4H), 7.21 (d, J=8.7 Hz, 2H), 2.92 (s, 3H).

Preparation of Intermediate 9-(4-Chlorophenyl)-8-(2,4-dichlorophenyl)-9H-purine-6-carbonitrile (I-(16A-1)a)

I-(16A-1)a

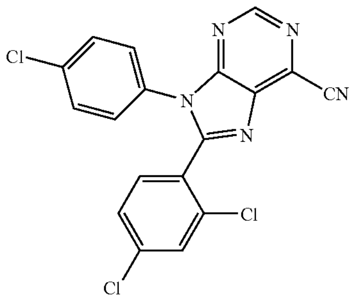

6-Chloro-9-(4-chlorophenyl)-8-(2,4-dichlorophenyl)-9H-purine I-(1A-1)d (200 mg, 0.49 mmol) was dissolved in acetonitrile (5 ml) and stirred at 0° C. Tetrabutylammonium cyanide (236 mg, 0.98 mmol) and 1,4-diaza-bicyclo[2.2.2]octane (173 mg, 1.5 mmol) were added to the reaction mixture and stirring was continued at 0° C. for 3 hours. The reaction mixture was concentrated under reduced pressure and then purified by flash chromatography using 30% ethyl acetate/hexanes as the eluant to obtain the desired product I-(16A-1)a (215 mg, quant): +ESI MS (M+1) 400.2; $^{1}$H NMR (400 MHz, $CDCl_3$) δ 9.09 (s, 1H), 7.57 (d, J=8.7 Hz, 1H), 7.45–7.39 (m, 4H), 7.21 (d, J=8.7 Hz, 2H).

Preparation of Intermediate C-[9-(4-Chlorophenyl)-8-(2,4-dichlorophenyl)-9H-purin-6-yl]-methylamine (I-(16A-1)b)

I-(16A-1)b

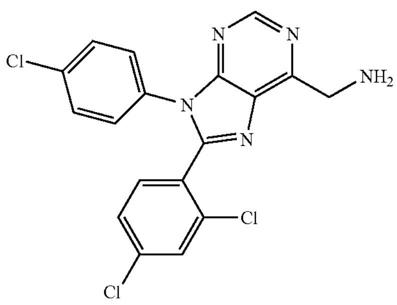

9-(4-Chlorophenyl)-8-(2,4-dichlorophenyl)-9H-purine-6-carbonitrile I-(16A-1)a (110 mg, 0.27 mmol) was dissolved in methylene chloride (0.9 ml) and the solution cooled to −78° C. Diisobutyl aluminum hydride (1 M in methylene chloride; 590 μl, 0.59 mmol) was added dropwise to the reaction mixture and stirring continued at −78° C. until TLC indicated the starting material had been consumed. Methanol (100 μl) was added to the mixture to quench the reaction and the cooling bath was removed. The reaction mixture was extracted with ethyl acetate from 1 M HCl. The organic layer was back-extracted with 1M HCl and the aqueous layers combined. The aqueous layers were then brought to a basic pH with sodium hydroxide and extracted with ethyl acetate. The organic layers were combined, dried ($Na_2SO_4$), filtered, and evaporated to dryness to afford the desired compound I-(16A-1)b: +ESI MS (M+1) 404.4; $^{1}$H NMR (400 MHz, $CD_3OD$) δ 8.92 (s, 1H), 7.69 (d, J=8.3 Hz, 1H), 7.57 (d, J=1.7 Hz, 1H), 7.53–7.43 (m, 3H), 7.36 (d, J=8.3 Hz, 2H), 4.40 (s, 2H).

Preparation of Intermediate N4-(4-Chlorophenyl)-6-pyrrolidin-1-yl-pyrimidine-4,5-diamine (I-(17A-1)a)

I-(17A-1)a

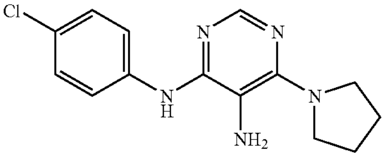

6-Chloro-N4-(4-chlorophenyl)-pyrimidine-4,5-diamine I-(1A-1)a (114 mg, 0.45 mmol) and pyrrolidine (1 ml, excess) were combined and heated with stirring at 100° C. for 2 hours. The reaction mixture was diluted with saturated $NaHCO_3$ solution and extracted with ethyl acetate. The organic layers were combined, dried ($Na_2SO_4$), filtered, and evaporated to dryness to yield the desired compound I-(17A-1)a (131 mg, quantitative) as an orange-brown solid: +ESI MS (M+1) 290.3; $^{1}$H NMR (500 MHz, $CD_3OD$) δ 7.85 (s, 1H), 7.45 (d, J=8.8 Hz, 2H), 7.26 (d, J=8.8 Hz, 2H), 3.63 (m, 4H), 1.96 (m, 4H).

Preparation of Intermediate 2-Benzhydryl-5-benzyl-2,5,7-triazaspiro[3.4]oct-6-en-8-one (I-(29A-6)a)

I-(29A-6)a

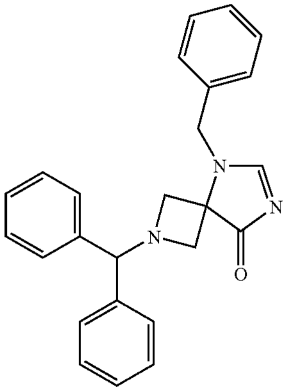

N,N-Dimethylformamide dimethyl acetal (16 ml, 121 mmol) was combined with 1-benzhydryl-3-benzylaminoazetidine-3-carboxylic acid amide (I-(13A-9)b; 3.03 g, 8.16 mmol) and heated to reflux. After 4 hours, the suspension was cooled and extracted from saturated aqueous $NaHCO_3$ with ethyl acetate. The combined extracts were dried ($Na_2SO_4$), and concentrated, in vacuo, to the crude solid (3.50 g). Purification of the residue on a Biotage™ Flash 40M column using 0–3% methanol in methylene chloride as eluant afforded I-(29A-6)a as a yellowish solid (1.92 g, 62%): +ES MS (M+1) 382.3; $^{1}$H NMR (400 MHz, $CD_3OD$) δ 8.66 (s, 1H), 7.59 (d, J=7.1 Hz, 2H), 7.49–7.11 (m, 13H), 5.12 (s, 2H), 4.44 (s, 1H), 3.31 (d, J=9.6 Hz, 2H), 3.20 (d, J=9.6 Hz, 2H).

Preparation of Intermediate 2,5,7-Triazaspiro[3.4,]octan-8-one, Hydrochloride Salt (I-(29A-6)b)

I-(29A-6)b

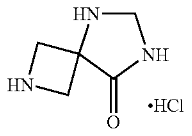

To a solution of 2-benzhydryl-5-benzyl-2,5,7-triazaspiro[3.4]oct-6-en-8-one (I-(29A-6)a; 1.83 g, 4.80 mmol) in methanol/methylene chloride was added excess 1 M HCl in diethyl ether (10 ml). After stirring for 10 minutes, the solvent was removed, in vacuo, and the resultant hydrochloride salt dissolved in methanol (50 ml). After the addition of 20% $Pd(OH)_2$ on carbon (50% water; 1.1 g), the mixture was placed on a Parr® shaker and then reduced (50 psi $H_2$) at room temperature for 22 hours. The reaction was filtered through a 0.45 μM disk, and then concentrated, in vacuo, to give a gummy solid. This material was triturated from methanol to afford I-(29A-6)b (450 mg, 47%) as a tan solid: +ACPI MS (M+1) 127.9; $^1$H NMR (400 MHz, $CD_3OD$) δ 4.51 (s, 2H), 4.41–4.33 (m, 4H).

Preparation of Intermediate 1-Benzhydryl-3-methylaminoazetidine-3-carbonitrile (I-(29A-7)a)

I-(29A-7)a

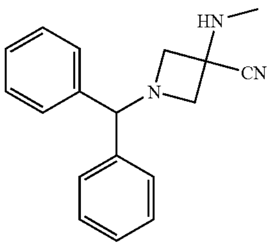

To a solution of 1-benzhydrylazetidin-3-one (2.13 g, 8.98 mmol) in methanol (17 ml) was added methylamine hydrochloride (1.21 g, 18.0 mmol) and then acetic acid (1.03 ml, 18.0 mmol) at room temperature. After stirring for 5 minutes, solid KCN (1.17 g, 18.0 mmol) was added and the mixture was heated to 60° C. for 19 hours. The reaction was cooled; the solid product was collected by vacuum filtration, rinsed with methanol, and then dried, in vacuo, to afford I-(29A-7)a as a colorless solid (2.50 g, quantitative): +ES MS (M+1) 278.3; $^1$H NMR (400 MHz, $CD_2Cl_2$) δ 7.43 (d, J=7.5 Hz, 4H), 7.29 (t, J=7.5 Hz, 4H), 7.23 (t, J=7.3 Hz, 2H), 4.45 (s, 1H), 3.55 (d, J=7.5 Hz, 2H), 3.15 (d, J=7.1 Hz, 2H), 2.40 (s, 3H).

Preparation of Intermediate 1-Benzhydryl-3-methylaminoazetidine-3-carboxylic Acid Amide (I-(29A-7)b)

I-(29A-7)b

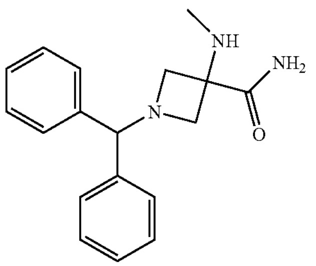

A vigorously stirred solution of 1-benzhydryl-3-methylaminoazetidine-3-carbonitrile (I-(29A-7)a; 2.10 g, 7.57 mmol) in methylene chloride (25 ml) cooled in an ice bath was treated with $H_2SO_4$ (4.0 ml, 76 mmol), dropwise. After the reaction mixture was allowed to warm to room temperature and stir overnight, it was cooled in an ice bath and then carefully quenched with concentrated $NH_4OH$ to pH 11. The mixture was extracted with methylene chloride, the combined organic layers were dried ($Na_2SO_4$) and then concentrated, in vacuo, to afford I-(29A-7)b (1.2 g, 54%) as an off-white solid: +ES MS (M+1) 296.3; $^1$H NMR (400 MHz, $CD_3OD$) δ 7.41 (d, J=7.5 Hz, 4H), 7.25 (t, J=7.5 Hz, 4H), 7.16 (t, J=7.1 Hz, 2H), 4.48 (s, 1H), 3.41 (d, J=8.7 Hz, 2H), 3.09 (d, J=8.7 Hz, 2H), 2.24 (s, 3H).

Preparation of Intermediate 2-Benzhydryl-5-methyl-2,5,7-triazaspiro[3.4]oct-6-en-8-one (I-(29A-7)c)

I-(29A-7)c

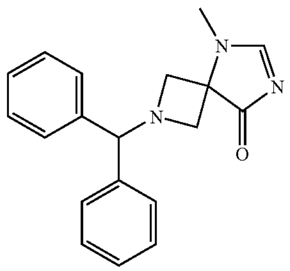

N,N-Dimethylformamide dimethyl acetal (1.1 ml, 8.3 mmol) was combined with 1-benzhydryl-3-methylaminoazetidine-3-carboxylic acid amide (I-(29A-7)b; 153 mg, 0.52 mmol) and heated to reflux. After 3 hours, the suspension was cooled and extracted from saturated aqueous $NaHCO_3$ with ethyl acetate. The combined extracts were dried ($Na_2SO_4$), and concentrated, in vacuo, to afford I-(29A-7)c as a solid (152 mg, 96%): +ES MS (M+1) 306.3; $^1$H NMR (400 MHz, $CD_3OD$) δ 8.42 (s, 1H), 7.47 (d, J=7.5 Hz, 4H), 7.27 (t, J=7.5 Hz, 4H), 7.17 (t, J=7.5 Hz, 2H), 4.57 (s, 1H), 3.58 (s, 3H), 3.55 (d, J=10.0 Hz, 2H), 3.34 (d, J=10.0 Hz, 2H).

Preparation of Intermediate 5-Methyl-2,5,7-triaza-spiro[3.4]octan-8-one, Hydrochloride Salt (I-(29A-7)d)

I-(29A-7)d

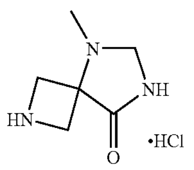

To a solution of 2-benzhydryl-5-methyl-2,5,7-triazaspiro[3.4]oct-6-en-8-one (I-(29A-7)c; 189 mg, 0.619 mmol) in methanol (30 ml) was added 1 M HCl in diethyl ether (1.3 ml). After the addition of 20% $Pd(OH)_2$ on carbon (50% water; 95 mg), the mixture was placed on a Parr® shaker and then reduced (50 psi $H_2$) at room temperature for 5 hours. The reaction was filtered through a 0.45 μM disk, and then concentrated, in vacuo, to give a solid. Trituration from diethyl ether afforded I-(29A-7)d (124 mg, 94%) as an off-white solid: +ACPI MS (M+1) 142.0; $^1$H NMR (400 MHz, $CD_3OD$) δ 4.38 (d, J=12.0 Hz, 2H), 4.17 (s, 2H), 4.13 (d, J=12.5 Hz, 2H), 2.71 (s, 3H).

EXAMPLE 1

Preparation of 9-(4-Chlorophenyl)-8-(2,4-dichlorophenyl)-6-isopropoxy-9H-purine (1A-1)

1A-1

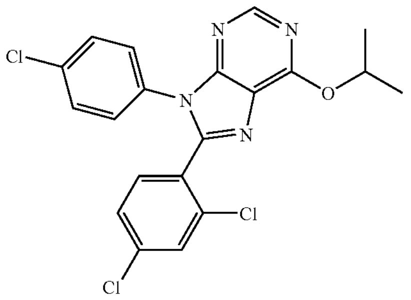

Sodium (7 mg, 0.3 mmol) was dissolved in isopropanol (1 ml) and to it was added 6-chloro-9-(4-chlorophenyl)-8-(2,4-dichlorophenyl)-9H-purine I-(1A-1)d (30 mg, 0.07 mmol). After stirring at room temperature overnight, the reaction mixture was evaporated to dryness and extracted into ethyl acetate from saturated aqueous $NaHCO_3$ solution. The organic layers were combined, dried ($Na_2SO_4$), filtered, and concentrated to dryness. The crude residue was purified on a TLC preparative plate using 4% methanol/methylene chloride as the solvent to yield title compound 1A-1. A solution of the material in methylene chloride was treated with excess 1 N HCl in diethyl ether, stirred, evaporated to dryness, and then triturated in diethyl ether to afford the hydrochloride salt of compound 1A-1 (8 mg, 26%): +ESI MS (M+1) 433.4; $^1$H NMR (400 MHz, $CD_3OD$) δ 8.50 (s, 1H), 7.64 (d, J=8.3 Hz, 1H), 7.55 (d, J=1.7 Hz, 1H), 7.49–7.45 (3H), 7.34 (d, J=9.1 Hz, 2H), 5.73 (septuplet, J=6.2 Hz, 1H), 1.48 (d, J=6.2 Hz, 6H).

The compounds listed in Table 1 below were prepared using procedures analogous to those described above for the synthesis of Compound 1A-1 using the appropriate starting materials which are available commercially, prepared using preparations well-known to those skilled in the art, or prepared in a manner analogous to routes decribed above for other intermediates. The compounds listed below were isolated initially as the free base and then generally converted to their corresponding hydrochloride salt for testing.

TABLE 1

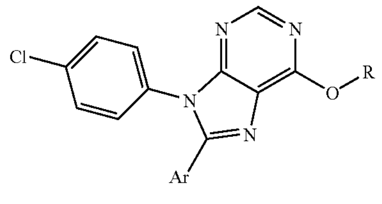

| Example No. | Ar | —OR | MS (M + H)$^+$ |
|---|---|---|---|
| 1A-2 | 2,4-dichlorophenyl | —OMe | 405.4 |
| 1A-3 | 2,4-dichlorophenyl | —OEt | 419.6 |
| 1A-4 | 2,4-dichlorophenyl | —O-n-Pr | 433.4 |
| 1A-5 | 2,4-dichlorophenyl | —O-n-Bu | 447.0 |

EXAMPLE 2

Preparation of 6-tert-Butoxy-9-(4-chlorophenyl)-8-(2,4-dichlorophenyl)-9H-purine (2A-1)

2A-1

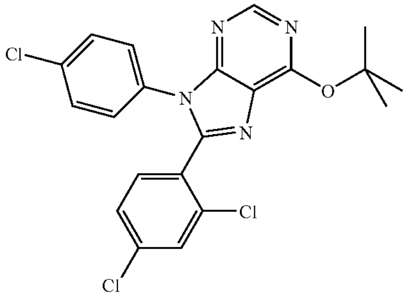

6-Chloro-9-(4-chlorophenyl)-8-(2,4-dichlorophenyl)-9H-purine I-(1A-1)d, potassium tert-butoxide (20 mg, 0.15 mmol) and tetrahydrofuran (1 ml) were combined and stirred overnight at ambient temperature. The reaction mixture was concentrated to dryness and the residue was extracted into ethyl acetate from saturated aqueous $NaHCO_3$ solution. The organic layers were combined, dried ($Na_2SO_4$), filtered, and evaporated to dryness. The crude product was purified by chromatography on a preparative TLC plate using 4% methanol/methylene chloride as the solvent to give title compound 2A-1 as a yellow oil: +ESI MS (M+1) 447.5; $^1$H NMR (400 MHz, $CD_3OD$) δ 8.48 (s, 1H), 7.64 (d, J=8.3 Hz, 1H), 7.55 (d, J=2.1 Hz, 1H), 7.49–7.44 (m, 3H), 7.34 (d, J=9.1 Hz, 2H), 1.77 (s, 9H).

EXAMPLE 3

Preparation of 6-(1-Benzhydrylazetidin-3-yloxy)-9-(4-chlorophenyl)-8-(2,4-dichlorophenyl)-9H-purine (3A-1)

3A-1

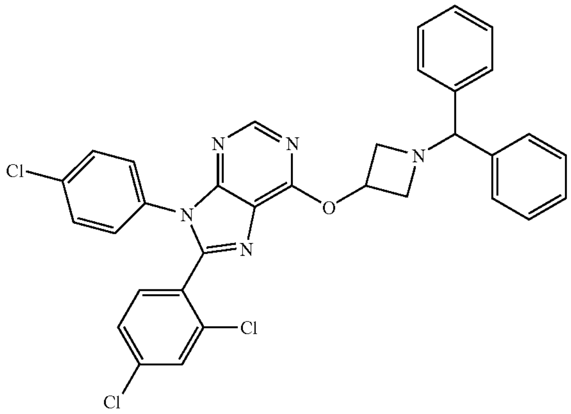

To a tetrahydrofuran (1 ml) solution of 6-chloro-9-(4-chlorophenyl)-8-(2,4-dichlorophenyl)-9H-purine I-(1A-1)d (30 mg, 0.073 mmol) and 1-benzhydrylazetidin-3-ol (53 mg, 0.22 mmol) was added potassium tertbutoxide (24 mg, 0.22 mmol). The combined reagents were stirred overnight at ambient temperature. The reaction mixture was concentrated to dryness and the residue was extracted into ethyl acetate from saturated $NaHCO_3$ solution. The organic layers were combined, dried ($Na_2SO_4$), filtered, and evaporated to dryness. The crude product was purified by chromatography on a preparative TLC plate using 4% methanol/methylene chloride as the solvent to give title compound 3A-1 as a yellow oil. A solution of the material in methylene chloride was treated with excess 1 N HCl in diethyl ether, stirred, evaporated to dryness, and then triturated in diethyl ether to afford the hydrochloride salt of compound 3A-1 (14 mg, 31%): +ESI MS (M+1) 612.2; $^1$H NMR (400 MHz, $CD_3OD$) δ 8.51 (s, 1H), 7.65–7.30 (m, 17H), 5.85–5.77 (br m, 2H), 4.75–4.60 (br m, 2H), 4.55–4.30 (br m, 2H).

The compounds listed in Table 2 below were prepared using procedures analogous to those described above for the synthesis of Compound 3A-1 using the appropriate starting materials which are available commercially, prepared using preparations well-known to those skilled in the art, or prepared in a manner analogous to routes decribed above for other intermediates. The compounds listed below were isolated initially as the free base and then generally converted to their corresponding hydrochloride salt for testing.

TABLE 2

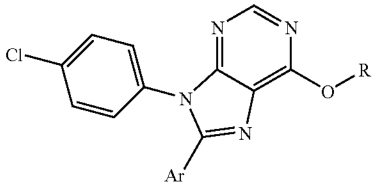

| Example No. | Ar | —OR | MS (M + H)$^+$ |
|---|---|---|---|
| 3A-2 | 2,4-dichlorophenyl | 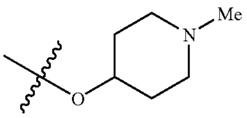 | 488.4 |
| 3A-3 | 2,4-dichlorophenyl | 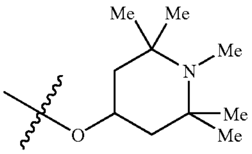 | 544.4 |
| 3A-4 | 2,4-dichlorophenyl | 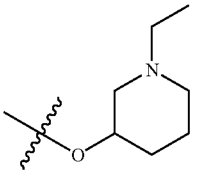 | 502.4 |

TABLE 2-continued
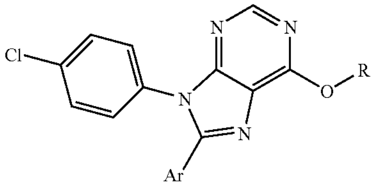
| Example No. | Ar | —OR | MS (M + H)+ |
|---|---|---|---|
| 3A-5 | 2,4-dichlorophenyl | 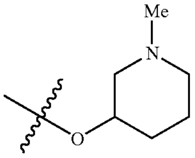 | 488.4 |
| 3A-6 | 2,4-dichlorophenyl | 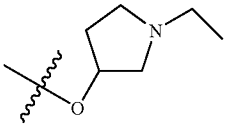 | 488.4 |
| 3A-7 | 2,4-dichlorophenyl | 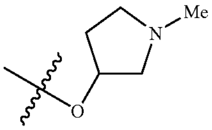 | 474.0 |
| 3A-8 | 2,4-dichlorophenyl | 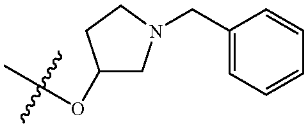 | 550.2 |
| 3A-9 | 2,4-dichlorophenyl | 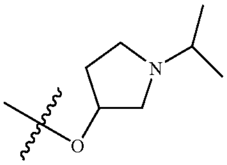 | 502.4 |
| 3A-10 | 2,4-dichlorophenyl | 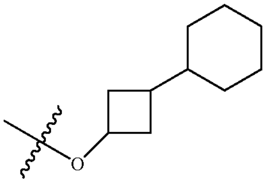 | 528.0 |
| 3A-11 | 2,4-dichlorophenyl | 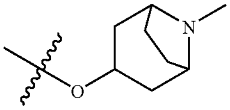 | 514.8 |

EXAMPLE 4

Preparation of 9-(4-Chlorophenyl)-8-(2,4-dichlorophenyl)-6-tetrahydrofuran-2-ylmethoxy)-9H-purine (4A-1)

4A-1

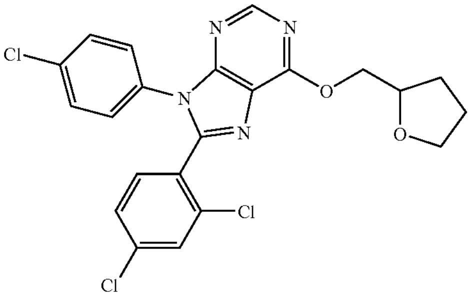

9-(4-Chlorophenyl)-8-(2,4-dichlorophenyl)-9H-purin-6-ol I-(1A-1)c (100 mg, 0.255 mmol), 2-bromomethyl-tetrahydrofuran (42 mg, 0.255 mmol), and cesium carbonate (83 mg, 0.26 mmol) were combined in dimethylformamide (5 ml) and heated to 100° C. overnight. The reaction mixture was diluted with ethyl acetate and washed with brine. The organic layer was dried ($Na_2SO_4$), filtered, and evaporated to dryness. The crude material was purified on a preparative TLC plate using 75% ethyl acetate/hexanes as the eluant to yield title compound 4A-1 (20 mg, 16%); $^1H$ NMR (400 MHz, $CD_3OD$): δ 8.52 (s, 1H), 7.64 (d, J=8.3 Hz, 1H), 7.49 (d, J=2.1 Hz, 1H), 7.50–7.44 (m, 3H), 7.34 (d, J=8.7 Hz, 2H), 4.68 (d, J=5.0 Hz, 2H), 4.39 (m, 1 H), 3.91 (m, 1 H), 3.79 (m, 1H), 2.20–1.83 (m, 4H). A solution of the material in methylene chloride was treated with 4 M HCl/dioxane, evaporated to dryness then further dried with high vacuum to yield the hydrochloride salt of compound 4A-1: +ACPI MS (M+1) 475.2.

The compounds listed in Table 3 below were prepared using procedures analogous to those described above for the synthesis of Compound 4A-1 using the appropriate starting materials which are available commercially, prepared using preparations well-known to those skilled in the art, or prepared in a manner analogous to routes decribed above for other intermediates. The compounds listed below were isolated initially as the free base and then generally converted to their corresponding hydrochloride salt for testing.

TABLE 3

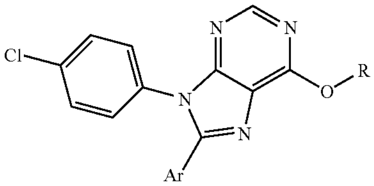

| Example No. | Ar | —OR | MS $(M + H)^+$ |
|---|---|---|---|
| 4A-2 | 2,4-dichlorophenyl | 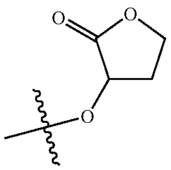 | 475.1 |

TABLE 3-continued

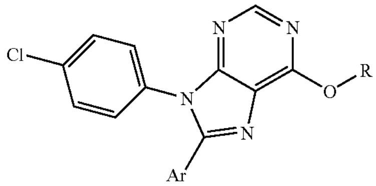

| Example No. | Ar | —OR | MS $(M + H)^+$ |
|---|---|---|---|
| 4A-3 | 2,4-dichlorophenyl | 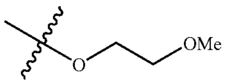 | 449.1 |
| 4A-4 | 2,4-dichlorophenyl | 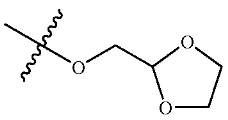 | 477.2 |
| 4A-5 | 2,4-dichlorophenyl | 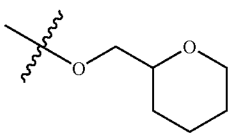 | 489.2 |
| 4A-6 | 2,4-dichlorophenyl | 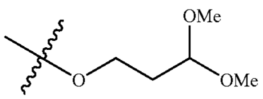 | 493.2 |
| 4A-7 | 2-chlorophenyl | —OEt | 385.2 |
| 4A-8 | 2-chlorophenyl | —OMe | 371.2 |
| 4A-9 | 2-chlorophenyl | 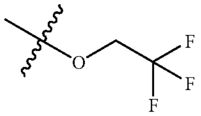 | 439.2 |

EXAMPLE 5

Preparation of 9-(4-Chlorophenyl)-8-(2,4-dichlorophenyl)-6-(2,2,2-trifluoro-ethoxy)-9H-purine (5A-1)

5A-1

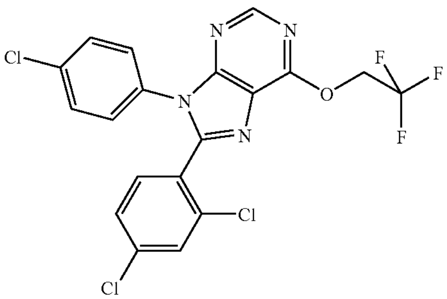

Potassium tert-butoxide (1 M in THF; 0.73 ml, 0.73 mmol) and 2,2,2-trifluoroethanol (2 ml) were stirred at room temperature and to this mixture was added 6-chloro-9-(4-chlorophenyl)-8-(2,4-dichlorophenyl)-9H-purine I-(1A-1)d (100 mg, 0.24 mmol). The reaction mixture was stirred at room temperature for 3 days then quenched with $H_2O$ and diluted with chloroform. The organic layer was washed with brine, dried ($Na_2SO_4$), filtered, and concentrated under reduced pressure. The crude product was purified by preparative TLC using 20% ethyl acetate/hexanes as the eluant to give title compound 5A-1 (20 mg, 17%): +ACPI MS (M+1) 473.1; $^1H$ NMR: (400 MHz, $CD_3OD$): δ 8.58 (s, 1H), 7.64 (d, 1H), 7.57 (d, 1H), 7.50–7.41 (m, 3H), 7.36 (d, 2H), 5.23 (q, 2H).

EXAMPLE 6

Preparation of 9-[4-Chlorophenyl)-8-(2,4-dichlorophenyl)-9H-purin-6-yl]-cyclohexylamine (6A-1)

6A-1

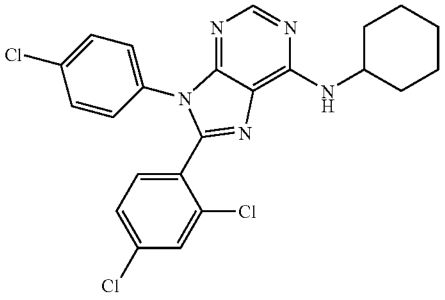

6-Chloro-9-(4-chlorophenyl)-8-(2,4-dichlorophenyl)-9H-purine I-(1A-1)d (30 mg, 0.07 mmol) and cyclohexylamine (0.3 ml) were combined in ethanol (0.5 ml) and heated at 60° C. for 30 minutes. The reaction mixture was concentrated under a stream of $N_2$ and then extracted into ethyl acetate from saturated $NaHCO_3$ solution. The organic layers were combined, dried ($Na_2SO_4$), filtered, evaporated to dryness, and then purified by preparative TLC using 25% ethyl acetate/hexanes as eluant to obtain title compound 6A-1. A solution of the material in methylene chloride was treated with excess 1 N HCl in diethyl ether, stirred, evaporated to dryness, and then triturated in diethyl ether to afford the hydrochloride salt of compound 6A-1 (9.8 mg, 57%) as a solid: +ESI MS (M+1) 472.6; $^1H$ NMR: (500 MHz, $CD_3OD$): δ 8.40 (s, 1H), 7.66–7.60 (m, 2H), 7.38–7.35 (m, 3H), 7.53–7.50 (d, J=8.8 Hz, 2H), 3.90 (br m, 1H), 2.12 (br d, J=11.9 Hz, 2H), 1.94 (br d, J=13.0 Hz, 2H), 1.78 (br d, J=14.5 Hz, 1H), 1.62–1.23 (m, 5H).

The compounds listed in Table 4 below were prepared using procedures analogous to those described above for the synthesis of Compound 6A-1 using the appropriate starting materials which are available commercially, prepared using preparations well-known to those skilled in the art, or prepared in a manner analogous to routes decribed above for other intermediates. The compounds listed below were isolated initially as the free base and then generally converted to their corresponding hydrochloride salt for testing.

TABLE 4

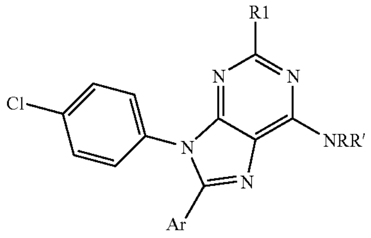

| Ex. No. | Ar | R1 | —NRR' | MS (M + H)$^+$ |
|---|---|---|---|---|
| 6A-2 | 2,4-dichlorophenyl | —H | 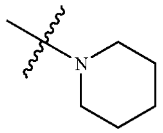 | 458.5 |
| 6A-3 | 2,4-dichlorophenyl | —H | 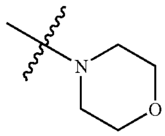 | 460.5 |
| 6A-4 | 2,4-dichlorophenyl | —H | 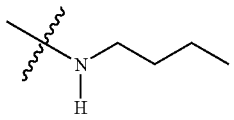 | 446.5 |
| 6A-5 | 2,4-dichlorophenyl | —H | 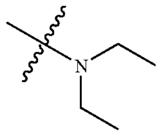 | 446.5 |
| 6A-6 | 2,4-dichlorophenyl | —H | 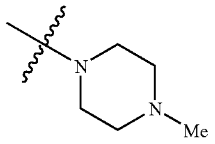 | 473.6 |

EXAMPLE 7

Preparation of 1-[9-(4-Chloro-phenyl)-8-(2,4-dichloro-phenyl)-9H-purin-6-yl]-piperidine-4-carboxylic acid Ethyl Ester (7A-1)

7A-1

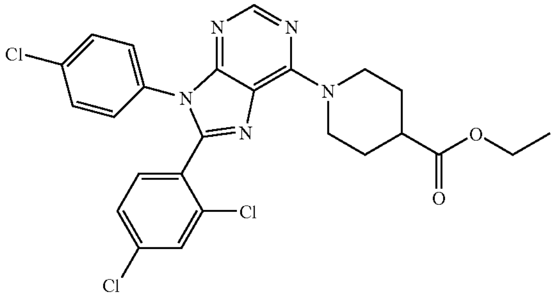

6-chloro-9-(4-chlorophenyl)-8-(2,4-dichlorophenyl)-9H-purine I-(1A-1)d (30 mg, 0.07 mmol), piperidine-4-carboxylic acid ethyl ester (34 mg, 0.22 mmol), and triethylamine (20 μl, 0.29 mmol) were combined in ethanol (1 ml) and heated at 70° C. for 2 hours. The reaction mixture was concentrated under a stream of $N_2$ and then extracted into ethyl acetate from saturated $NaHCO_3$ solution. The organic layers were combined, dried ($Na_2SO_4$), filtered, evaporated to dryness, and then purified by preparative TLC using 4% methanol in methylene chloride as eluant to obtain title compound 7A-1. A solution of the material in methylene chloride was treated with excess 1 N HCl in diethyl ether, stirred and evaporated to dryness to afford the hydrochloride salt of compound 7A-1 (24 mg, 65%) as a solid: +ESI MS (M+1) 530.1; $^1$H NMR (400 MHz, $CD_3OD$) δ 8.35 (s, 2H), 7.60 (d, J=8.3 Hz, 1H), 7.56 (d, J=2.1 Hz, 1H), 7.50–7.45 (m, 3H), 7.34 (d, J=8.7 Hz, 2H), 4.15 (q, J=7.1 Hz, 2H), 3.68 (v br s, 2H), 2.85 (m, 1H), 2.16 (m, 2H), 1.89 (m, 2H), 1.25 (t, J=7.1 Hz, 3H).

The compounds listed in Table 5 below were prepared using procedures analogous to those described above for the synthesis of Compound 7A-1 using the appropriate starting materials which are available commercially, prepared using preparations well-known to those skilled in the art, or prepared in a manner analogous to routes decribed above for other intermediates. The compounds listed below were isolated initially as the free base and then generally converted to their corresponding hydrochloride salt for testing.

TABLE 5

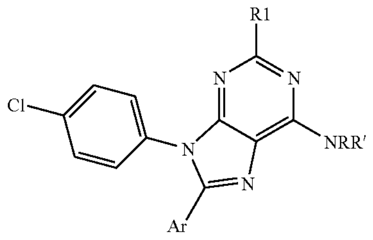

| Ex. No. | Ar | R1 | —NRR' | MS (M + H)$^+$ |
|---|---|---|---|---|
| 7A-2 | 2,4-dichlorophenyl | —H | 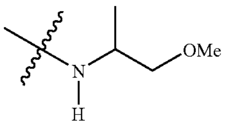 | 462.0 |
| 7A-3 | 2,4-dichlorophenyl | —H | 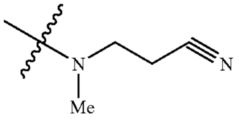 | 457.1 |
| 7A-4 | 2,4-dichlorophenyl | —H | 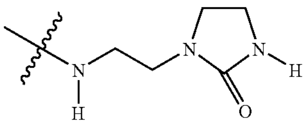 | 502.5 |
| 7A-5 | 2,4-dichlorophenyl | —H | 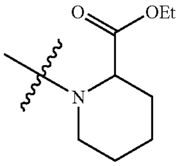 | 530.4 |
| 7A-6 | 2,4-dichlorophenyl | —H | 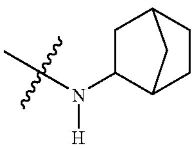 | 484.4 |
| 7A-7 | 2,4-dichlorophenyl | —H | 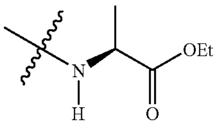 | 490.8 |

TABLE 5-continued
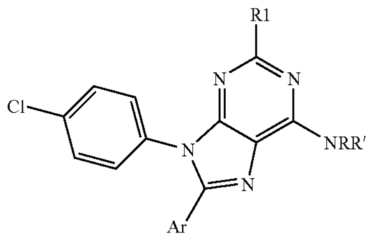
| Ex. No. | Ar | R1 | —NRR' | MS (M + H)+ |
|---|---|---|---|---|
| 7A-8 | 2,4-dichlorophenyl | —H | 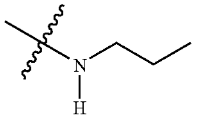 | 432.0 |
| 7A-9 | 2,4-dichlorophenyl | —H | 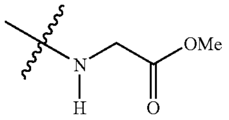 | 462.0 |
| 7A-10 | 2,4-dichlorophenyl | —H | 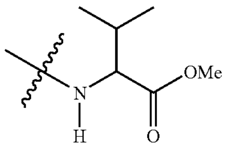 | 504.8 |
| 7A-11 | 2,4-dichlorophenyl | —H | 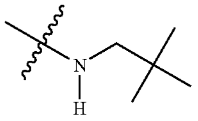 | 460.0 |
| 7A-12 | 2,4-dichlorophenyl | —H | 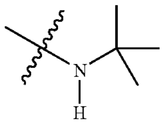 | 446.0 |
| 7A-13 | 2,4-dichlorophenyl | —H | 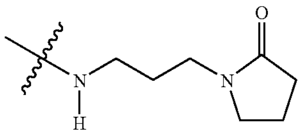 | 515.2 |
| 7A-14 | 2,4-dichlorophenyl | —H | 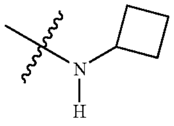 | 444.0 |
| 7A-15 | 2,4-dichlorophenyl | —H | 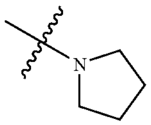 | 444.6 |
| 7A-16 | 2,4-dichlorophenyl | —H | 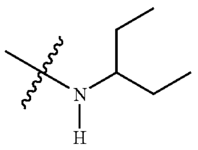 | 460.0 |

TABLE 5-continued
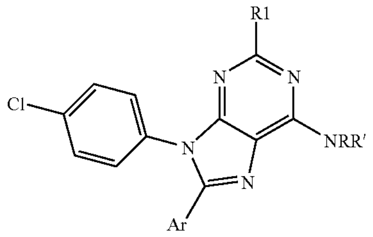
| Ex. No. | Ar | R1 | —NRR' | MS (M + H)+ |
|---|---|---|---|---|
| 7A-17 | 2,4-dichlorophenyl | —H | 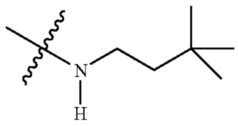 | 474.4 |
| 7A-18 | 2,4-dichlorophenyl | —H | 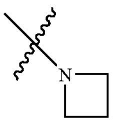 | 430.0 |
| 7A-19 | 2,4-dichlorophenyl | —H | 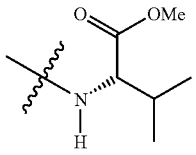 | 504.4 |
| 7A-20 | 2,4-dichlorophenyl | —H | 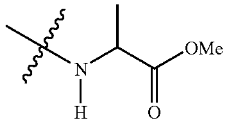 | 476.0 |
| 7A-21 | 2,4-dichlorophenyl | —H | 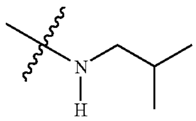 | 446.0 |
| 7A-22 | 2,4-dichlorophenyl | —H | 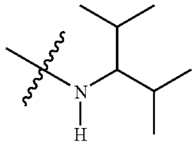 | 488.8 |
| 7A-23 | 2,4-dichlorophenyl | —H | 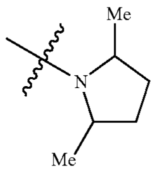 | 472.4 |
| 7A-24 | 2,4-dichlorophenyl | —H | 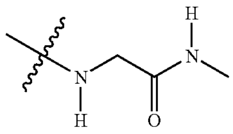 | 461.5 |

TABLE 5-continued
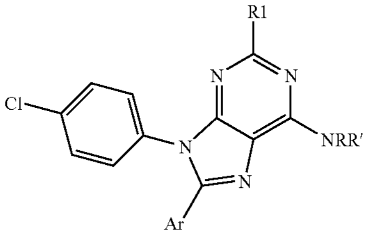
| Ex. No. | Ar | R1 | —NRR' | MS (M + H)+ |
|---|---|---|---|---|
| 7A-25 | 2,4-dichlorophenyl | —H | 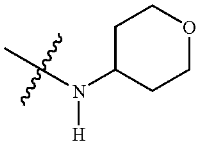 | 474.4 |
| 7A-26 | 2,4-dichlorophenyl | —H | 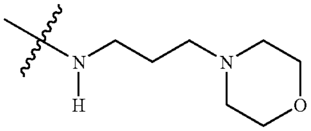 | 517.2 |
| 7A-27 | 2,4-dichlorophenyl | —H | 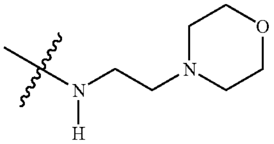 | 503.2 |
| 7A-28 | 2,4-dichlorophenyl | —H | 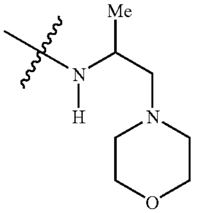 | 517.2 |
| 7A-29 | 2,4-dichlorophenyl | —H | 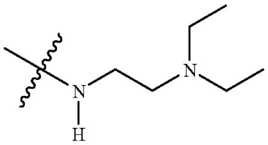 | 489.6 |
| 7A-30 | 2,4-dichlorophenyl | —H | 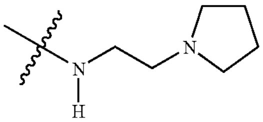 | 487.2 |
| 7A-31 | 2,4-dichlorophenyl | —H | 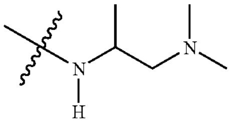 | 475.2 |
| 7A-32 | 2,4-dichlorophenyl | —H | 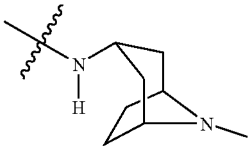 | 513.2 |

TABLE 5-continued
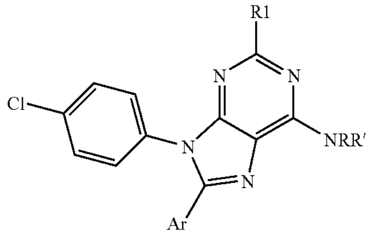
| Ex. No. | Ar | R1 | —NRR' | MS (M + H)+ |
|---|---|---|---|---|
| 7A-33 | 2,4-dichlorophenyl | —H | 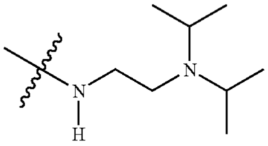 | 517.2 |
| 7A-34 | 2,4-dichlorophenyl | —H | 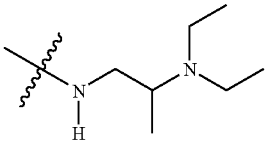 | 503.2 |
| 7A-35 | 2,4-dichlorophenyl | —H | 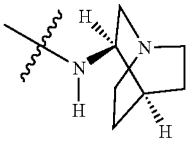 | 499.6 |
| 7A-36 | 2,4-dichlorophenyl | —H | 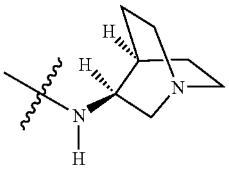 | 499.2 |
| 7A-37 | 2,4-dichlorophenyl | —H | 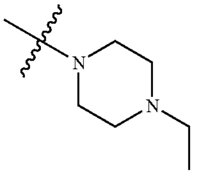 | 487.2 |
| 7A-38 | 2,4-dichlorophenyl | —H | 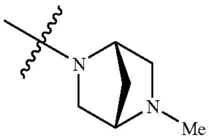 | 485.2 |
| 7A-39 | 2,4-dichlorophenyl | —H | 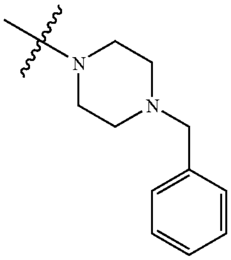 | 549.2 |

TABLE 5-continued
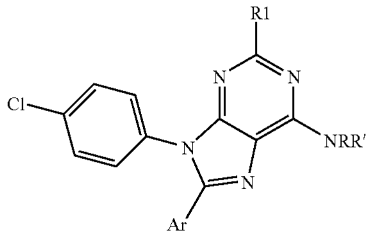
| Ex. No. | Ar | R1 | —NRR' | MS (M + H)+ |
|---|---|---|---|---|
| 7A-40 | 2,4-dichlorophenyl | —H | 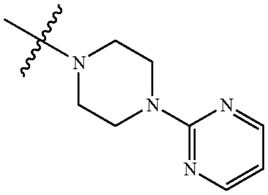 | 537.2 |
| 7A-41 | 2,4-dichlorophenyl | —H | 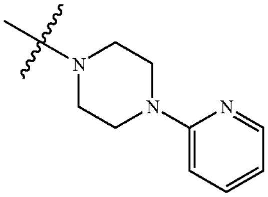 | 536.4 |
| 7A-42 | 2,4-dichlorophenyl | —H | 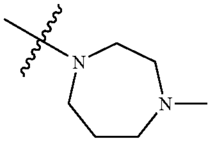 | 487.2 |
| 7A-43 | 2,4-dichlorophenyl | —H | 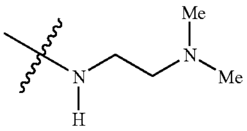 | 461.9 |
| 7A-44 | 2,4-dichlorophenyl | —H | 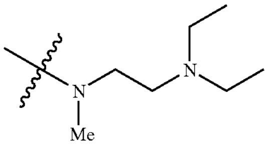 | 503.2 |
| 7A-45 | 2,4-dichlorophenyl | —H | 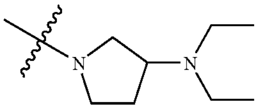 | 515.2 |
| 7A-46 | 2,4-dichlorophenyl | —H | 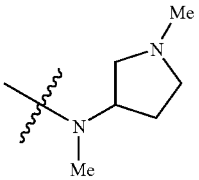 | 487.2 |

TABLE 5-continued
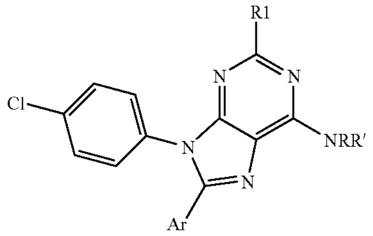
| Ex. No. | Ar | R1 | —NRR' | MS (M + H)+ |
|---|---|---|---|---|
| 7A-47 | 2,4-dichlorophenyl | —H | 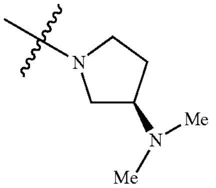 | 487.2 |
| 7A-48 | 2,4-dichlorophenyl | —H | 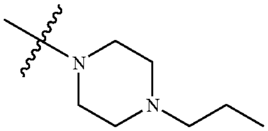 | 501.2 |
| 7A-49 | 2,4-dichlorophenyl | —H | 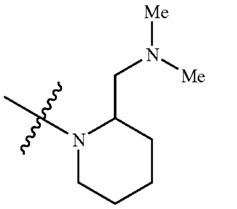 | 515.2 |
| 7A-50 | 2,4-dichlorophenyl | —H | 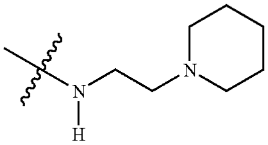 | 501.2 |
| 7A-51 | 2,4-dichlorophenyl | —H | 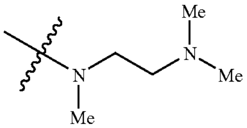 | 475.2 |
| 7A-52 | 2,4-dichlorophenyl | —H | 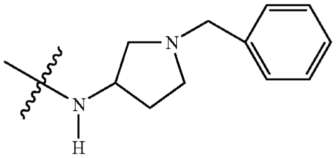 | 549.2 |
| 7A-53 | 2,4-dichlorophenyl | —H | 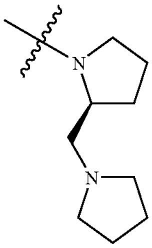 | 527.1 |

TABLE 5-continued
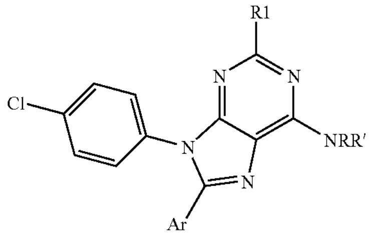
| Ex. No. | Ar | R1 | —NRR' | MS (M + H)+ |
|---|---|---|---|---|
| 7A-54 | 2,4-dichlorophenyl | —H | 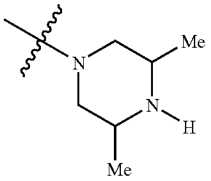 | 487.4 |
| 7A-55 | 2,4-dichlorophenyl | —H | 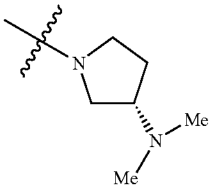 | 487.5 |
| 7A-56 | 2,4-dichlorophenyl | —H | 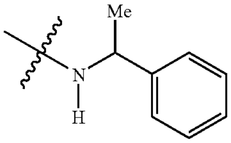 | 494.0 |
| 7A-57 | 2,4-dichlorophenyl | —H | 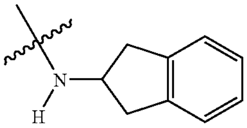 | 506.4 |
| 7A-58 | 2,4-dichlorophenyl | —H | 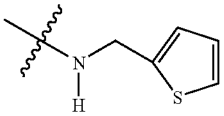 | 486.4 |
| 7A-59 | 2,4-dichlorophenyl | —H | 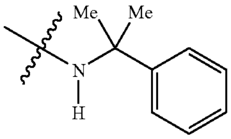 | 508.0 |
| 7A-60 | 2,4-dichlorophenyl | —H | 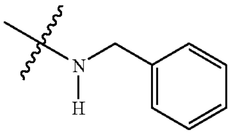 | 480.9 |
| 7A-61 | 2,4-dichlorophenyl | —H | 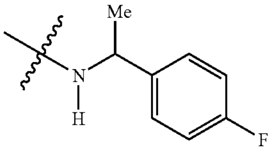 | 512.4 |

TABLE 5-continued
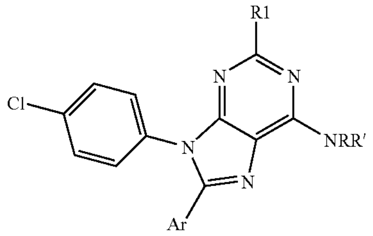
| Ex. No. | Ar | R1 | —NRR' | MS (M + H)+ |
|---|---|---|---|---|
| 7A-62 | 2,4-dichlorophenyl | —H | 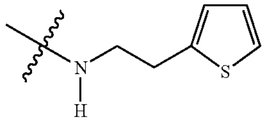 | 500.4 |
| 7A-63 | 2,4-dichlorophenyl | —H | 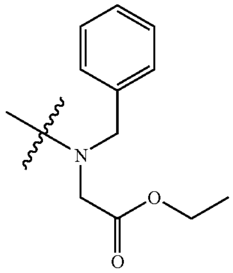 | 566.0 |
| 7A-64 | 2,4-dichlorophenyl | —H | 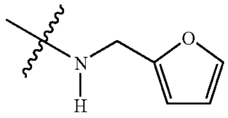 | 470.0 |
| 7A-65 | 2,4-dichlorophenyl | —H | 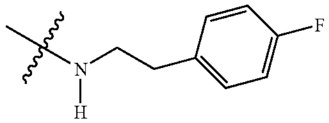 | 512.4 |
| 7A-66 | 2,4-dichlorophenyl | —H | 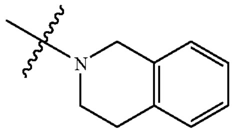 | 506.4 |
| 7A-67 | 2,4-dichlorophenyl | —H | 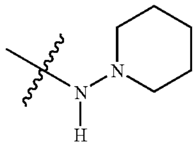 | 473.6 |
| 7A-68 | 2,4-dichlorophenyl | —H | 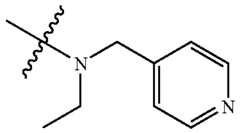 | 509.5 |
| 7A-69 | 2,4-dichlorophenyl | —H | 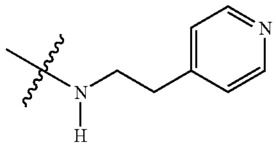 | 495.9 |

TABLE 5-continued
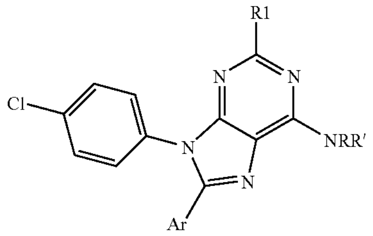
| Ex. No. | Ar | R1 | —NRR' | MS (M + H)+ |
|---|---|---|---|---|
| 7A-70 | 2,4-dichlorophenyl | —H | 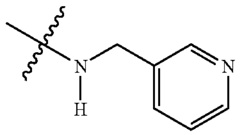 | 481.2 |
| 7A-71 | 2,4-dichlorophenyl | —H | 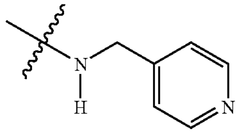 | 481.9 |
| 7A-72 | 2,4-dichlorophenyl | —H | 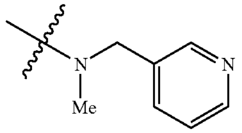 | 495.1 |
| 7A-73 | 2,4-dichlorophenyl | —H | 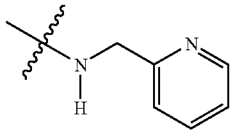 | 481.2 |
| 7A-74 | 2,4-dichlorophenyl | —H | 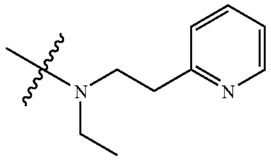 | 523.2 |
| 7A-75 | 2,4-dichlorophenyl | —H | 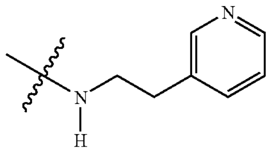 | 495.3 |
| 7A-76 | 2,4-dichlorophenyl | —H | 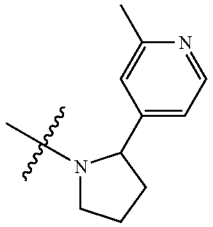 | 535.2 |

TABLE 5-continued
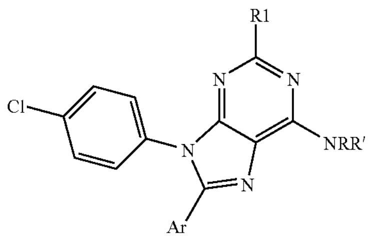
| Ex. No. | Ar | R1 | —NRR' | MS (M + H)$^+$ |
| --- | --- | --- | --- | --- |
| 7A-77 | 2,4-dichlorophenyl | —H | 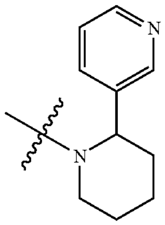 | 535.2 |
| 7A-78 | 2,4-dichlorophenyl | —H | 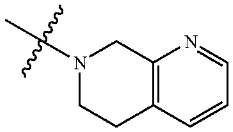 | 507.6 |
| 7A-79 | 2,4-dichlorophenyl | —H | 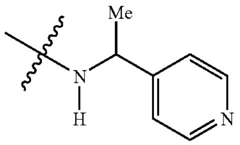 | 495.9 |
| 7A-80 | 2-fluorophenyl | —$CH_3$ | 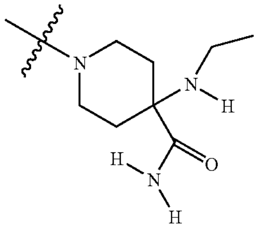 | 508.3 |
| 7A-81 | 2,4-dichlorophenyl | —H | 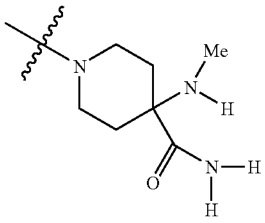 | 530.1 |
| 7A-82 | 2,4-dichlorophenyl | —H | 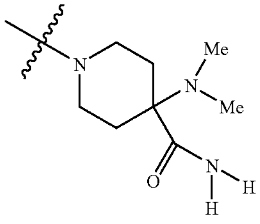 | 544.1 |

TABLE 5-continued
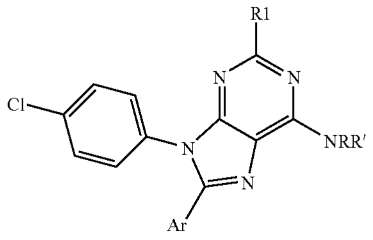
| Ex. No. | Ar | R1 | —NRR' | MS (M + H)+ |
|---|---|---|---|---|
| 7A-83 | 2,4-dichlorophenyl | —H | 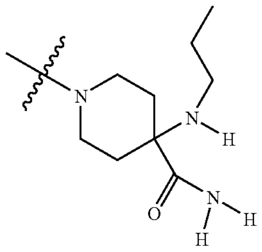 | 558.1 |
| 7A-84 | 2-fluorophenyl | —H | 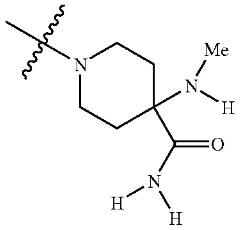 | 480.2 |
| 7A-85 | 2-fluorophenyl | —H | 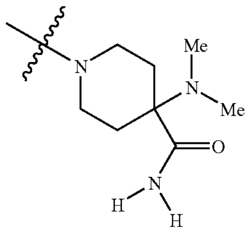 | 494.2 |
| 7A-86 | 2-fluorophenyl | —H | 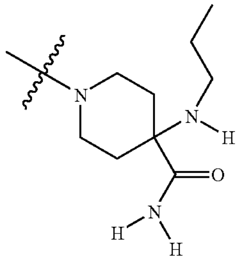 | 508.2 |
| 7A-87 | 2-chlorophenyl | —H | 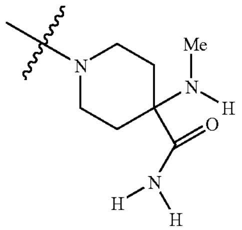 | 496.1 |

TABLE 5-continued
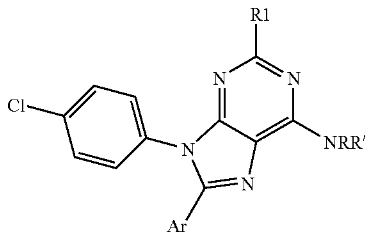
| Ex. No. | Ar | R1 | —NRR' | MS (M + H)+ |
|---|---|---|---|---|
| 7A-88 | 2-chlorophenyl | —H | 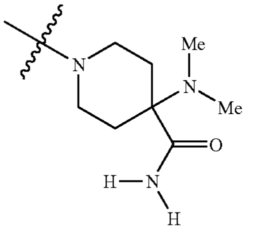 | 510.2 |
| 7A-89 | 2-chlorophenyl | —H | 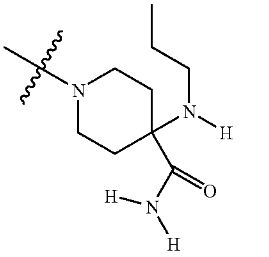 | 524.2 |
| 7A-90 | 2-chlorophenyl | —H | 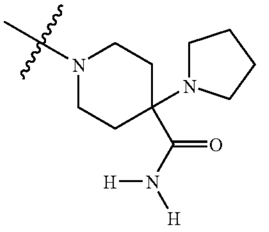 | 536.2 |
| 7A-91 | 4-chloro-2-fluorophenyl | —H | 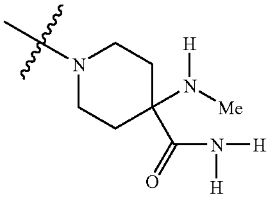 | 514.1 |
| 7A-92 | 4-chloro-2-fluorophenyl | —H | 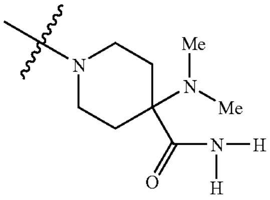 | 528.1 |

TABLE 5-continued
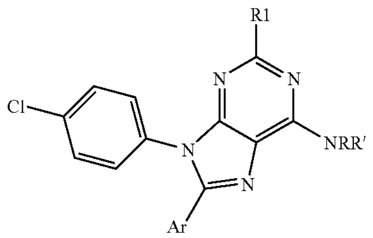
| Ex. No. | Ar | R1 | —NRR' | MS (M + H)+ |
|---|---|---|---|---|
| 7A-93 | 4-chloro-2-fluorophenyl | —H | 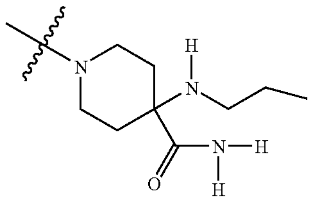 | 542.1 |
| 7A-94 | 2,4-dichlorophenyl | —H | 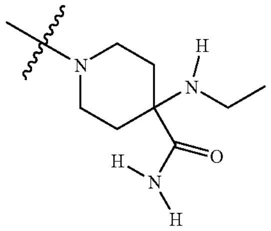 | 544.2 |
| 7A-95 | 2-fluorophenyl | —H | 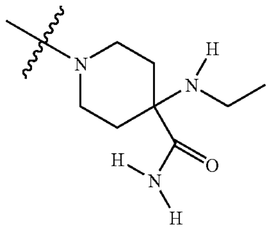 | 494.1 |
| 7A-96 | 2-chlorophenyl | —H | 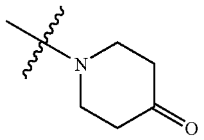 | 438.1 |
| 7A-97 | 2,4-dichlorophenyl | —H | 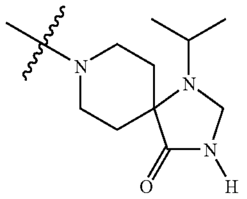 | 570.1 |
| 7A-98 | 2,4-dichlorophenyl | —H | 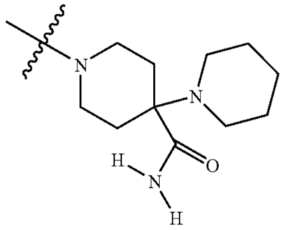 | 584.1 |

TABLE 5-continued
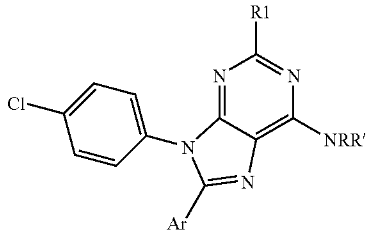
| Ex. No. | Ar | R1 | —NRR' | MS (M + H)+ |
|---|---|---|---|---|
| 7A-99 | 4-chloro-2-fluorophenyl | —H | 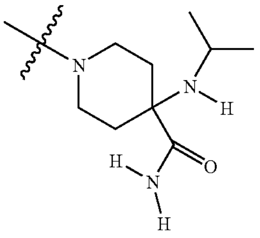 | 542.2 |
| 7A-100 | 4-chloro-2-fluorophenyl | —H | 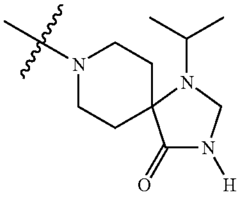 | 554.2 |
| 7A-101 | 4-chloro-2-fluorophenyl | —H | 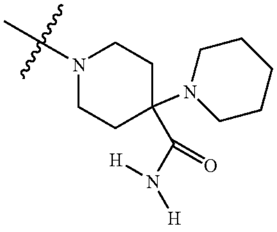 | 568.3 |
| 7A-102 | 2,4-dichlorophenyl | —H | 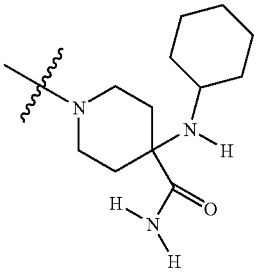 | 598.2 |
| 7A-103 | 2-fluorophenyl | —H | 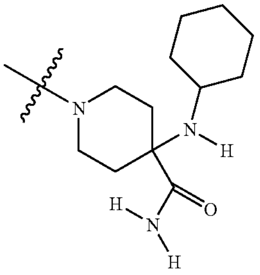 | 548.3 |

TABLE 5-continued
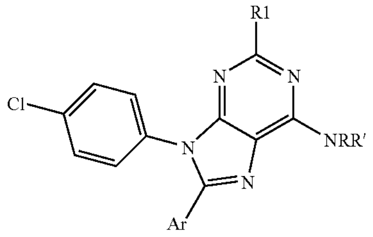
| Ex. No. | Ar | R1 | —NRR' | MS (M + H)+ |
|---|---|---|---|---|
| 7A-104 | 4-chloro-2-fluorophenyl | —H | 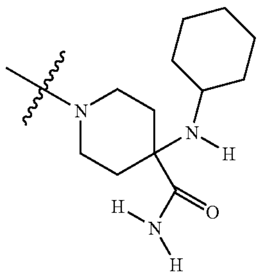 | 582.2 |
| 7A-105 | 4-chloro-2-fluorophenyl | —H | 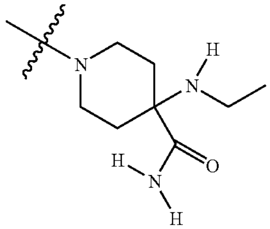 | 528.2 |
| 7A-106 | 2-chlorophenyl | —H | 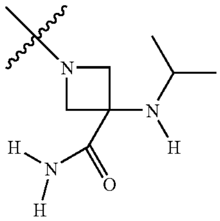 | 496.1 |
| 7A-107 | 2-chlorophenyl | —H | 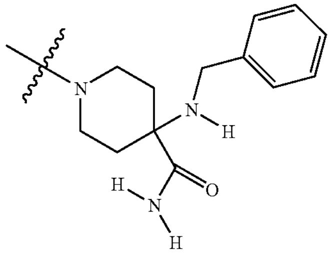 | 572.2 |
| 7A-108 | 2-chlorophenyl | —H | 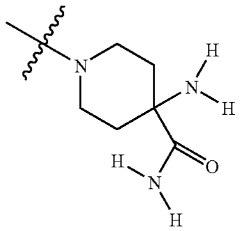 | 482.2 |

TABLE 5-continued

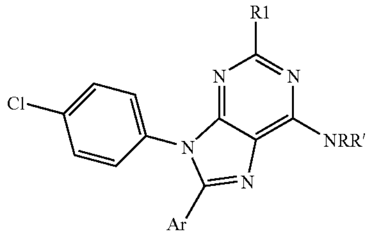

| Ex. No. | Ar | R1 | —NRR' | MS (M + H)+ |
|---|---|---|---|---|
| 7A-109 | 2-fluorophenyl | $—CH_3$ | 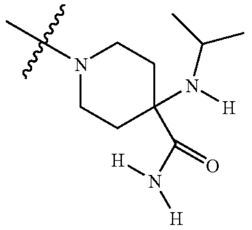 | 522.3 |

EXAMPLE 8

Preparation of Intermediate 4-[9-(4-Chlorophenyl)-8-(2-chlorophenyl)-9H-purin-6-yl]-piperazine-1,3-dicarboxylic Acid 1-tert-Butyl Ester 3-Ethyl Ester (I-(8A-1)a)

6-Chloro-9-(4-chlorophenyl)-8-(2-chlorophenyl)-9H-purine I-(4A-7)c (103 mg, 0.27 mmol), piperazine-1,3-dicarboxylic acid 1-tert-butyl ester 3-ethyl ester (Chiu, C. K.-F. and Griffith, D. A., EP 1004583 A2; 156 mg, 0.60 mmol), and triethylamine (95 μl, 0.68 mmol) were combined in ethanol (1.5 ml) and heated at 60° C. until complete by TLC (3 days). The reaction mixture was concentrated under reduced pressure and then purified on a Biotage™ Flash 12M column using 20 to 30% ethyl acetate in hexanes as eluant to afford title compound I-(8A-1)a (78 mg, 48%): +ESI MS (M+1) 597.3; $^1H$ NMR (400 MHz, $CD_3OD$) δ 8.298 (br s, 1H), 7.57 (br s, 1H), 7.48–7.25 (m, 7H), 5.60 (v br s, 1H), 4.67 (d, J=13.7 Hz, 1H), 4.23–4.05 (br m, 3H), 3.43–3.00 (br m, 2H), 1.46 (s, 9H), 1.22 (t, J=7.1 Hz, 3H).

Preparation of 1-[9-(4-Chlorophenyl)-8-(2-chlorophenyl)-9H-purin-6-yl]-piperazine-2-carboxylic Acid Ethyl Ester, Hydrochloride Salt (8A-1)

8A-1

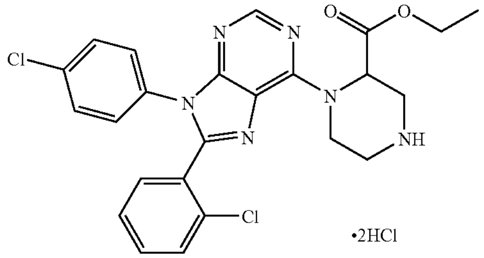

•2HCl

4-[9-(4-Chlorophenyl)-8-(2-chlorophenyl)-9H-purin-6-yl]-piperazine-1,3-dicarboxylic acid tert-butyl ester I-(8A-1)a was dissolved in 4 M HCl in dioxane (0.5 ml). After 30 minutes, the now heterogeneous reaction was concentrated under reduced pressure and then triturated from ether to afford title compound 8A-1 (38 mg, quantitative): +ESI MS (M+1) 497.2; $^1H$ NMR (400 MHz, $CD_3OD$) δ 8.43 (s, 1H), 7.58 (d, J=7.5 Hz, 1H), 7.51–7.30 (m, 7H), 4.35–4.15 (m, 2H), 4.06 (d, J=13.3 Hz, 1H), 3.73–3.47 (m, 5H), 3.40–3.30 (m, 1H), 1.23 (t, J=7.1 Hz, 3H).

The compounds listed in Table 6 below were prepared using procedures analogous to those described above for the synthesis of Compound 8A-1 using the appropriate starting materials which are available commercially, prepared using preparations well-known to those skilled in the art, or prepared in a manner analogous to routes decribed above for other intermediates. The compounds listed below were isolated as their corresponding hydrochloride salt for testing.

TABLE 6

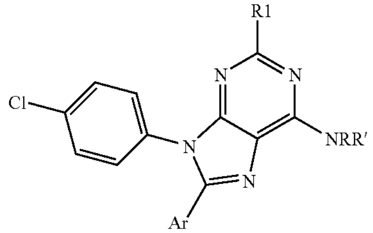

| Ex. No. | Ar | R1 | —NRR' | MS (M + H)+ |
|---|---|---|---|---|
| 8A-2 | 2,4-dichlorophenyl | —H | 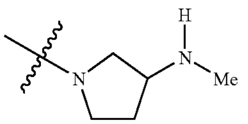 | 473.3 |

TABLE 6-continued

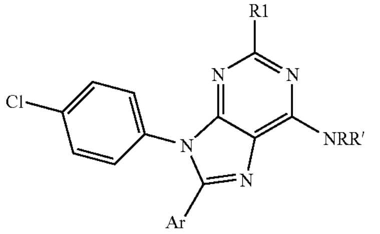

| Ex. No. | Ar | R1 | —NRR' | MS $(M + H)^+$ |
|---|---|---|---|---|
| 8A-3 | 2,4-dichlorophenyl | —H | 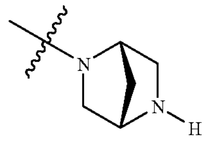 | 471.2 |
| 8A-4 | 2,4-dichlorophenyl | —H | 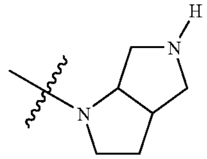 | 485.3 |
| 8A-5 | 2,4-dichlorophenyl | —H | 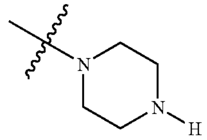 | 459.3 |
| 8A-6 | 2,4-dichlorophenyl | —H | 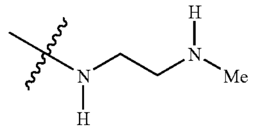 | 447.3 |

EXAMPLE 9

Preparation of {3-[9-(4-Chlorophenyl)-8-(2,4-dichlorophenyl)-9H-purin-6-yl]-3-(1α,5α,6α)-azabicyclo[3.1.0]hex-6-yl}-dimethylamine (9A-1)

9A-1

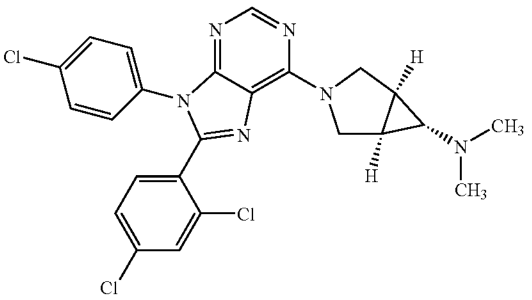

3-[9-(4-Chloro-phenyl)-8-(2,4-dichloro-phenyl)-9H-purin-6-yl]-3-(1α,5α,6α)-azabicyclo[3.1.0]hex-6-ylamine hydrochloride 14A-5 (20 mg, 0.039 mmol), paraformaldehyde (40 mg), methanol (0.75 ml) and acetic acid (13 μl, 0.22 mmol) were combined and stirred at room temperature for 30 minutes. Sodium cyanoborohydride (5 mg, 0.074 mmol) was added at this time and the reaction mixture stirred for 4 days at room temperature. The reaction mixture was diluted with saturated $NaHCO_3$ solution and extracted with ethyl acetate. The organic layers were combined, dried ($Na_2SO_4$), filtered, and evaporated to dryness. The crude product was purified via TLC preparative plate using 7:3:0.1 hexanes/diethylamine/ methanol as the solvent to afford title compound 9A-1. A solution of the material in methylene chloride was treated with excess 1 N HCl in diethyl ether, stirred, evaporated to dryness, and then triturated in diethyl ether to afford the hydrochloride salt of compound 9A-1: +ESI MS (M+1) 499.2.

Preparation of {3-[9-(4-Chlorophenyl)-8-(2,4-dichlorophenyl)-9H-purin-6-yl]-3-(1α,5α,6β)-azabicyclo[3.1.0]hex-6-yl}-dimethylamine (9A-2)

9A-2

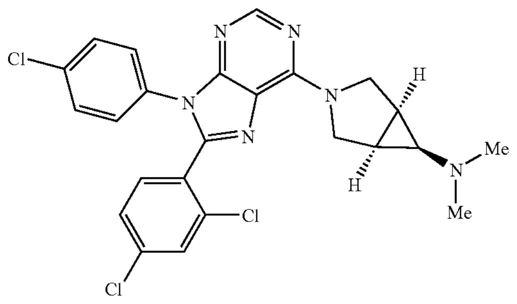

{3-[9-(4-Chlorophenyl)-8-(2,4-dichlorophenyl)-9H-purin-6-yl]-3-(1α,5α,6β)-azabicyclo[3.1.0]hex-6-yl}-dimethylamine was prepared using procedures analogous to those described above for the synthesis of Compound 9A-1. The compound was converted to the corresponding hydrochloride salt for testing: +ESI MS (M+1)=499.2

EXAMPLE 10

Preparation of 1-[9-(4-chlorophenyl)-8-(2,4-dichlorophenyl)-9H-purin-6-yl]-4-isopropylaminopiperidine-4-carboxylic Acid Amide (10A-1)

10A-1

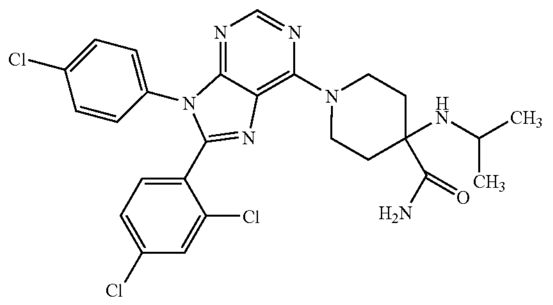

6-Chloro-9-(4-chlorophenyl)-8-(2,4-dichlorophenyl)-9H-purine I-(1A-1)d (300 mg, 0.58 mmol) and 4-isopropylamino-piperidine-4-carboxylic acid amide (101 mg, 0.548 mmol) were suspended in ethanol/methylene chloride (3 ml/1 ml). Triethylamine (0.16 ml, 1.1 mmol) was added to the suspension and the mixture heated to 60° C. until the TLC determined complete (3 h). The reaction mixture was partitioned between saturated $NaHCO_3$ solution and methylene chloride. The organic layer was dried ($Na_2SO_4$), filtered, and concentrated to dryness. The pure free base was isolated by silica gel chromatography using 2–4% methanol/ methylene chloride as the gradient eluant to afford title compound 10A-1. A solution of the material in methylene chloride was treated with excess 1 N HCl in diethyl ether, stirred, evaporated to dryness, and then triturated in diethyl ether to afford the hydrochloride salt of compound 10A-1 as a tan solid (115 mg, 38%): +ESI MS (M+1) 558.2; $^1H$ NMR (400 MHz, $CD_3OD$) δ 8.40 (s, 1H), 7.60 (d, J=8.3 Hz, 1H), 7.56 (d, J=2.1 Hz, 1H), 7.51–7.44 (m, 3H), 7.33 (d, J=8.7 Hz, 2H), 5.20 (v br m, 2H), 3.87 (br m, 2H), 3.59 (septuplet, J=6.6 Hz, 1H), 2.68 (br d, J=13.7 Hz, 2H), 2.16 (ddd, J=14.5, 10.4, 4.1 Hz, 2H), 1.39 (d, J=6.6 Hz, 6H).

EXAMPLE 11

Preparation of 9-(4-Chlorophenyl)-8-(2-fluorophenyl)-2-methyl-6-(4-methylpiperazin-1-yl)-9H-purine (11A-1)

11A-1

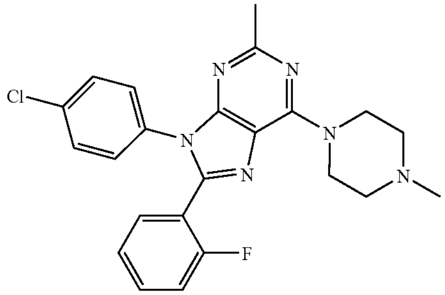

A solution of 1-methylpiperazine (200 μl) in ethanol (0.8 ml) was added to 6-chloro-9-(4-chlorophenyl)-8-(2-fluorophenyl)-2-methyl-9H-purine I-(11A-1)c (24 mg, 0.06 mmol) and placed on a 60° C. shaker apparatus for 30 minutes. The reaction was loaded directly onto a TLC preparative plate for purification using 10% methanol/ethyl acetate as the solvent to obtain the desired title compound 11A-1: +ESI MS (M+1) 465. A solution of the material in methylene chloride/methanol was treated with excess 1 N HCl in diethyl ether, stirred, evaporated to dryness, and then triturated in diethyl ether to afford the hydrochloride salt of compound 11A-1 (35 mg, quantitative): +ESI MS (M+1) 437.2; $^1H$ NMR (400 MHz, $CD_3OD$) δ 7.70–7.25 (br m, 7H), 7.09 (t, J=9.1 Hz, 1H), 5.80 (br s, 2H), 3.74 (br s, 4H), 3.36 (br s, 2H), 2.99 (s, 3H), 2.64 (s, 3H).

The compounds listed in Table 8 below were prepared using procedures analogous to those described above for the synthesis of Compound 11A-1 using the appropriate starting materials which are available commercially, prepared using preparations well-known to those skilled in the art, or prepared in a manner analogous to routes decribed above for other intermediates. The compounds listed below were isolated initially as the free base and then generally converted to their corresponding hydrochloride salt for testing.

TABLE 8

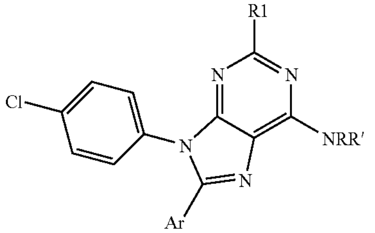

| Ex. No. | Ar | R1 | —NRR' | MS $(M + H)^+$ |
|---|---|---|---|---|
| 11A-2 | 2-chlorophenyl | —H | 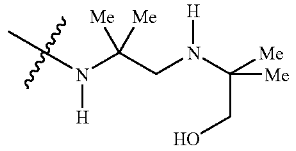 | 499.1 |
| 11A-3 | 2-fluorophenyl | $—CH_2C(CH_3)_3$ | 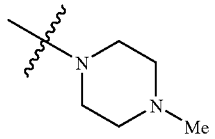 | 493.4 |
| 11A-4 | 2-fluorophenyl | $—CH(CH_3)_2$ | 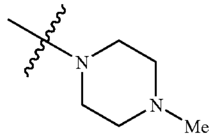 | 465.3 |

TABLE 8-continued

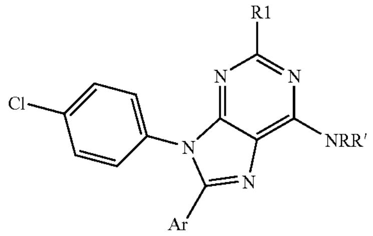

| Ex. No. | Ar | R1 | —NRR' | MS (M + H)+ |
|---|---|---|---|---|
| 11A-5 | 2-fluorophenyl | $—CH_2CH_2CH_3$ | 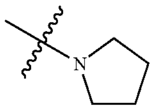 | 436.3 |
| 11A-6 | 2-fluorophenyl | $—CH(CH_3)_2$ | 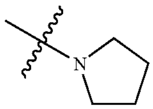 | 436.3 |
| 11A-7 | 2-fluorophenyl | $—CH_2C(CH_3)_3$ | 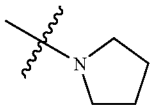 | 464.3 |
| 11A-8 | 2-fluorophenyl | $—CH_3$ | 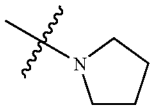 | 408.2 |

EXAMPLE 12

Preparation of 9-(4-Chlorophenyl)-8-(2-fluorophenyl)-6-(4-methylpiperazin-1-yl)-9H-purine (12A-1)

12A-1

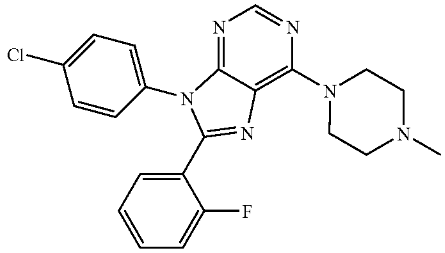

A mixture of 6-chloro-9-(4-chlorophenyl)-8-(2-fluorophenyl)-9H-purine (prepared analogous to I-(7A-80)c; 25 mg, 0.07 mmol) and 1-methylpiperazine (200 μl) in ethanol (1 ml) were stirred overnight at room temperature. The precipitated title compound 12A-1 was collected by filtration and rinsed with ether (15 mg, 51%): +ESI MS (M+1) 410; $^1H$ NMR (400 MHz, $CD_2Cl_2$) δ 8.27 (s, 1H), 7.63 (td, J=7.3, 1.7 Hz, 1H), 7.45 (m, 1H), 7.38 (d, J=8.7 Hz, 2H), 7.26 (t, J=7.5 Hz, 1H), 7.22 (d, J=8.7 Hz, 2H), 7.01 (t, J=8.9 Hz, 1H), 4.34 (br m, 4H), 2.52 (t, J=5.0 Hz, 4H), 2.30 (s, 3H). A solution of the material in methylene chloride/methanol was treated with excess 1 N HCl in diethyl ether, stirred, evaporated to dryness, and then triturated in diethyl ether to afford the hydrochloride salt of compound 12A-1.

The compounds listed in Table 9 below were prepared using procedures analogous to those described above for the synthesis of Compound 12A-1 using the appropriate starting materials which are available commercially, prepared using preparations well-known to those skilled in the art, or prepared in a manner analogous to routes decribed above for other intermediates. The compounds listed below were isolated initially as the free base and then generally converted to their corresponding hydrochloride salt for testing.

TABLE 9

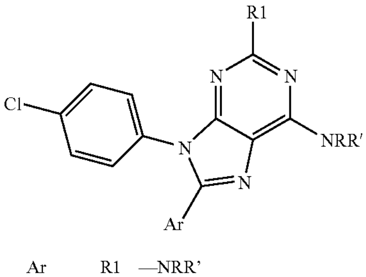

| Ex. No. | Ar | R1 | —NRR' | MS (M + H)+ |
|---|---|---|---|---|
| 12A-2 | 2-fluoro-phenyl | —H | 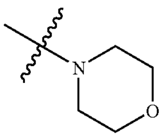 | 410.2 |

TABLE 9-continued

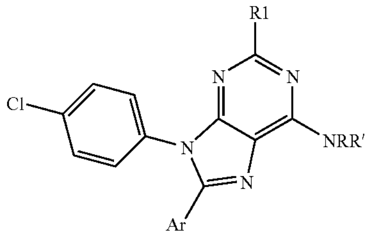

| Ex. No. | Ar | R1 | —NRR' | MS (M + H)+ |
|---|---|---|---|---|
| 12A-3 | 2-fluoro-phenyl | —H | 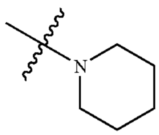 | 408.1 |
| 12A-4 | 2-chloro-phenyl | —H | 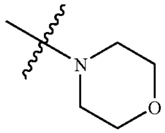 | 426.1 |
| 12A-5 | 2-chloro-phenyl | —H | 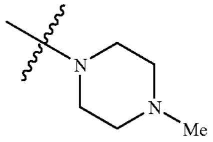 | 439.1 |
| 12A-6 | 2-chloro-phenyl | —H | 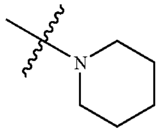 | 424.1 |
| 12A-7 | 2-chloro-phenyl | —H | 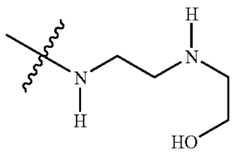 | 443.1 |

TABLE 9-continued

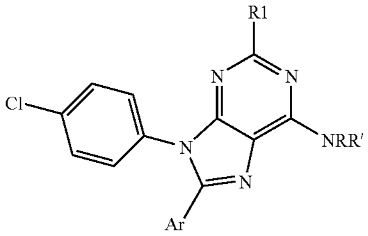

| Ex. No. | Ar | R1 | —NRR' | MS (M + H)+ |
|---|---|---|---|---|
| 12A-8 | 2-chloro-phenyl | —H | 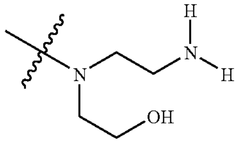 | 443.1 |

EXAMPLE 13

Preparation of 8-[9-(4-Chlorophenyl)-8-(2-chlorophenyl)-9H-purin-6-yl]-1-isopropyl-1,3,8-triazaspiro[4.5]decan-4-one (13A-1)

13A-1

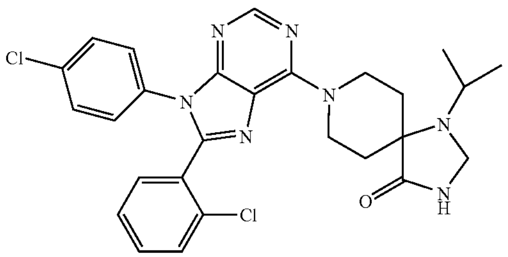

A mixture of 6-chloro-9-(4-chlorophenyl)-8-(2-chlorophenyl)-9H-purine I-(4A-7)c (19 mg, 0.052 mmol), 1-isopropyl-1,3,8-triazaspiro[4.5]decan-4-one (Janssen, P. A. J., U.S. Pat. No. 3,238,216; 20 mg, 0.10 mmol) and triethylamine (11 μl) in ethanol (1 ml) was stirred overnight at room temperature. The reaction mixture was concentrated under reduced pressure and then purified on a Biotage™ Flash 12S column using 3% methanol in methylene chloride as eluant to afford title compound 13A-1 (25 mg): +ESI MS (M+1) 536.3; $^1$H NMR (400 MHz, $CD_3OD$) δ 8.22 (s, 1H), 7.59 (d, J=7.5 Hz, 1H), 7.46–7.35 (m, 5H), 7.29 (d, J=8.7 Hz, 2H), 4.27 (s, 2H), 4.25 (v br s, 4H), 3.15 (septuplet, J=6.6 Hz, 1H), 2.00–1.83 (m, 4H), 1.07 (d, J=6.6 Hz, 6H). A solution of the material in methylene chloride/ methanol was treated with excess 1 N HCl in diethyl ether, stirred, evaporated to dryness, and then triturated in diethyl ether to afford the hydrochloride salt of compound 13A-1 (23 mg, 77%): $^1$H NMR (400 MHz, $CD_3OD$) δ 8.43 (s, 1H), 7.61 (d, J=7.5 Hz, 1H), 7.53–7.40 (m, 5H), 7.35 (d, J=8.7 Hz, 2H), 4.20 (v br s), 3.94 (septuplet, J=6.6 Hz, 1H), 2.45 (m, 4H), 1.41 (d, J=6.6 Hz, 6H).

The compounds listed in Table 10 below were prepared using procedures analogous to those described above for the synthesis of Compound 13A-1 using the appropriate starting materials which are available commercially, prepared using-preparations well-known to those skilled in the art, or prepared in a manner analogous to routes decribed above for other intermediates. The compounds listed below were isolated initially as the free base and then generally converted to their corresponding hydrochloride salt for testing.

TABLE 10

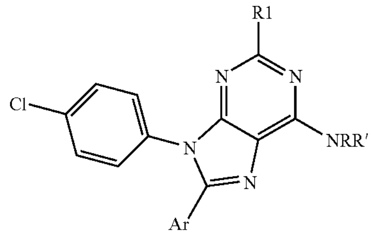

| Ex. No. | Ar | R1 | —NRR' | MS (M + H)$^+$ |
|---|---|---|---|---|
| 13A-2 | 2-fluorophenyl | —H | 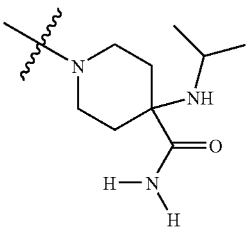 | 508.3 |
| 13A-3 | 2-fluorophenyl | —H | 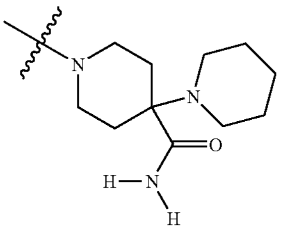 | 534.3 |
| 13A-4 | 2-fluorophenyl | —H | 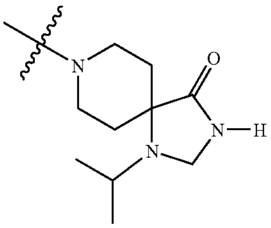 | 520.3 |
| 13A-5 | 2-chlorophenyl | —H | 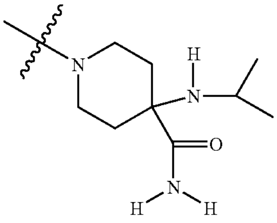 | 524.3 |
| 13A-6 | 2-chlorophenyl | —H | 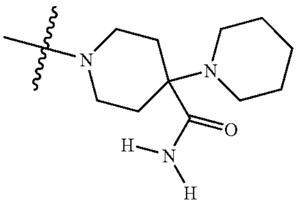 | 550.3 |

TABLE 10-continued

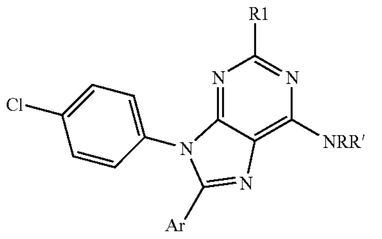

| Ex. No. | Ar | R1 | —NRR' | MS $(M + H)^+$ |
| --- | --- | --- | --- | --- |
| 13A-7 | 2-chlorophenyl | —H | 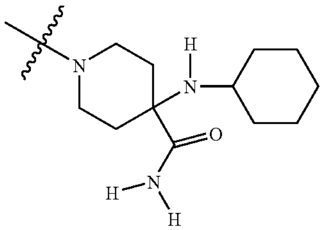 | 564.2 |
| 13A-8 | 2-chlorophenyl | —H | 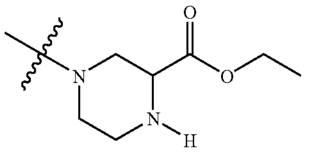 | 497.1 |
| 13A-9 | 2-chlorophenyl | —H | 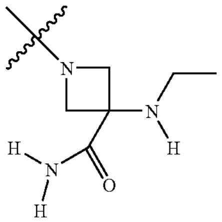 | 482.4 |
| 13A-10 | 2-chlorophenyl | —H | 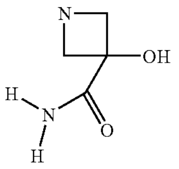 | 455.3 |

EXAMPLE 14

Preparation of Intermediate {3-[9-(4-Chlorophenyl)-8-(2-fluorophenyl)-9H-purin-6-yl]-3-(1α,5α,6α)-azabicyclo[3.1.0]hex-6-yl}-carbamic Acid tert-Butyl Ester (I-(14A-1)a)

6-Chloro-9-(4-chlorophenyl)-8-(2-fluorophenyl)-9H-purine I-(4A-7)c (83 mg, 0.22 mmol), (3-(1α,5α,6β)-azabicyclo[3.1.0]hex-6-yl)-carbamic acid tert-butyl ester (prepared using the procedures described in Brighty, Katherine E., U.S. Pat. No. 5,164,402; 87 mg, 0.44 mmol), and triethylamine (46 μl, 0.33 mmol) were combined in ethanol (1 ml) and stirred overnight. The reaction mixture was concentrated under reduced pressure and then purified on a Biotage™ Flash 12S column using 3% methanol in methylene chloride as eluant to afford title compound I-(14A-1)a (117 mg, 99%): +APCI MS (M+1) 537.4; $^1H$ NMR (400 MHz, $CD_3OD$) δ 8.19 (s, 1H), 7.59 (d, J=7.5 Hz, 1H), 7.50–7.35 (m, 5H), 7.27 (d, J=8.7 Hz, 2H), 4.75 (br s, 1H), 4.20 (br s, 1H), 4.03 (br s, 1H), 3.75 (br s, 1H), 2.24 (s, 1H), 1.89 (br s, 2H), 1.42 (s, 9H).-

Preparation of 3-[9-(4-Chlorophenyl)-8-(2-fluorophenyl)-9H-purin-6-yl]-3-(1α,5α,6α)-azabicyclo[3.1.0]hex-6-ylamine, Hydrochloride Salt (14A-1)

14A-1

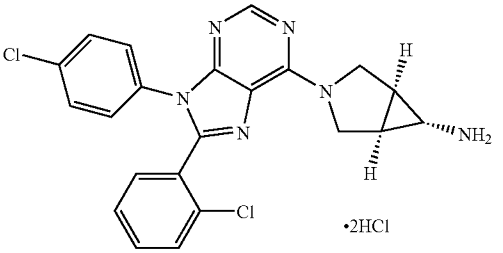

•2HCl

{3-[9-(4-Chlorophenyl)-8-(2-fluorophenyl)-9H-purin-6-yl]-3-(1α,5α,6α)-azabicyclo[3.1.0]hex-6-yl}-carbamic acid tert-butyl ester I-(14A-1)a was dissolved in methanol (1 ml) and to the mixture was added 4 M HCl in dioxane (1 ml). The reaction mixture was stirred 5 hours and then concentrated and triturated in ether to afford title compound 14A-1 (112 mg, quantitative): +ESI MS (M+1) 437.1; $^{1}H$ NMR (400 MHz, $CD_3OD$) δ 8.39 (s, 1H), 7.60 (d, J=7.5 Hz, 1H), 7.55–7.40 (m, 5H), 7.32 (d, J=8.7 Hz, 2H), 2.66 (s, 1H), 2.37 (br s, 2H).

The compounds listed in Table 11 below were prepared using procedures analogous to those described above for the synthesis of Compound 14A-1 using the appropriate starting materials which are available commercially, prepared using preparations well-known to those skilled in the art, or prepared in a manner analogous to routes decribed above for other intermediates. The compounds listed below were isolated as their corresponding hydrochloride salt for testing.

TABLE 11

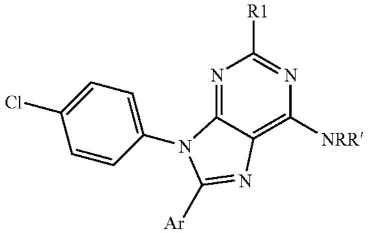

| Ex. No. | Ar | R1 | —NRR' | MS (M + H)$^+$ |
|---|---|---|---|---|
| 14A-2 | 2-chlorophenyl | —H | 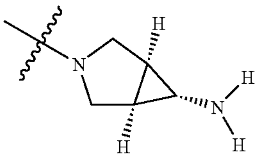 | 437.1 |
| 14A-3 | 2-fluorophenyl | —H | 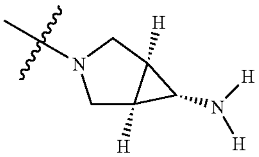 | 421.1 |
| 14A-4 | 2-fluorophenyl | —H | 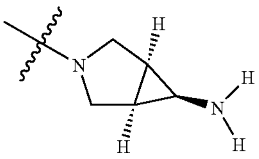 | 421.1 |
| 14A-5 | 2,4-dichlorophenyl | —H | 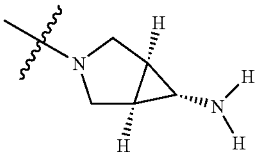 | 471.3 |

EXAMPLE 15

Preparation of {1-[9-(4-Chlorophenyl)-8-(2,4-dichlorophenyl)-9H-purin-6-yl]-ethyl}-isopropylamine (15A-1)

15A-1

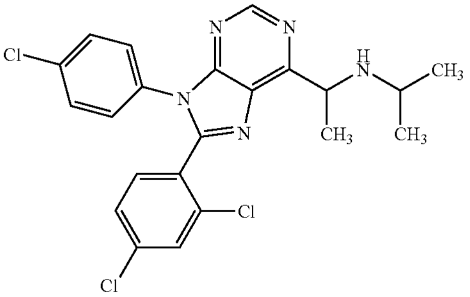

A solution of 1-[9-(4-chlorophenyl)-8-(2,4-dichlorophenyl)-9H-purin-6-yl]-ethanone I-(15A-1)a (16 mg, 0.038 mmol) and isopropylamine (6.5 μl, 0.076 mmol) in methylene chloride (0.3 ml) was stirred at room temperature and to it was added titanium(IV) isopropoxide (34 μl, 0.114 mmol). The reaction mixture was stirred for 3 hours and then methanol (0.5 ml) was added followed by sodium borohydride (5 mg). When the reaction was shown to be complete by LC/MS it was purified by TLC preparative plate using 10% methanol/methylene chloride with 1% ammonium hydroxide as the solvent to obtain title compound 15A-1. A solution of the material in methylene chloride was treated with excess 1 N HCl in diethyl ether, stirred, evaporated to dryness, and then triturated in diethyl ether to afford the hydrochloride salt of compound 15A-1 (5.9 mg): +ESI MS (M+1) 460.5; $^{1}$H NMR (500 MHz, $CD_3OD$) δ 9.08 (s, 1H), 7.77 (d, J=8.3 Hz, 1H), 7.64 (s, 1H), 7.59–7.48 (m, 3H), 7.41 (d, J=8.8 Hz, 2H), 5.38 (q, J=6.2 Hz, 1H), 3.45 (septuplet, J=6.5 Hz, 1H), 1.84 (d, J=6.7 Hz, 3H), 1.43 (d, J=6.7 Hz, 3H), 1.41, (d, J=6.2 Hz, 3H).

Preparation of 9-(4-Chlorophenyl)-8-(2,4-dichlorophenyl)-6-(1-piperidin-1-yl-ethyl)-9H-purine (15A-2)

15A-2

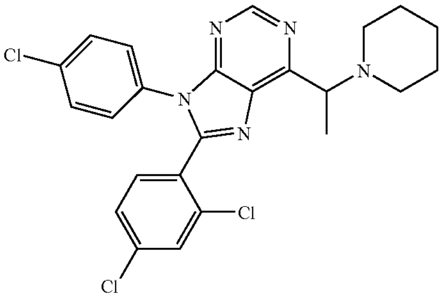

9-(4-Chlorophenyl)-8-(2,4-dichlorophenyl)-6-(1-piperidin-1-yl-ethyl)-9H-purine was prepared using procedures analogous to those described above for the synthesis of Compound 15A-1. The compound was converted to the corresponding hydrochloride salt for testing: +ESI MS (M+1)=486.5

EXAMPLE 16

Preparation of [9-(4-Chlorophenyl)-8-(2,4-dichlorophenyl)-9H-purin-6-ylmethyl]-cyclohexylamine (16A-1)

16A-1

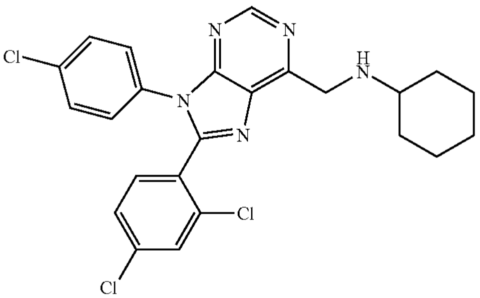

C-[9-(4-Chlorophenyl)-8-(2,4-dichlorophenyl)-9H-purin-6-yl]-methylamine I-(16A-1)b (19 mg, 0.047 mmol) was dissolved in methanol (1 ml) and to it was added cyclohexanone (1 drop) and acetic acid (1 drop). The reaction mixture was stirred at room temperature for 0.5 hour. and then sodium cyanoborohydride was added (5 mg) and the stirring continued until the reaction was complete (2 hours). The reaction mixture was concentrated and the residue diluted with saturated $NaHCO_3$ solution and extracted into ethyl acetate. The organic layers were combined, dried ($Na_2SO_4$), filtered, and 5% methanol in ethyl acetate as the solvent to give title compound 16A-1. The residue was dissolved in methylene chloride and treated with 2M HCl/ether to form the desired HCl salt. Ether was added to the reaction mixture to precipitate the product. The excess ether was decanted and the crystals pumped to dryness on high vacuum to afford the hydrochloride salt of compound 16A-1 (6.8 mg, 30%): +ESI MS (M+1) 486.6; $^{1}$H NMR (500 MHz, $CD_3OD$) δ 9.07 (s, 1H), 7.71 (d, J=8.8 Hz, 1H), 7.64 (d, J=2.1 Hz, 1H), 7.56 (dd, J=8.8, 2.1 Hz, 1H), 7.52 (d, J=8.8 Hz, 2H), 7.40 (d, J=8.8 Hz, 2H), 4.94 (s, 2H), 3.35 (m 1H), 2.28 (br d, J=12.4 Hz, 2H), 1.96 (br d, J=13.5 Hz, 2H), 1.78 (br d, J=13.0 Hz, 1H), 1.60–1.20 (m, 5H).

The compounds listed in Table 13 below were prepared using procedures analogous to those described above for the synthesis of Compound 16A-1 using the appropriate starting materials which are available commercially, prepared using preparations well-known to those skilled in the art, or prepared in a manner analogous to routes decribed above for other intermediates. The compounds listed below were isolated initially as the free base and then generally converted to their corresponding hydrochloride salt for testing.

TABLE 13

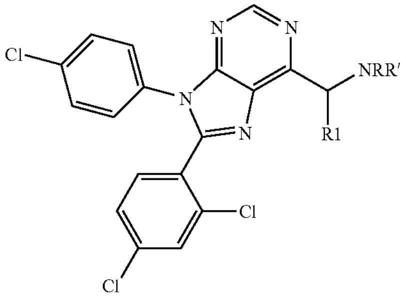

| Ex. No. | R1 | —NRR' | MS (M + H)$^+$ |
|---|---|---|---|
| 16A-2 | —H | 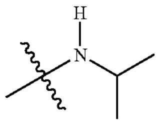 | 446.5 |
| 16A-3 | —H | 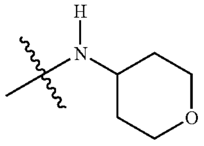 | 488.5 |
| 16A-4 | —H | 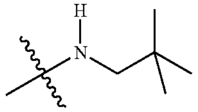 | 474.6 |
| 16A-5 | —H | 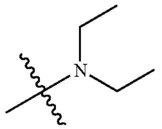 | 460.5 |

EXAMPLE 17

Preparation of 9-(4-Chlorophenyl)-8-(2-chlorophenyl)-6-pyrrolidin-1-yl9H-purine (17A-1)

17A-1

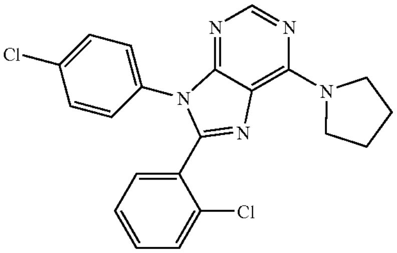

N-4-(4-Chlorophenyl)-6-pyrrolidin-1-yl-pyrimidine4,5-diamine I-(17A-1)a (25 mg, 0.086 mmol) and 2-chlorobenzoic acid ethyl ester (31 mg, 0.17 mmol) were combined in polyphosphoric acid (1 ml) and heated to 150° C. until completion (2 hours). The reaction mixture was diluted with water, made basic with 6M NaOH solution and then extracted with methylene chloride. The organic layers were combined, dried ($Na_2SO_4$), filtered, and concentrated to dryness. The crude material was purified by preparative TLC using 2 passes of 20% ethyl acetate in methylene chloride as solvent to give title compound 17A-1 (11 mg, 32%): +ESI MS (M+1) 410.5; $^1$H NMR (500 MHz, $CDCl_3$) δ 8.44 (s, 1H), 7.51 (dd, J=7.8, 2.1 Hz, 1H), 7.42–7.33 (m, 5H), 7.21 (d, J=8.8 Hz, 2H), 4.30 (br s, 2H), 3.88 (br s, 2H), 2.15–2.00 (br m, 4H). A solution of the material in methylene chloride was treated with excess 1 N HCl in diethyl ether, stirred, evaporated to dryness, and then triturated in diethyl ether to afford the hydrochloride salt of compound 17A-1 (12 mg, quantitative): +ESI MS (M+1)410.5.

The compounds listed in Table 14 below were prepared using procedures analogous to those described above for the synthesis of Compound 17A-1 using the appropriate starting materials which are available commercially, prepared using preparations well-known to those skilled in the art, or prepared in a manner analogous to routes decribed above for other intermediates. The compounds listed below were isolated initially as the free base and then generally converted to their corresponding hydrochloride salt for testing.

TABLE 14

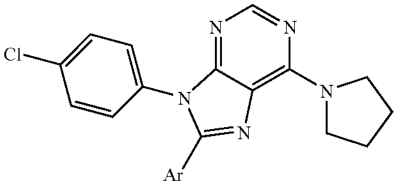

| Example No. | Ar | MS (M + H)$^+$ |
|---|---|---|
| 17A-2 | 3-chlorophenyl | 410.5 |
| 17A-3 | 4-chlorophenyl | 410.5 |

EXAMPLE 18

Preparation of 9-(4-Chlorophenyl)-8-(2-fluorophenyl)-6-pyrrolidin-1- yl-9H-purine (18A-1)

18A-1

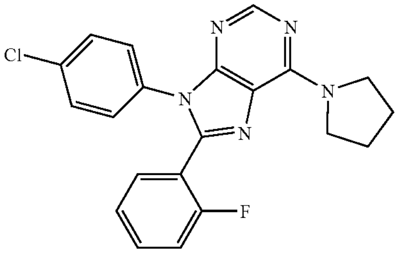

2-Fluorobenzoic acid (22 mg, 0.15 mmol) and N4-(4-chlorophenyl)-6-pyrrolidin-1-yl-pyrimidine-4,5-diamine I-(17A-1)a (30 mg, 0.10 mmol) were dissolved in dioxane (0.7 ml) and 50% propanephosphoric acid cyclic anhydride in ethyl acetate (0.3 ml). The resulting mixture was shaken at 95° C. for 48 h. The reaction was cooled and diluted up to a volume of 1.8 ml with water for purification. The purification of the crude mixture was accomplished by reverse phase preparative Gilson 215 HPLC with the Hewlett Packard Series 1100MSD, and G1315A DAD using a Luna 5 micron C8(2) 250*21.2 mm Phenomenex column. The gradient eluant used was 0.1% formic acid in water (A)

and acetonitrile (B) with trifluoroacetic acid as a buffer: 0.04 min.—80% A, 20% B; 20 min.—20% A, 80% B; 25 min.—100% B. The fractions with the desired compound were combined and evaporated to dryness to give title compound 18A-1. The residue was dissolved in methanol (1.5 ml) and treated with 4M HCl/dioxane (0.2 ml). The resulting mixture was shaken at 40° C. for 1 h then dried in a flow of nitrogen at 30° C. over 18 hours to obtain the hydrochloride salt of compound as a solid 18A-1 (4.2 mg, 10%): +ESI MS (M+1) 394.3; $^{1}$H NMR (500 MHz, $CD_3OD$) δ 8.36 (s, 1H), 7.72 (t, J=7.8 Hz, 1H), 7.59 (m, 1H), 7.51 (d, J=8.8 Hz, 2H), 7.40–7.33 (m, 3H), 7.14 (t, J=9.3 Hz, 1H), 4.49 (br s, 2H), 3.84 (br s, 2H), 2.24 (br s, 4H).

The compounds listed in Table 15 below were prepared using procedures analogous to those described above for the synthesis of Compound 18A-1 using the appropriate starting materials which are available commercially, prepared using preparations well-known to those skilled in the art, or prepared in a manner analogous to routes decribed above for other intermediates. The compounds listed below were isolated initially as the free base and then generally converted to their corresponding hydrochloride salt for testing.

TABLE 15

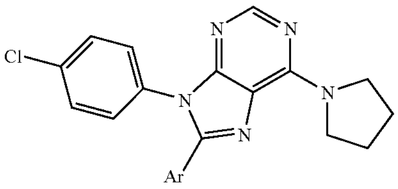

| Example No. | Ar | MS (M + H)$^+$ |
|---|---|---|
| 18A-2 | 2-cyanophenyl | 401.2 |
| 18A-3 | 3-cyanophenyl | 401.2 |
| 18A-4 | 3-fluorophenyl | 394.2 |
| 18A-5 | 2,4-dimethoxy phenyl | 436.2 |
| 18A-6 | 4-trifluoromethylphenyl | 444.2 |
| 18A-7 | 4-chloro-2-methoxyphenyl | 440.2 |
| 18A-8 | 2-ethoxyphenyl | 420.2 |
| 18A-9 | 3,4-difluorophenyl | 412.2 |
| 18A-10 | 3-methoxyphenyl | 406.2 |
| 18A-11 | 4-isopropoxyphenyl | 434.2 |
| 18A-12 | 2-methoxyphenyl | 406.2 |
| 18A-13 | 3-chloro-4-fluorophenyl | 428.0 |
| 18A-14 | 3-fluoro-2-methylphenyl | 408.2 |
| 18A-15 | 4-difluoromethoxyphenyl | 442.2 |
| 18A-16 | 4-chloro-2-fluorophenyl | 428.0 |
| 18A-17 | 3-difluoromethoxyphenyl | 442.2 |
| 18A-18 | phenyl | 376.2 |
| 18A-19 | 2,3-difluorophenyl | 412.2 |
| 18A-20 | 2,4-difluorophenyl | 412.2 |
| 18A-21 | 2-chloro-4-fluorophenyl | 428.0 |
| 18A-22 | 3-chloro-2-fluorophenyl | 428.0 |
| 18A-23 | 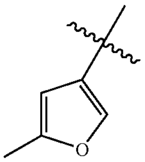 | 380.4 |
| 18A-24 | 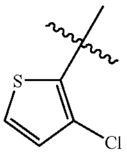 | 416.4 |

TABLE 15-continued

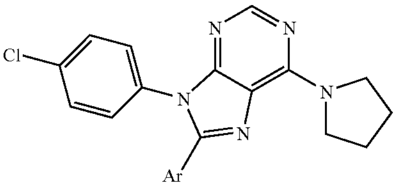

| Example No. | Ar | MS (M + H)$^+$ |
|---|---|---|
| 18A-25 | 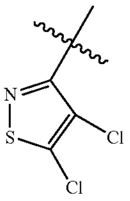 | 451.4 |
| 18A-26 | 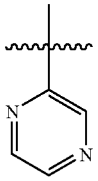 | 378.9 |
| 18A-27 | 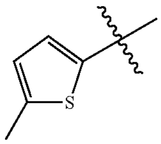 | 396.7 |
| 18A-28 | 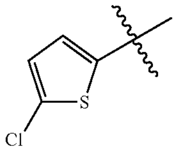 | 416.7 |
| 18A-29 | 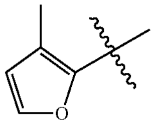 | 380.9 |
| 18A-30 | 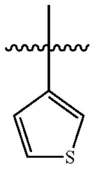 | 382.0 |
| 18A-31 | 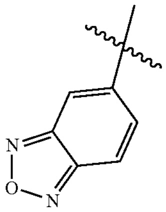 | 418.2 |

TABLE 15-continued
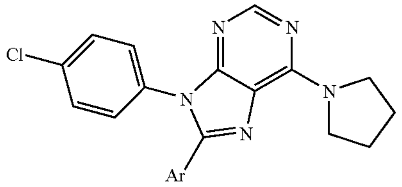
| Example No. | Ar | MS $(M + H)^+$ |
|---|---|---|
| 18A-32 | 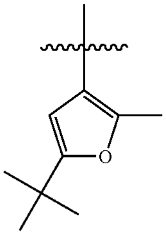 | 436.2 |
| 18A-33 | 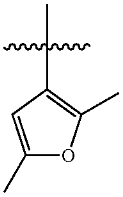 | 394.2 |
| 18A-34 | 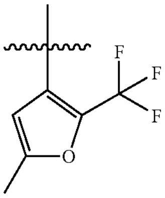 | 448.2 |
| 18A-35 | 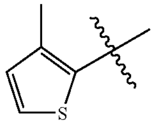 | 396.2 |
| 18A-36 | 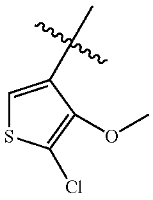 | 446.0 |
| 18A-37 | 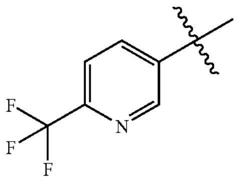 | 445.2 |
| 18A-38 | 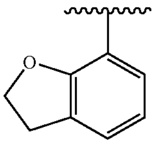 | 418.2 |
TABLE 15-continued
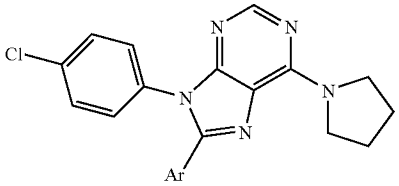
| Example No. | Ar | MS $(M + H)^+$ |
|---|---|---|
| 18A-39 | 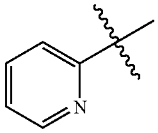 | 377.2 |
| 18A-40 | 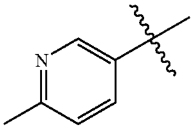 | 391.2 |
| 18A-41 | 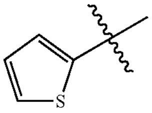 | 382.0 |
| 18A-42 | 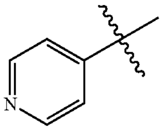 | 377.2 |
| 18A-43 | 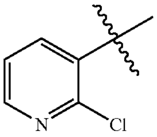 | 411.0 |
| 18A-44 | 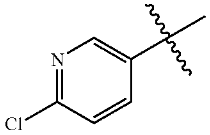 | 411.0 |
| 18A-45 | 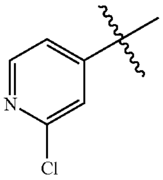 | 411.0 |
| 18A-46 | 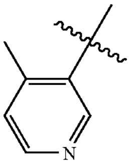 | 391.2 |

EXAMPLE 19

Preparation of 1-[9-(4-chlorophenyl)-8-(2-chlorophenyl)-9H-purin-6-ylamino]-cyclopentanecarboxylic Acid, Potassium Salt (19A-1)

19A-1

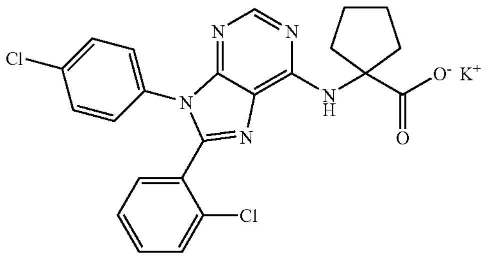

1-Aminocyclopentanecarboxylic acid (36 mg, 0.28 mmol) and $Na_2SO_4$ (15 mg, 0.14 mmol) were combined in water (1 ml). 6-Chloro-9-(4-chlorophenyl)- 8-(2-chlorophenyl)-9-purine I-(4A-7)c (57.5 mg, 0.137 mmol) was added to the reaction mixture and heated to reflux overnight. The reaction mixture was diluted with 1 M HCl and the resulting solids were collected by filtration and dried under high vacuum to give 2:1 product to starting purine (49 mg). The residue was dissolved in methylene chloride (1.5 ml) and treated with potassium trimethylsilanolate (21 mg). Ether was added to the slowly stirring reaction mixture and a precipitate was formed. The solids were isolated by filtration, washed with 1:1 methylene chloride/ether, and dried under high vacuum to afford title compound 19A-1 (28 mg, 44%): +ESI MS (M+1) 468.1; $^1H$ NMR (400 MHz, $CD_3OD$) δ 8.21 (s, 1H), 7.60 (dd, J=7.5, 1.7 Hz, 1H), 7.50–7.35 (m, 5H), 7.29 (d, J=8.7 Hz, 2H), 2.42–2.33 (br m, 2H), 2.26–2.17 (br m, 2H), 1.87 (br s, 4H).

Preparation of 4-Amino-1-[9-(4-chlorophenyl)-8-(2-chlorophenyl)-9H-purin-6-yl]-piperidine-4-carboxylic Acid, Potassium Salt (19A-2)

19A-2

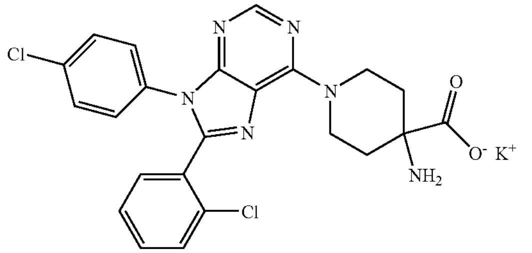

4-Amino-1-[9-(4-chlorophenyl)-8-(2-chlorophenyl)-9H-purin-6-yl]-piperidine- 4-carboxylic acid was prepared using procedures analogous to those described above for the synthesis of Compound 19A-1. +ESI MS (M+1)=483.1

EXAMPLE 20

Preparation of 1-[9-(4-Chlorophenyl)-8-(2-chlorophenyl)-9H-purin-6-yl]- 4-ethylaminopiperidine-4-carboxylic Acid Amide (20A-1)

20A-1

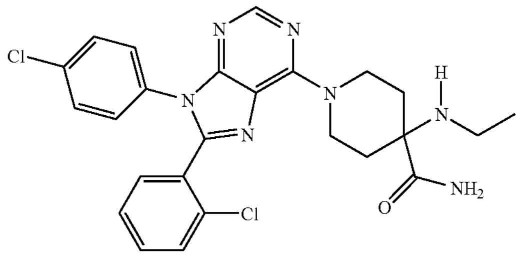

To a pale orange solution of 6-chloro-9-(4-chlorophenyl)-8-(2-chlorophenyl)-9H-purine I-(4A-7)c (1.00 g, 2.66 mmol) in acetone (13 ml) at room temperature was added triethylamine (410 μl, 2.94 mmol). A solution of 4-ethylamino-piperidine-4-carboxylic acid amide I-(7A-80)f in water (1.5 ml) was then added to give a clear yellow reaction solution. After stirring at room temperature for 3 days the cloudy white reaction mixture was diluted with water (11 ml). After stirring 1 hour at room temperature followed by 1 hour at 0° C., the precipitate was collected on a sintered glass funnel and rinsed with cold 1:1, acetone: $H_2O$. The solid was dried, in vacuo, to give title compound 20A-1 as a colorless solid (1.22 g, 90%): +ESI MS (M+1) 510.2; $^1H$ NMR (400 MHz, $CD_3OD$) δ 8.19 (s, 1H), 7.57 (d, J=7.0 Hz,1H), 7.45–7.35 (m, 5H), 7.26 (d, J=8.7 Hz, 2H), 4.54 (br s, 2H), 4.24 (br s, 2H), 2.51 (q, J=7.0 Hz, 2H), 2.12–2.06 (m, 2H), 1.76–1.72 (m, 2H) 1.10 (t, J=7.0 Hz, 3H).

The above solid (1.00 g, 1.96 mmol) was suspended in isopropanol (16 ml) followed by addition of THF (6 ml) to give a clear solution. While at room temperature, aqueous 2 M HCl (1.3 ml, 2.6 mmol) was added over 1 minute and then stirred at room temperature for 1 hour, followed by heating to reflux and stirring for 16 hours. After cooling, the mixture was stirred in an ice bath 2 hours. The colorless precipitate was collected on a sintered glass funnel and rinsed with cold 95:5 isopropanol: $H_2O$, further dried, in vacuo, to afford 20A-1 a colorless solid (0.86 g, 79%). A portion of this material (0.81 g, 1.48 mmol) was suspended in 15 ml of 95:5 isopropanol: $H_2O$, then heated to reflux and stirred for 17 hr. The suspension was cooled to room temperature, stirred for 2 hours, then collected on a medium sintered glass funnel and rinsed with room temperature 95:5 isopropanol: $H_2O$. After further drying, in vacuo, the hydrochloride salt of compound 20A-1 was obtained as a colorless solid (0.72 g, 89%): +ESI MS (M+1) 510.2; $^1H$ NMR (400 MHz, $CD_3OD$) δ 8.31 (s, 1H), 7.60 (d, J=7.4 Hz, 1H), 7.51–7.40 (m, 5H), 7.29 (d, J=8.7 Hz, 2H), 4.78 (br s, 2H), 4.22 (br s, 2H), 3.07 (q, J=7.0 Hz, 2H), 2.56–2.52 (m, 2H), 2.09–2.03 (m, 2H), 1.36 (t, J=7.0 Hz, 3H). The benzenesulfonate and methanesulfonate salts of 20A-1 were prepared in an analogous fashion.

EXAMPLE 21

Preparation of 1-[9-(4-Chlorophenyl)-8-(2-chlorophenyl)-9H-purin-6-yl]-4-methylaminopiperidine-4-carboxylic Acid Methyl Ester (21A-1)

21A-1

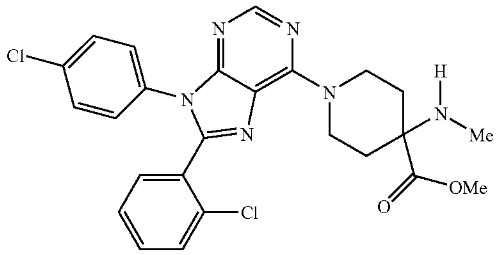

1-[9-(4-Chlorophenyl)-8-(2-chlorophenyl)-9H-purin-6-yl]-4-methylaminopiperidine-4-carboxylic acid amide 7A-87 (Example 164; 53 mg, 0.093 mmol) and Amberlyst 15 (0.8 g) in methanol (5 ml) was sealed in a tube and then heated to 60° C. for 20 h. The resin was removed by filtration and washed with 2:1 methanol/triethylamine and then 10% $NH_4OH$ in methanol. The combined organic layers were concentrated and then purified on a Biotage™ Flash 12S column using 0–2–4% methanol in methylene chloride as eluant to give title compound 21A-1 as a light brown solid (26 mg, 55%): +ESI MS (M+1) 511.1; $^1H$ NMR (400 MHz, $CD_2Cl_2$) δ 8.28 (s, 1H), 7.52 (d, J=8.3 Hz, 1H), 7.44–7.32 (m, 5H), 7.21 (d, J=8.7 Hz, 2H), 5.55 (v br s, 1H), 4.65 (v br s, 2H), 4.13 (v br s, 2H), 3.71 (s, 3H), 2.28 (s, 3H), 2.07 (ddd, J=13.7, 9.6, 3.7 Hz, 2H), 1.79 (dt, J=13.7, 3.9 Hz, 2H).

Preparation of 1-[9-(4-Chlorophenyl)-8-(2-chlorophenyl)-9H-purin-6-yl]-4-ethylaminopiperidine-4-carboxylic Acid Methyl Ester (21A-2)

21A-2

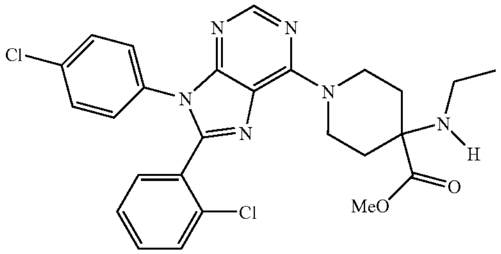

1-[9-(4-Chlorophenyl)-8-(2-chlorophenyl)-9H-purin-6-yl]-4-ethylaminopiperidine-4-carboxylic acid methyl ester was prepared using procedures analogous to those described above for the synthesis of Compound 21A-1. +APCI MS (M+1)=525.3.

EXAMPLE 22

Preparation of 1-[9-(4-Chlorophenyl)-8-(2-chlorophenyl)-9H-purin-6-yl]-4-isoproplyaminopiperidine-4-carbonitrile (22A-1)

22A-1

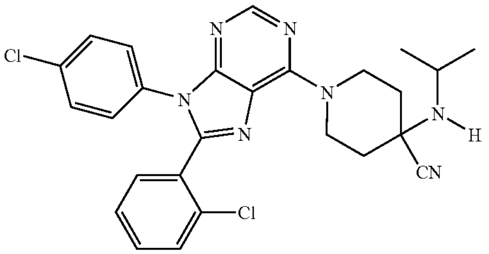

A suspension of 1-[9-(4-chlorophenyl)-8-(2-chlorophenyl)-9H-purin-6-yl]-piperidin-4-one 7A-96 (48 mg, 0.11 mmol) in methanol (0.4 ml) was cooled to 0° C. and then treated with 2-propylamine (15 μl, 0.15 mmol) and then concentrated aqueous HCl. After stirring 5 minutes, a solution of sodium cyanide (8.1 mg, 0.16 mmol) in water (0.4 ml) was added; the heterogeneous reaction was warmed to room temperature and then allowed to stir overnight. Tetrahydrofuran (0.4 ml) was then added to solubilize all reactants. Additional sodium cyanide (8 mg, 0.16 mmol) and 2-propylamine (3 drops) were added and stirred overnight. The reaction was filtered and then concentrated under reduced pressure to give title compound 22A-1 (27 mg, 48%) as a colorless solid: +ESI MS (M+1) 506.1; $^1H$ NMR (400 MHz, $CD_2Cl_2$) δ 8.32 (s, 1H), 7.52 (d, J=7.9 Hz, 1H), 7.45–7.33 (m, 5H), 7.21 (d, J=8.7 Hz, 2H), 5.50 (v br s, 2H), 3.88 (v br s, 2H), 3.18 (septuplet, J=6.0 Hz, 1H), 2.16 (m, 2H), 1.82 (ddd, J=13.3, 10.4, 3.7 Hz, 2H), 1.16 (d, J=6.2 Hz, 6H).

Preparation of 1-[9-(4-Chlorophenyl)-8-(2-chlorophenyl)-9H-purin-6-yl]-4-ethylaminopiperidine-4-carbonitrile (22A-2)

22A-2

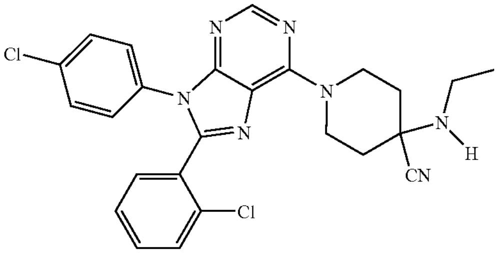

1-[9-(4-Chlorophenyl)-8-(2-chlorophenyl)-9H-purin-6-yl]-4-ethylaminopiperidine-4-carbonitrile was prepared using procedures analogous to those described above for the synthesis of Compound 22A-1. +ESI MS (M+1)=492.1.

EXAMPLE 23

Preparation of 1-[9-(4-Chlorophenyl)-8-(2-chlorophenyl)-9H-purin-6-yl]-4-hydroxypiperidine-4-carboxylic Acid Methyl Ester (23A-1)

23A-1

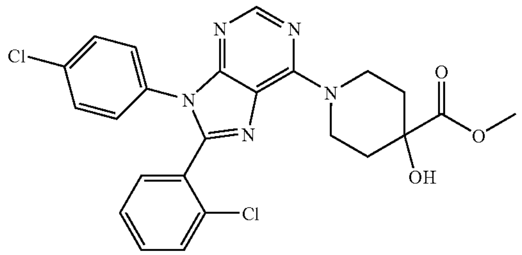

Chloro-9-(4-chlorophenyl)-8-(2-chlorophenyl)-9H-purine I-(4A-7)c (59 mg, 0.16 mmol) and 4-hydroxy-piperidine-4-carboxylic acid (22 mg, 0.14 mmol) were coupled by the general method of Example 19. The crude product (ESI MS (M+1) 484) was dissolved in 1:1 methanol/benzene (0.6 ml) and then treated with trimethylsilyldiazomethane (2 M in hexanes, 0.17 ml, 0.34 mmol). After stirring for 1 hour the reaction was concentrated under a stream of nitrogen and then purified by preparative TLC using 4% methanol in methylene chloride to give title compound 23A-1 (31 mg, 44%). An ether/methylene chloride solution of the material was treated with excess 1 M HCl in ether, concentrated under a stream of nitrogen, and then triturated from ether to give the hydrochloride salt of compound 23A-1 (27 mg, 36% overall) as a light tan solid: +ESI MS (M+1) 498.1; $^1$H NMR (400 MHz, $CD_3OD$) δ 8.38 (s, 1H), 7.62–7.59 (m, 1H), 7.51–7.40 (m, 5H), 7.34 (d, J=8.7 Hz, 2H), 3.90 (v br s, 2H), 3.75 (s, 3H), 2.25 (td, J=13.1, 4.1 Hz, 2H), 1.97 (br d, J=12.4 Hz, 2H).

EXAMPLE 24

Preparation of {1-[9-(4-Chlorophenyl)-8-(2-chlorophenyl)-9-H-purin-6-yl]-4-methylaminopiperidin-4}-methanol (24A-1)

24A-1

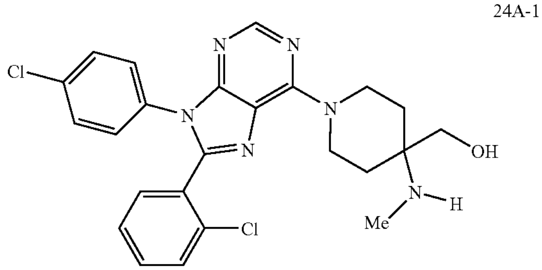

A solution of 1-[9-(4-chlorophenyl)-8-(2-chlorophenyl)-9H-purin-6-yl]-4-methylaminopiperidine-4-carboxylic acid methyl ester 21A-1 (91 mg, 0.18 mmol) in tetrahydrofuran (1.5 ml) at 0° C. was treated with diisobutyl aluminum hydride (1 M in tetrahydrofuran, 0.94 ml) and then warmed to room temperature and allowed to stir overnight. The mixture was quenched with 0.6 M NaOH (25 ml), extracted with ethyl acetate, dried ($Na_2SO_4$), concentrated (80 mg), and then purified on a Biotage™ Flash 12M column using 5–10% methanol and 0.5% $NH_4OH$ in methylene chloride as eluant to give title compound 24A-1 (48 mg, 55%): +ESI MS (M+1) 483.1; $^1$H NMR (400 MHz, $CD_2Cl_2$) δ 8.28 (s, 1H), 7.52 (d, J=8.3 Hz, 1H), 7.44–7.32 (m, 5H), 7.21 (d, J=8.7 Hz, 2H), 4.67 (v br s, 2H), 3.98 (br s, 2H), 3.40 (s, 2H), 2.31 (s, 3H), 1.72 (dt, J=14.1, 4.6 Hz, 2H), 1.62 (ddd, J=14.1, 9.6, 4.2 Hz, 2H).

EXAMPLE 25

Preparation of 8-[9-(4-Chlorophenyl)-8-(2-chlorophenyl)-9H-purin-6-yl]-1-isopropyl-3-methyl-1,3,8-triaza-spiro[4.5]decan-4-one Hydrochloride Salt (25A-1)

25A-1

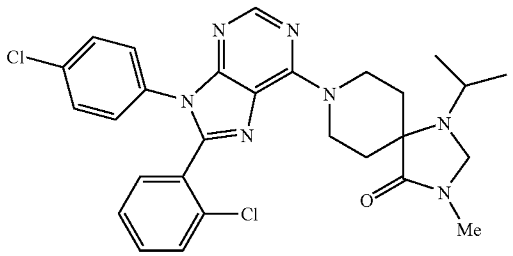

A suspension of 8-[9-(4-chlorophenyl)-8-(2-chlorophenyl)-9H-purin-6-yl]-1-isopropyl-1,3,8-triazaspiro[4.5]decan-4-one 13A-1 (86 mg, 0.16 mmol) and methyl iodide (2 M in MTBE, 16 μl) in 1:1 tetrahydrofuran/dimethylformamide (2 ml) was treated with sodium hydride (60% dispersion in oil, 12 mg, 0.3 mmol). After stirring for 2 hours, the mixture was extracted from saturated aqueous sodium bicarbonate with ethyl acetate, dried ($Na_2SO_4$), concentrated (123 mg), and then purified by flash chromatography using 4% methanol to give title compound 25A-1 as an oil (87 mg, quantitative). A methylene chloride solution of the material was treated with excess 1 M HCl in ether, concentrated under a stream of nitrogen, and then triturated from ether to give the hydrochloride salt of compound 25A-1 (82 mg, 82% overall) as a colorless solid: +ESI MS (M+1) 550.2; $^1$H NMR (400 MHz, $CD_3OD$) δ 8.34 (s, 1H), 7.60 (d, J=7.9 Hz, 1H), 7.51–7.39 (m, 5H), 7.31 (d, J=8.3 Hz, 2H), 4.76 (s, 2H), 4.14 (brs, 2H), 3.78 (brs, 1H), 2.96 (s, 3H), 2.28 (br s, 4H), 1.32 (d, J=6.2 Hz, 6H).

EXAMPLE 26

Preparation of 4-[9-(4-Chlorophenyl)-8-(2-chlorophenyl)-9H-purin-6-yl]-piperazine-2-Carboxylic Acid amide (26A-1)

26A-1

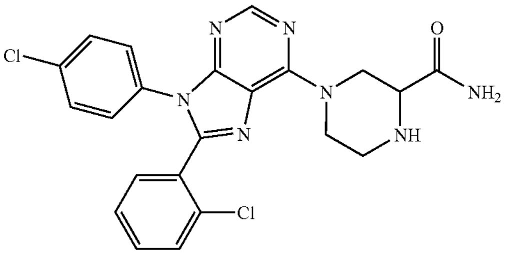

To a 0° C. solution of 4-[9-(4-chlorophenyl)-8-(2-chlorophenyl)-9H-purin-6-yl]-piperazine-2-carboxylic acid ethyl ester 13A-9 (32 mg, 0.064 mmol) in methanol (4 ml) was bubbled $NH_3$ at a moderate rate for 15 minutes. The vessel was sealed, warmed to room temperature and allowed to stir for 4 days. The mixture was concentrated under reduced pressure (123 mg), and then purified on a Biotage™ Flash 12S column using 3–6% methanol in methylene chloride as eluant to give title compound 26A-1 (30 mg, quantitative). A methylene chloride solution of the material was treated with excess 1 M HCl in ether, concentrated under a stream of nitrogen, and then triturated from ether to give the hydrochloride salt of compound 26A-1 as an off-white solid: +ESI MS (M+1) 468.3; $^1H$ NMR (400 MHz, $CD_3OD$) δ 8.47 (s, 1H), 7.64–7.61 (m, 1H), 7.53–7.36 (m, 5H), 7.35 (d, J=8.7 Hz, 2H), 5.52 (br d, J=14.5 Hz, 2H), 4.28 (dd, J=10.0, 3.7 Hz, 1H), 3.95–3.88 (m, 2H), 3.63 (dt, J=12.9, 3.3 Hz, 1H), 3.44–3.39 (m, 1H).

The compounds listed in Table 18 below were prepared using procedures analogous to those described above for the synthesis of Compound 26A-1 using the appropriate starting materials which are available commercially, prepared using preparations well-known to those skilled in the art, or prepared in a manner analogous to routes decribed above for other intermediates. The compounds listed below were isolated initially as the free base and then generally converted to their corresponding hydrochloride salt for testing.

TABLE 18

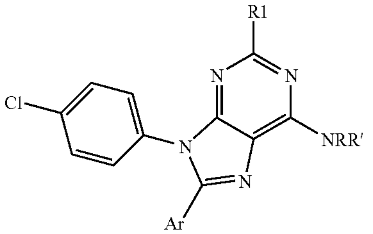

| Ex. No. | Ar | R1 | —NRR' | MS (M + H)+ |
|---|---|---|---|---|
| 26A-2 | 2-chloro-phenyl | —H | 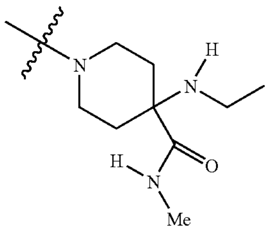 | 524 |

TABLE 18-continued

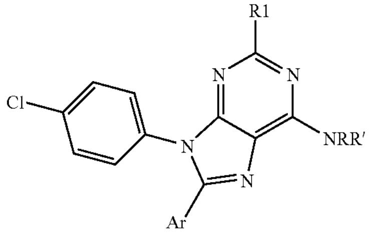

| Ex. No. | Ar | R1 | —NRR' | MS (M + H)+ |
|---|---|---|---|---|
| 26A-3 | 2-chloro-phenyl | —H | 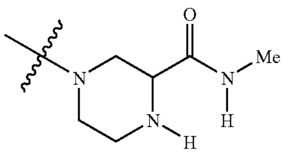 | 482 |

EXAMPLE 27

Preparation of 9-[9-(4-Chlorophenyl)-8-(2-chlorophenyl)-9H-purin-6-yl]-1-methyl-4-oxa-1,9-diaza-spiro[5.5]undecan-2-one (27A-1)

27A-1

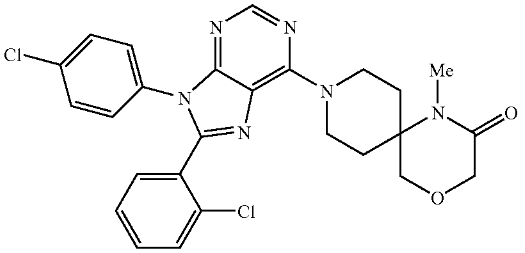

To a 0° C. solution of {1-[9-(4-chlorophenyl)-8-(2-chlorophenyl)-9H-purin-6-yl]-4-methylaminopiperidin-4}-methanol 24A-1 (44 mg, 0.091 mmol) and triethylamine in methylene chloride (1 ml) was added 2-Chloro-acetylchloride, dropwise, and the reaction was allowed to warm to room temperature and stir overnight. The mixture was then diluted to 3 ml with methylene chloride, 50% aqueous NaOH (0.6 ml) was added, and stirring was continued overnight. The reaction was extracted from saturated aqueous sodium bicarbonate with methylene chloride, dried ($Na_2SO_4$), concentrated (123 mg), concentrated under reduced pressure (123 mg), and then purified on a Biotage™ Flash 12S column using 2.5–10% methanol in methylene chloride with 0.5% $NH_4OH$ as eluant to give title compound 27A-1 (15 mg, 32%). A methylene chloride solution of the material was treated with excess 1 M HCl in ether, concentrated under a stream of nitrogen, and then triturated from ether to give the hydrochloride salt of compound 27A-1 as an off-white solid: +ESI MS (M+1) 523.3; $^1$H NMR (400 MHz, $CD_2Cl_2$) δ 8.32 (s, 1H), 7.53 (d, J=7.9 Hz, 1H), 7.45–7.33 (m, 5H), 7.22 (d, J=8.7 Hz, 2H), 5.55 (v br s, 2H), 4.18 (s, 2H), 4.01 (s, 2H), 3.19 (br m, 2H), 2.85 (s, 3H), 2.14 (td, J=13.3, 5.4Hz, 2H), 1.88 (br d, J=14.5Hz, 2H).

EXAMPLE 28

Preparation of 1-[9-(4-Chlorophenyl)-8-(2-chlorophenyl)-9H-purin-6-yl]-3-hydroxyazatidine-3-Carboxylic Acid Methyl Ester (28A-1)

28A-1

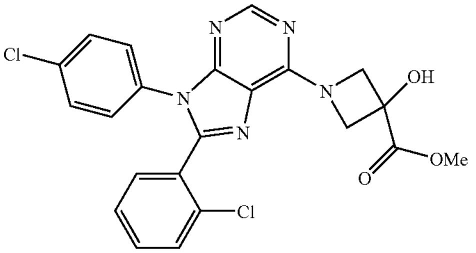

To a 0° C. solution of 1-[9-(4-chlorophenyl)-8-(2-chlorophenyl)-9H-purin-6-yl]-3-hydroxyazaetidine-3-carboxylic acid amide 13A-10 (83 mg, 0.18 mmol) in methanol (2 ml) was added HCl (1 M in ether, 0.27 ml). After 15 minutes, the reaction was concentrated under reduced pressure. The crude product was purified by Chromatotron using 30:1:0.05 to 20:1:0.1 methylene chloride/methanol/$NH_4OH$ as the eluant (14 mg, 17%): +ESI MS (M+1) 470.2; $^1$H NMR (400 MHz, $CD_3OD$) δ 8.25 (s, 1H), 7.61 (d, J=7.5 Hz, 1H), 7.48–7.39 (m, 5H), 7.30 (d, J=8.7 Hz, 2H), 3.83 (s, 3H).

EXAMPLE 29

Preparation of 1-{1-[9-(4-Chlorophenyl)-8-(2-chlorophenyl)-9H-purin-6-yl]-4-phenylpiperidin-4-yl}-ethanone (29A-1)

29A-1

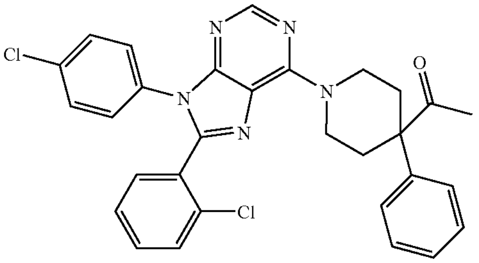

To a solution of 6-Chloro-9-(4-chlorophenyl)-8-(2-chlorophenyl)-9H-purine I-(4A-7)c (68 mg, 0.18 mmol) in 1:1 methylene chloride/ethanol (2 ml) was added 1-(4-phenylpiperidin-4-yl)-ethanone (48 mg, 0.2 mmol) and triethylamine (70 μl, 0.5 mmol). The mixture was stirred overnight, concentrated under reduced pressure, and then purified on a Biotage™ Flash 12S column using 5–10% methanol in methylene chloride as eluant to give title compound 29A-1 (77 mg, 78%).

A 1:1 methanol/methylene chloride solution of the material was treated with excess 1 M HCl in ether, concentrated under a stream of nitrogen, and then triturated from ether to give the hydrochloride salt of compound 29A-1 (77 mg): +ESI MS (M+1) 542.5; $^1$H NMR (400 MHz, $CD_3OD$) δ 8.35 (s, 1h), 7.60 (d, J=8.7 Hz, 1H), 7.51 (t, J=7.8 Hz, 1H), 7.46–7.40 (m, 9H), 7.34–7.29 (m, 3H), 2.70 (br m, 2H), 1.98 (br m, 2H).

The compounds listed in Table 19 below were prepared using procedures analogous to those described above for the synthesis of Compound 29A-1 using the appropriate starting materials which are available commercially, prepared using preparations well-known to those skilled in the art, or prepared in a manner analogous to routes decribed above for other intermediates. The compounds listed below were isolated initially as the free base and then generally converted to their corresponding hydrochloride salt for testing.

TABLE 19

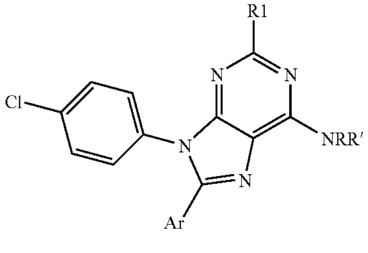

| Ex. No. | Ar | R1 | —NRR' | MS $(M + H)^+$ |
|---|---|---|---|---|
| 29A-2 | 2-chlorophenyl | —H | 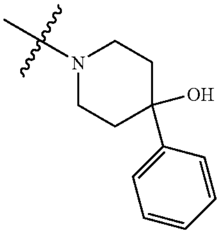 | 516 |

TABLE 19-continued
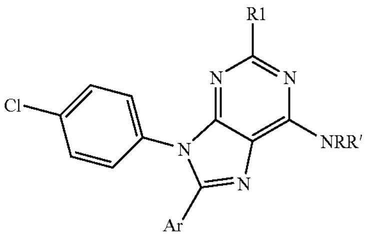
| Ex. No. | Ar | R1 | —NRR' | MS (M + H)+ |
|---|---|---|---|---|
| 29A-3 | 2-chlorophenyl | —H | 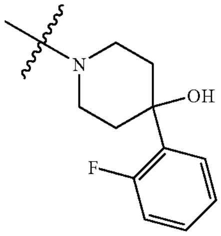 | 534 |
| 29A-4 | 2-chlorophenyl | —H | 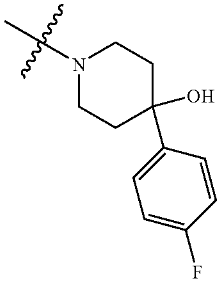 | 534 |
| 29A-5 | 2-chlorophenyl | —H | 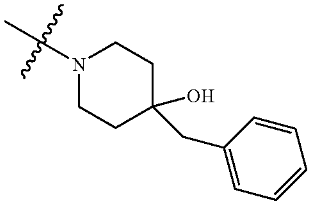 | 530 |
| 29A-6 | 2-chlorophenyl | H | 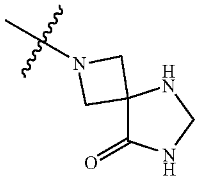 | 466.1 |
| 29A-7 | 2-chlorophenyl | H | 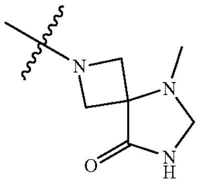 | 480.1 |

TABLE 19-continued

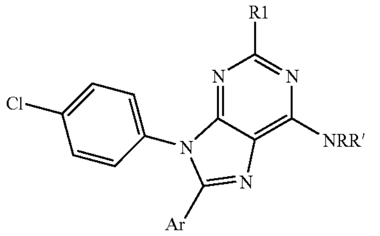

| Ex. No. | Ar | R1 | —NRR' | MS $(M + H)^+$ |
|---|---|---|---|---|
| 29A-8 | 2-chlorophenyl | H | 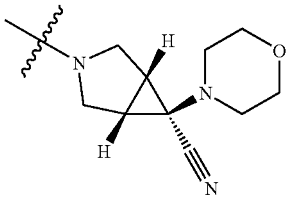 | 532.4 |

EXAMPLE 30

Preparation of 3-[9-(4-Chlorophenyl)-8-(2-chlorophenyl)-9H-purin-6-yl]-6-morpholin-4-yl-3-azabicyclo[3.1.0]hexane-6-Carboxylic Acid Amide (30A-1)

30A-1

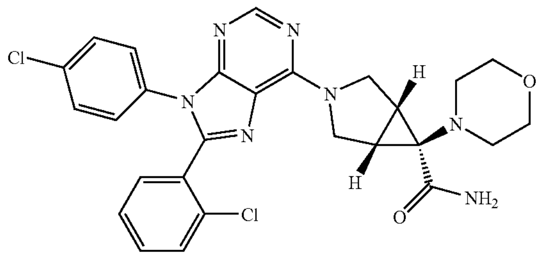

A mixture of 3-[9-(4-chlorophenyl)-8-(2-chlorophenyl)-9H-purin-6-yl]-6-morpholin-4-yl-3-azabicyclo[3.1.0]hexane-6-carbonitrile 29A-8 (28 mg, 0.052 mmol) in concentrated $H_2SO_4$ (0.6 ml) was heated at 200° C. for two hours. After the reaction mixture was allowed to cool to room temperature and stir overnight, it was cooled in an ice bath and then carefully quenched with 5 M aqueous NaOH to pH 11. The mixture was extracted with ethyl acetate and then the combined organic layers were washed with brine, dried ($MgSO_4$) and concentrated, in vacuo. The residue was purified on a Biotage™ Flash 12S column using 0–6% methanol in methylene chloride as eluant to give, after trituration from methylene chloride/hexanes, title compound 30A-1 (24 mg, 83%): +ESI MS (M+1) 550.4; $^1H$ NMR (400 MHz, $CD_2Cl_2$) δ 8.27 (s, 1H), 7.52–7.49 (m, 1H), 7.44–7.32 (m, 5H), 7.20 (d, J=8.7 Hz, 2H), 5.54 (s, 1H), 5.47 (s, 1H), 5.03 (d, J=12.0 Hz, 1H), 4.37 (d, J=12.0 Hz, 1H), 3.97 (br d, J=9.1 Hz, 1H), 3.68–3.55 (m, 5H), 2.73–2.63 (m, 4H), 2.01 (br s, 1H), 1.96 (br s, 1H).

EXAMPLE 31

Preparation of 9-(4-Chlorophenyl)-8-(2-chlorophenyl)-6-isopropoxy-9H-purine (31A-1)

31A-1

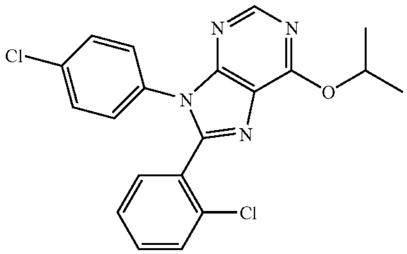

9-(4-Chlorophenyl)-8-(2-chlorophenyl)-9H-purin-6-ol (I-(4A-7)b; 50 mg, 0.14 mmol), 2-iodopropane (26 mg, 0.15 mmol), and cesium carbonate (50 mg, 0.15 mmol) were combined in dimethylformamide (0.7 ml) and stirred overnight. Additional 2-iodopropane (13 mg, 0.76 mmol), and cesium carbonate (25 mg, 0.76 mmol) were added and stirred an addional day. The reaction mixture was diluted with ethyl ether and then washed with saturated aqueous sodium bicarbonate and brine. The organic layer was dried ($Na_2SO_4$), evaporated to dryness, and then purified on a Biotage™ Flash 12S column using 0–70% ethyl acetate in hexanes as eluant to afford title compound 31A-1 (34 mg, 56%); $^1H$ NMR: +ESI MS (M+1) 399.4; (400 MHz, $CD_2Cl_2$) δ 8.51 (s, 1H), 7.56 (dd, J=7.5, 1.7 Hz, 1H), 7.47–7.34 (m, 5H), 7.23 (d, J=9.1 Hz, 2H), 5.71 (septuplet, J=6.2 Hz, 1H), 1.50 (d, J=6.2 Hz, 6H).

The compounds listed in Table 1 below were prepared using procedures analogous to those described above for the synthesis of Compound 31A-1 using the appropriate starting materials which are available commercially, prepared using preparations well-known to those skilled in the art, or prepared in a manner analogous to routes decribed above for other intermediates.

TABLE 20

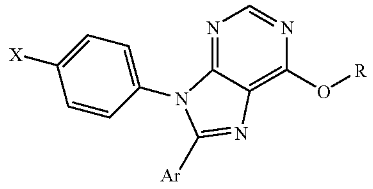

| Example No. | Ar | X | —OR | MS (M + H)+ |
|---|---|---|---|---|
| 31A-2 | 2-chlorophenyl | $CF_3$ | —OEt | 419.2 |
| 31A-3 | 4-chlorophenyl | $CF_3$ | —OEt | 419.2 |
| 31A-4 | 2-methylphenyl | $CF_3$ | —OEt | 399.3 |
| 31A-5 | 3-chlorophenyl | Cl | —OEt | 385.2 |
| 31A-6 | 4-chlorophenyl | Cl | —OEt | 385.2 |
| 31A-7 | 2-methylphenyl | Cl | —OEt | 365.4 |
| 31A-8 | 2-chlorophenyl | $CF_3$ | —OiPr | 433.3 |
| 31A-9 | 4-chlorophenyl | $CF_3$ | —OiPr | 433.4 |
| 31A-10 | 2-methylphenyl | $CF_3$ | —OiPr | 413.4 |
| 31A-11 | 4-chlorophenyl | Cl | —OiPr | 399.4 |
| 31A-12 | 2-methylphenyl | Cl | —OiPr | 379.4 |
| 31A-13 | 2-chlorophenyl | $CF_3$ | —$OCH_2CF_3$ | 473.4 |
| 31A-14 | 3-chlorophenyl | $CF_3$ | —$OCH_2CF_3$ | 473.4 |
| 31A-15 | 4-chlorophenyl | $CF_3$ | —$OCH_2CF_3$ | 473.4 |
| 31A-16 | 2-methylphenyl | $CF_3$ | —$OCH_2CF_3$ | 453.4 |
| 31A-17 | 3-chlorophenyl | Cl | —$OCH_2CF_3$ | 439.3 |
| 31A-18 | 2-methylphenyl | Cl | —$OCH_2CF_3$ | 419.1 |

EXAMPLE 32

Preparation of 1-[9-(4-Chlorophenyl)-8-(2-chlorophenyl)-9H-purin-6-yl]-piperidin-4-one oxime (32A-1)

32A-1

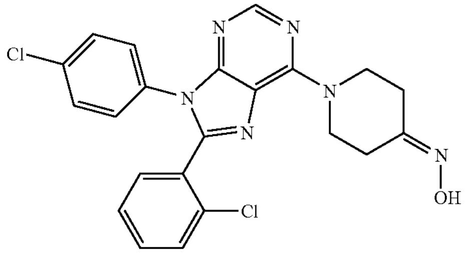

A mixture of 1-[9-(4-chlorophenyl)-8-(2-chlorophenyl)-9H-purin-6-yl]-piperidin-4-one 7A-96 (75 mg, 0.17 mmol) and hydroxylamine hydrochloride (11.9 mg, 0.17 mmol) in methanol (0.3 ml) was stirred overnight at room temperature. The reaction was then extracted from saturated aqueous sodium bicarbonate, the combined organic layers were dried ($Na_2SO_4$) and concentrated to afford title compound 32A-1 (75 mg, 97%) as a solid: +ESI MS (M+1) 453.4; $^1H$ NMR (400 MHz, DMSO-$d_6$) δ 10.49 (s, 1H), 8.28 (s, 1H), 7.70 (dd, J=7.7, 1.5 Hz, 1H), 7.53–7.41 (m, 5H), 7.31 (d, J=8.7 Hz, 2H), 4.45–4.18 (v br s, 4H), 2.61 (t, J=6.0 Hz, 2H), 2.39 (t, J=5.8 Hz, 2H).

Pharmacological Testing

The utility of the compounds of the present invention in the practice of the instant invention can be evidenced by activity in at least one of the protocols described hereinbelow. The following acronyms are used in the protocols described below.

BSA—bovine serum albumin

DMSO—dimethylsulfoxide

EDTA—ethylenediamine tetracetic acid

PBS—phosphate-buffered saline

EGTA—ethylene glycol-bis(β-aminoethyl ether) N,N,N',N'-tetraacetic acid

GDP—guanosine diphosphate sc—subcutaneous po—orally ip—intraperitoneal icv—intra cerebro ventricular iv—intravenous

[$^3H$]SR141716A—radiolabeled N-(piperidin-1-yl)-5-(4-chlorophenyl)-1-(2,4-dichlorophenyl)-4-methyl-1H-pyrazole-3-carboxamide hydrochloride available from Amersham Biosciences, Piscataway, N.J.

[$^3H$]CP-55940—radiolabled 5-(1,1-dimethylheptyl)-2-[5-hydroxy-2-(3-hydroxypropyl)-cyclohexyl]-phenol available from NEN Life Science Products, Boston, Mass.

AM251—N-(piperidin-1-yl)-1-(2,4-dichlorophenyl)-5-(4-iodophenyl)-4-methyl-1H-pyrazole-3-carboxamide available from Tocris™, Ellisville, Mo.

All of the compounds listed in the Example section above were tested in the CB-1 receptor binding assay below. The compounds provided a range of binding activities from 0.17 nM to 1 μM with the exception of Example 19A-1 which had a binding activity of 2.8 nM and Example 19A-2 which demonstrated a binding activity of 1.2 nM. Those compounds having an activity <20 nM were then tested in the CB-1 GTPγ[$^{35}S$] Binding Assay and the CB-2 binding assay described below in the Biological Binding Assays section. Selected compounds were then tested in vivo using one or more of the functional assays described in the Biological Functional Assays section below.

In Vitro Biological Assays

Bioassay systems for determining the CB-1 and CB-2 binding properties and pharmacological activity of cannabinoid receptor ligands are described by Roger G. Pertwee in "Pharmacology of Cannabinoid Receptor Ligands" *Current Medicinal Chemistry,* 6, 635–664 (1999) and in WO 92/02640 (U.S. application Ser. No. 07/564,075 filed Aug. 8, 1990, incorporated herein by reference).

The following assays were designed to detect compounds that inhibit the binding of [$^3H$] SR141716A (selective radiolabeled CB-1 ligand) and [$^3H$] 5-(1,1-dimethylheptyl)-2-[5-hydroxy-2-(3-hydroxypropyl)-cyclohexyl]-phenol ([$^3H$] CP-55940; radiolabeled CB-1/CB-2 ligand) to their respective receptors.

Rat CB-1 Receptor Binding Protocol

PelFreeze brains (available from Pel Freeze Biologicals, Rogers, Ark.) were cut up and placed in tissue preparation buffer (5 mM Tris HCl, pH=7.4 and 2 mM EDTA), polytroned at high speed and kept on ice for 15 minutes. The homogenate was then spun at 1,000×g for 5 minutes at 4° C. The supernatant was recovered and centrifuged at 100,000×G for 1 hour at 4° C. The pellet was then re-suspended in 25 ml of TME (25 nM Tris, pH=7.4, 5 mM $MgCl_2$, and 1 mM EDTA) per brain used. A protein assay was performed and 200 μl of tissue totaling 20 μg was added to the assay.

The test compounds were diluted in drug buffer (0.5% BSA, 10% DMSO and TME) and then 25 μl were added to a deep well polypropylene plate. [$^3$H] SR141716A was diluted in a ligand buffer (0.5% BSA plus TME) and 25 μl were added to the plate. A BCA protein assay was used to determine the appropriate tissue concentration and then 200 μl of rat brain tissue at the appropriate concentration was added to the plate. The plates were covered and placed in an incubator at 20° C. for 60 minutes. At the end of the incubation period 250 μl of stop buffer (5% BSA plus TME) was added to the reaction plate. The plates were then harvested by Skatron onto GF/B filtermats presoaked in BSA (5 mg/ml) plus TME. Each filter was washed twice. The filters were dried overnight. In the morning the filters were counted on a Wallac Betaplate™ counter (available from PerkinElmer Life Sciences™, Boston, Mass.).

Human CB-1 Receptor Binding Protocol

Human embryonic kidney 293 (HEK 293) cells transfected with the CB-1 receptor cDNA (obtained from Dr. Debra Kendall, University of Connecticut) were harvested in homogenization buffer (10 mM EDTA, 10 mM EGTA, 10 mM Na Bicarbonate, protease inhibitors; pH=7.4), and homogenized with a Dounce Homogenizer. The homogenate was then spun at 1,000×g for 5 minutes at 4° C. The supernatant was recovered and centrifuged at 25,000×G for 20 minutes at 4° C. The pellet was then re-suspended in 10 ml of homogenization buffer and re-spun at 25,000×G for 20 minutes at 4° C. The final pellet was re-suspended in 1 ml of TME (25 mM Tris buffer (pH=7.4) containing 5 mM $MgCl_2$ and 1 mM EDTA). A protein assay was performed and 200 μl of tissue totaling 20 μg was added to the assay.

The test compounds were diluted in drug buffer (0.5% BSA, 10% DMSO and TME) and then 25 μl were added to a deep well polypropylene plate. [3H] SR141716A was diluted in a ligand buffer (0.5% BSA plus TME) and 25 μl were added to the plate. The plates were covered and placed in an incubator at 30° C. for 60 minutes. At the end of the incubation period 250 μl of stop buffer (5% BSA plus TME) was added to the reaction plate. The plates were then harvested by Skatron onto GF/B filtermats presoaked in BSA (5 mg/ml) plus TME. Each filter was washed twice. The filters were dried overnight. In the morning the filters were counted on a Wallac Betaplate™ counter (available from PerkinElmer Life Sciences™, Boston, Mass.).

CB-2 Receptor Binding Protocol

Chinese hamster ovary-K1 (CHO-K1) cells transfected with CB-2 cDNA (obtained from Dr. Debra Kendall, University of Connecticut) were harvested in tissue preparation buffer (5 mM Tris-HCl buffer (pH=7.4) containing 2 mM EDTA), polytroned at high speed and kept on ice for 15 minutes. The homogenate was then spun at 1,000×g for 5 minutes at 4° C. The supernatant was recovered and centrifuged at 100,000×G for 1 hour at 4° C. The pellet was then re-suspended in 25 ml of TME (25 mM Tris buffer (pH=7.4) containing 5 mM $MgCl_2$ and 1 mM EDTA) per brain used. A protein assay was performed and 200 μl of tissue totaling 10 μg was added to the assay.

The test compounds were diluted in drug buffer (0.5% BSA, 10% DMSO, and 80.5% TME) and then 25 μl were added to the deep well polypropylene plate. [3H] CP-55940 was diluted a ligand buffer (0.5% BSA and 99.5% TME) and then 25 μl were added to each well at a concentration of 1 nM. A BCA protein assay was used to determine the appropriate tissue concentration and 200 μl of the tissue at the appropriate concentration was added to the plate. The plates were covered and placed in an incubator at 30° C. for 60 minutes. At the end of the incubation period 250 μl of stop buffer (5% BSA plus TME) was added to the reaction plate. The plates were then harvested by Skatron format onto GF/B filtermats presoaked in BSA (5 mg/ml) plus TME. Each filter was washed twice. The filters were dried overnight. The filters were then counted on the Wallac Betaplate™ counter.

CB-1 GTPγ [$^{35}$S] Binding Assay

Membranes were prepared from CHO-K1 cells stably transfected with the human CB-1 receptor cDNA. Membranes were prepared from cells as described by Bass et al, in "Identification and characterization of novel somatostatin antagonists," *Molecular Pharmacology,* 50, 709–715 (1996). GTPγ [$^{35}$S] binding assays were performed in a 96 well FlashPlate™ format in duplicate using 100 pM GTPγ [$^{35}$S] and 10 μg membrane per well in assay buffer composed of 50 mM Tris HCl, pH 7.4, 3 mM $MgCl_2$, pH 7.4, 10 mM $MgCl_2$, 20 mM EGTA, 100 mM NaCl, 30 μM GDP, 0.1% bovine serum albumin and the following protease inhibitors: 100 μg/ml bacitracin, 100 μg/ml benzamidine, 5 μg/ml aprotinin, 5 μg/ml leupeptin. The assay mix was then incubated with increasing concentrations of antagonist ($10^{-10}$ M to $10^{-5}$ M) for 10 minutes and challenged with the cannabinoid agonist CP-55940 (10 μM). Assays were performed at 30° C. for one hour. The FlashPlates™ were then centrifuged at 2000×g for 10 minutes. Stimulation of GTPγ [$^{35}$S] binding was then quantified using a Wallac Microbeta.$EC_{50}$ calculations done using Prism™ by Graphpad.

Inverse agonism was measured in the absense of agonist.

CB-1 FLIPR-Based Functional Assay Protocol

CHO-K1 cells co-transfected with the human CB-1 receptor cDNA (obtained from Dr. Debra Kendall, University of Connecticut) and the promiscuous G-protein G16 were used for this assay. Cells were plated 48 hours in advance at 12500 cells per well on collagen coated 384 well black clear assay plates. Cells were incubated for one hour with 4 μM Fluo-4 AM (Molecular Probes) in DMEM (Gibco) containing 2.5 mM probenicid and pluronic acid (0.04%). The plates were then washed 3 times with HEPES-buffered saline (containing probenicid; 2.5 mM) to remove excess dye. After 20 min the plates were added to the FLIPR individually and fluorescence levels was continuously monitored over an 80 second period. Compound additions were made simultaneously to all 384 wells after 20 seconds of baseline. Assays were performed in triplicate and 6 point concentration-response curves generated. Antagonist compounds were subsequently challenged with 3 μM WIN 55,212-2 (agonist). Data were analyzed using Graph Pad Prism.

Detection of Inverse Agonists

The following cyclic-AMP assay protocol using intact cells was used to determine inverse agonist activity.

Cells were plated into a 96-well plate at a plating density of 10,000–14,000 cells per well at a concentration of 100 μl per well. The plates were incubated for 24 hours in a 37° C. incubator. The media was removed and media lacking serum (100 μl) was added. The plates were then incubated for 18 hours at 37° C.

Serum free medium containing 1 mM IBMX was added to each well followed by 10 μl of test compound (1:10 stock solution (25 mM compound in DMSO) into 50% DMSO/PBS) diluted 10× in PBS with 0.1% BSA. After incubating for 20 minutes at 37° C., 2 μM of Forskolin was added and then incubated for an additional 20 minutes at 37° C. The media was removed, 100 μl of 0.01 N HCl was added and then incubated for 20 minutes at room temperature. Cell lysate (75 μl) along with 25 μl of assay buffer (supplied in FlashPlate™ cAMP assay kit available from NEN Life Science Products Boston, Mass.) into a Flashplate. cAMP standards and cAMP tracer were added following the kit's protocol. The flashplate was then incubated for 18 hours at 4° C. The content of the wells were aspirated and counted in a Scintillation counter.

In Vivo Biological Assays

Cannabinoid agoinists such as $\Delta^9$-tetrahydrocannabinol ($\Delta^9$-THC) and CP-55940 have been shown to affect four characteristic behaviors in mice, collectively known as the Tetrad. For a description of these behaviors see: Smith, P. B., et al. in "The pharmacological activity of anandamide, a putative endogenous cannabinoid, in mice." *J. Pharmacol. Exp. Ther.,* 270(1), 219–227 (1994) and Wiley, J., et al. in "Discriminative stimulus effects of anandamide in rats," *Eur. J. Pharmacol.,* 276(1–2), 49–54 (1995). Reversal of these activities in the Locomotor Activity, Catalepsy, Hypothermia, and Hot Plate assays described below provides a screen for in vivo activity of CB-1 antagonists.

All data is presented as % reversal from agonist alone using the following formula: (CP/agonist—vehicle/agonist)/(vehicle/vehicle—vehicle/agonist). Negative numbers indicate a potentiation of the agonist activity or non-antagonist activity. Positive numbers indicate a reversal of activity for that particular test.

Locomotor Activity

Male ICR mice (n=6; 17–19 g, Charles River Laboratories, Inc., Wilmington, Mass.) were pre-treated with test compound (sc, po, ip, or icv). Fifteen minutes later, the mice were challenged with CP-55940 (sc). Twenty-five minutes after the agonist injection, the mice were placed in clear acrylic cages (431.8 cm×20.9 cm×20.3 cm) containing clean wood shavings. The subjects were allowed to explore surroundings for a total of about 5 minutes and the activity was recorded by infrared motion detectors (available from Coulbourn Instruments™, Allentown, Pa.) that were placed on top of the cages. The data was computer collected and expressed as "movement units."

Catalepsy

Male ICR mice (n=6; 17–19 g upon arrival) were pre-treated with test compound (sc, po, ip or icv). Fifteen minutes later, the mice were challenged with CP-55940 (sc). Ninety minutes post injection, the mice were placed on a 6.5 cm steel ring attached to a ring stand at a height of about 12 inches. The ring was mounted in a horizontal orientation and the mouse was suspended in the gap of the ring with fore- and hind-paws gripping the perimeter. The duration that the mouse remained completely motionless (except for respiratory movements) was recorded over a 3-minute period.

The data were presented as a percent immobility rating. The rating was calculated by dividing the number of seconds the mouse remains motionless by the total time of the observation period and multiplying the result by 100. A percent reversal from the agonist was then calculated.

Hypothermia

Male ICR mice (n=5; 17–19 g upon arrival) were pretreated with test compounds (sc, po, ip or icv). Fifteen minutes later, mice were challenged with the cannabinoid agonist CP-55940 (sc). Sixty-five minutes post agonist injection, rectal body temperatures were taken. This was done by inserting a small thermostat probe approximately 2–2.5 cm into the rectum. Temperatures were recorded to the nearest tenth of a degree.

Hot Plate

Male ICR mice (n=7; 17–19 g upon arrival) are pretreated with test compounds (sc, po, ip or iv). Fifteen minutes later, mice were challenged with a cannabinoid agonist CP-55940 (sc). Forty-five minutes later, each mouse was tested for reversal of analgesia using a standard hot plate meter (Columbus Instruments). The hot plate was 10"×10"×0.75" with a surrounding clear acrylic wall. Latency to kick, lick or flick hindpaw or jump from the platform was recorded to the nearest tenth of a second. The timer was experimenter activated and each test had a 40 second cut off. Data were presented as a percent reversal of the agonist induced analgesia.

Food Intake

The following screen was used to evaluate the efficacy of test compounds for inhibiting food intake in Sprague-Dawley rats after an overnight fast.

Male Sprague-Dawley rats were obtained from Charles River Laboratories, Inc. (Wilmington, Mass.). The rats were individually housed and fed powdered chow. They were maintained on a 12-hour light/dark cycle and received food and water ad libitum. The animals were acclimated to the vivarium for a period of one week before testing was conducted. Testing was completed during the light portion of the cycle.

To conduct the food intake efficacy screen, rats were transferred to individual test cages without food the afternoon prior to testing, and the rats were fasted overnight. After the overnight fast, rats were dosed the following morning with vehicle or test compounds. A known antagonist was dosed (3 mg/kg) as a positive control, and a control group received vehicle alone (no compound). The test compounds were dosed at ranges between 0.1 and 100 mg/kg depending upon the compound. The standard vehicle was 0.5% (w/v) methylcellulose in water and the standard route of administration was oral. However, different vehicles and routes of administration were used to accommodate various compounds when required. Food was provided to the rats 30 minutes after dosing and the Oxymax automated food intake system (Columbus Instruments, Columbus, Ohio) was started. Individual rat food intake was recorded continuously at 10-minute intervals for a period of two hours. When required, food intake was recorded manually using an electronic scale; food was weighed every 30 minutes after food was provided up to four hours after food was provided. Compound efficacy was determined by comparing the food intake pattern of compound-treated rats to vehicle and the standard positive control.

Alcohol Intake

The following protocol evaluates the effects of alcohol intake in alcohol preferring (P) female rats (bred at Indiana University) with an extensive drinking history. The following references provide detailed descriptions of P rats: Li, T. -K., et al., "Indiana selection studies on alcohol related behaviors" in *Development of Animal Models as Pharmacogenetic Tools* (eds McClearn C. E., Deitrich R. A. and Erwin V. G.), Research Monograph 6, 171–192 (1981) NIAAA, ADAMHA, Rockville, Md.; Lumeng, L, et al., "New strains of rats with alcohol preference and nonpreference" *Alcohol And Aldehyde Metabolizing Systems,* 3, Academic Press, New York, 537–544 (1977); and Lumeng, L, et al., "Different sensitivities to ethanol in alcohol-preferring and -nonpreferring rats," *Pharmacol, Biochem Behav.,* 16, 125–130 (1982).

Female rats were given 2 hours of access to alcohol (10% v/v and water, 2-bottle choice) daily at the onset of the dark cycle. The rats were maintained on a reverse cycle to facilitate experimenter interactions. The animals were initially assigned to four groups equated for alcohol intakes: Group 1—vehicle (n=8); Group 2—positive control (e.g., 5.6 mg/kg AM251; n=8); Group 3—low dose test compound (n=8); and Group 4—high dose of test compound (n=8). Test compounds were generally mixed into a vehicle of 30% (w/v) β-cyclodextrin in distilled water at a volume of 1–2 ml/kg. Vehicle injections were given to all groups for the first two days of the experiment. This was followed by 2 days of drug injections (to the appropriate groups) and a final day of vehicle injections. On the drug injection days, drugs were given sc 30 minutes prior to a 2-hour alcohol access period. Alcohol intake for all animals was measured during the test period and a comparison was made between drug and vehicle-treated animals to determine effects of the compounds on alcohol drinking behavior.

Additional drinking studies were done utilizing female C57Bl/6 mice (Charles River). Several studies have shown that this strain of mice will readily consume alcohol with little to no manipulation required (Middaugh et al., "Ethanol Consumption by C57BL/6 Mice: Influence of Gender and Procedural Variables" *Alcohol,* 17 (3), 175–183, 1999; Le et al., "Alcohol Consumption by C57BL/6, BALA/c, and DBA/2 Mice in a Limited Access Paradigm" *Pharmacology Biochemisrty and Behavior,* 47, 375–378, 1994).

For our purposes, upon arrival (17–19 g) mice were individually housed and given unlimited access to powdered rat chow, water and a 10% (w/v) alcohol solution. After 2–3 weeks of unlimited access, water was restricted for 20 hours and alcohol was restricted to only 2 hours access daily. This was done in a manner that the access period was the last 2 hours of the dark part of the light cycle.

Once drinking behavior stabilized, testing commenced. Mice were considered stable when the average alcohol consumption for 3 days was ±20% of the average for all 3 days. Day 1 of test consisted of all mice receiving vehicle injection (sc or ip). Thirty to 120 minutes post injection access was given to alcohol and water. Alcohol consumption for that day was calculated (g/kg) and groups were assigned (n=7–10) so that all groups had equivocal alcohol intake. On day 2 and 3, mice were injected with vehicle or test compound and the same protocol as the previous day was followed. Day 4 was wash out and no injections were given. Data was analyzed using repeated measures ANOVA. Change in water or alcohol consumption was compared back to vehicle for each day of the test. Positive results would be interpreted as a compound that was able to significantly reduce alcohol consumption while having no effect on water.

Oxygen Consumption

Methods:

Whole body oxygen consumption is measured using an indirect calorimeter (Oxymax from Columbus Instruments, Columbus, Ohio) in male Sprague Dawley rats (if another rat strain or female rats are used, it will be specified). Rats (300–380 g body weight) are placed in the calorimeter chambers and the chambers are placed in activity monitors. These studies are done during the light cycle. Prior to the measurement of oxygen consumption, the rats are fed standard chow ad libitum. During the measurement of oxygen consumption, food is not available. Basal pre-dose oxygen consumption and ambulatory activity are measured every 10 minutes for 2.5 to 3 hours. At the end of the basal pre-dosing period, the chambers are opened and the animals are administered a single dose of compound (the usual dose range is 0.001 to 10 mg/kg) by oral gavage (or other route of administration as specified, i.e., sc, ip, iv). Drugs are prepared in methylcellulose, water or other specified vehicle (examples include PEG400, 30% beta-cyclodextran and propylene glycol). Oxygen consumption and ambulatory activity are measured every 10 minutes for an additional 1–6 hours post-dosing.

The Oxymax calorimeter software calculates the oxygen consumption (ml/kg/h) based on the flow rate of air through the chambers and difference in oxygen content at inlet and output ports. The activity monitors have 15 infrared light beams spaced one inch apart on each axis, ambulatory activity is recorded when two consecutive beams are broken and the results are recorded as counts.

Resting oxygen consumption, during pre- and post-dosing, is calculated by averaging the 10-min $O_2$ consumption values, excluding periods of high ambulatory activity (ambulatory activity count >100) and excluding the first 5 values of the pre-dose period and the first value from the post-dose period. Change in oxygen consumption is reported as percent and is calculated by dividing the post-dosing resting oxygen consumption by the pre-dose oxygen consumption *100. Experiments will typically be done with n=4–6 rats and results reported are mean +/−SEM.

Interpretation:

An increase in oxygen consumption of >10% is considered a positive result. Historically, vehicle-treated rats have no change in oxygen consumption from pre-dose basal.

What is claimed is:

1. A compound of Formula (I)

(I)

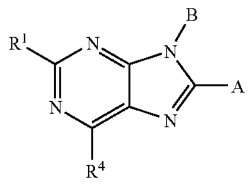

wherein

A and B are each independently a substituted phenyl;

$R^1$ is hydrogen, $(C_1–C_4)$alkyl, halo-substituted $(C_1–C_4)$alkyl, or $(C_1–C_4)$alkoxy;

$R^4$ is (i) a group having Formula (IA) or Formula (IB)

(IA)

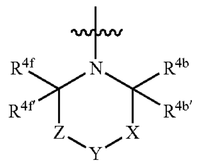

(IB)

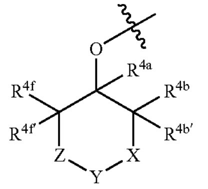

where $R^{4a}$ is hydrogen or $(C_1-C_3)$alkyl;

$R^{4b}$ is hydrogen, an optionally substituted $(C_1-C_3)$alkyl, or taken together with $R^{4e}$, $R^{4e'}$, $R^{4f}$, or $R^{4f'}$ forms a bond, a methylene bridge, or an ethylene bridge;

$R^{4b'}$ is hydrogen, an optionally substituted $(C_1-C_3)$alkyl, or taken together with $R^{4e}$, $R^{4e'}$, $R^{4f}$, or $R^{4f'}$ forms a bond, a methylene bridge, or an ethylene bridge;

X is a bond, $—CH_2CH_2—$, or $—C(R^{4c})(R^{4c'})—$, where $R^{4c}$ and $R^{4c'}$ are each independently hydrogen, cyano, hydroxy, amino, $H_2NC(O)—$, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)alkyl)_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3- to 6-membered heterocycle, and a partially or fully saturated 3- to 8-membered carbocyclic ring, where said chemical moiety is optionally substituted, or either $R^{4c}$ or $R^{4c'}$ taken together with $R^{4e}$, $R^{4e'}$, $R^{4f}$, or $R^{4f'}$ forms a bond, a methylene bridge or an ethylene bridge;

Y is oxygen, sulfur, —C(O)—, —C(=N—OH)—, or $—C(R^{4d})(R^{4d'})—$, where $R^{4d}$ and $R^{4d'}$ are each independently hydrogen, cyano, hydroxy, amino, $H_2NC(O)—$, or a chemical moiety selected from the group consisting of $(C_1-C_6)$alkyl, $(C_1-C_6)$alkoxy, acyloxy, acyl, $(C_1-C_3)$alkyl-OC—(O)—, $(C_1-C_4)$alkyl-NH—C(O)—, $((C_1-C_4)alkyl)_2$N—C(O)—, HO—NH—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3- to 6-membered heterocycle, and a partially or fully saturated 3- to 8-membered carbocyclic ring, where said chemical moiety is optionally substituted, or $R^{4d}$ and $R^{4d'}$ taken together form a partially or fully saturated, 3- to 6-membered heterocyclic ring, a 5- or 6-membered lactone ring, or a 4- to 6-membered lactam ring, where said heterocyclic ring, said lactone ring and said lactam ring are optionally substituted and said lactone ring and said lactam ring optionally contain an additional heteroatom selected from oxygen, nitrogen or sulfur, or Y is $—NR^{4d''}—$, where $R^{4d''}$ is a hydrogen or a chemical moiety selected from the group consisting of $(C_1-C_6)$alkyl, $(C_3-C_6)$cycloalkyl, $(C_1-C_3)$alkylsulfonyl-, $(C_1-C_3)$alkylaminosulfonyl-, di$(C_1-C_3)$alkylaminosulfonyl-, acyl, $(C_1-C_6)$alkyl-O—C(O)—, aryl, and heteroaryl, where said chemical moiety is optionally substituted;

Z is a bond, $—CH_2CH_2—$, or $—C(R^{4e})(R^{4e'})—$, where $R^{4e}$ and $R^{4e'}$ are each independently hydrogen, cyano, hydroxy, amino, $H_2NC(O)—$, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)alkyl)_2$N—C(O)—, $(C_1-C_6)$alkylamino-, di$(C_1-C_4)$alkylamino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3- to 6-membered heterocycle, and a partially or fully saturated 3- to 8-membered carbocyclic ring, where said chemical moiety is optionally substituted, or either $R^{4e}$ or $R^{4e'}$ taken together with $R^{4b}$, $R^{4b'}$, $R^{4c}$, or $R^{4c'}$ forms a bond, a methylene bridge or an ethylene bridge; and $R^{4f}$ is hydrogen, an optionally substituted $(C_1-C_3)$alkyl, or taken together with $R^{4b}$, $R^{4b'}$, $R^{4c}$, or $R^{4c'}$ forms a bond, a methylene bridge, or an ethylene bridge; and $R^{4f'}$ is hydrogen, an optionally substituted $(C_1-C_3)$alkyl, or taken together with $R^{4b}$, $R^{4b'}$, $R^{4c}$, or $R^{4c'}$ forms a bond, a methylene bridge, or an ethylene bridge;

provided that when $R^4$ is a group of Formula (IA), then (a) at least one of $R^{4b}$, $R^{4b'}$, $R^{4c}$, $R^{4c'}$, $R^{4d}$, $R^{4d'}$, $R^{4d''}$, $R^{4e}$, $R^{4e'}$, $R^{4f}$ and $R^{4f'}$ is other than hydrogen, $(C_1-C_4)$alkyl, or halo-substituted $(C_1-C_4)$alkyl; and (b) Y is not oxygen, sulfur or —NH—, when X and Z are a bond, $—CH_2—$ or $—CH_2CH_2—$, and $R^{4b}$, $R^{4b'}$, $R^{4f}$ and $R^{4f'}$ are hydrogen; or (ii) a group having Formula (IC)

(IC)

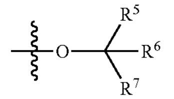

where $R^5$ and $R^6$ are each independently hydrogen or $(C_1-C_4)$alkyl, and $R^7$ is $(C_1-C_4)$alkyl-, halo-substituted $(C_1-C_4)$alkyl-, $(C_1-C_4)$alkoxy$(C_1-C_4)$alkyl-, $(C_1-C_4)$alkylamino$(C_1-C_4)$alkyl-, di$(C_1-C_4)$alkylamino$(C_1-C_4)$alkyl-, or a partially or fully saturated 4- to 6-membered heterocylic ring containing 1 to 2 heteroatoms independently selected from oxygen, sulfur or nitrogen, or $R^5$ and $R^6$ or $R^5$ and $R^7$ taken together form a 5- or 6-membered lactone, 4- to 6-member lactam, or a partially or fully saturated 4- to 6-membered heterocycle, where said 4- to 6- membered heterocycle contains 1 to 2 heteroatoms independently selected from oxygen, sulfur or nitrogen, and where said lactone, said lactam and said heterocycle are optionally substituted;

a pharmaceutically acceptable salt thereof, a prodrug of said compound or said salt, or a solvate or hydrate of said compound, said salt or said prodrug.

2. The compound of claim 1 wherein

X is $—C(R^{4c})(R^{4c'})—$, where $R^{4c}$ and $R^{4c'}$ are each independently hydrogen, $H_2NC(O)—$, an optionally substituted $(C_1-C_6)$alkyl, $(C_1-C_4)$alkyl-NH—C(O)—, or $((C_1-C_4)alkyl)_2$N—C(O)—, or either $R^{4c}$ or $R^{4c'}$ taken together with $R^{4e}$, $R^{4e'}$, $R^{4f}$, or $R^{4f'}$ forms a bond, a methylene bridge or an ethylene bridge;

Y is —$NR^{4d''}$—, $R^{4d''}$ is a hydrogen or a chemical moiety selected from the group consisting of $(C_1-C_6)$alkyl, $(C_3-C_6)$cycloalkyl, $(C_1-C_3)$alkylsulfonyl, $(C_1-C_3)$alkylaminosulfonyl, di$(C_1-C_3)$alkylaminosulfonyl, acyl, $(C_1-C_6)$alkyl-O—C(O)—, aryl, and heteroaryl, where said chemical moiety is optionally substituted;

Z is —$C(R^{4e})(R^{4e'})$—, where $R^{4e}$ and $R^{4e'}$ are each independently hydrogen, $H_2NC(O)$—, an optionally substituted $(C_1-C_6)$alkyl, $(C_1-C_4)$alkyl-NH—C(O)—, or $((C_1-C_4)alkyl)_2N$—C(O)—, or either $R^{4e}$ or $R^{4e'}$ taken together with $R^{4b}$, $R^{4b'}$, $R^{4c}$, or $R^{4c'}$ forms a bond, a methylene bridge or an ethylene bridge;

a pharmaceutically acceptable salt thereof, a prodrug of said compound or said salt, or a solvate or hydrate of said compound, said salt or said prodrug.

3. The compound of claim 2 wherein $R^{4d''}$ is a hydrogen or a chemical moiety selected from the group consisting of $(C_1-C_3)$alkylsulfonyl, $(C_1-C_3)$alkylaminosulfonyl, di$(C_1-C_3)$alkylaminosulfonyl, acyl, $(C_1-C_6)$alkyl-O—C(O)—, and heteroaryl, where said chemical moiety is optionally substituted;

a pharmaceutically acceptable salt thereof, a prodrug of said compound or said salt, or a solvate or hydrate of said compound, said salt or said prodrug.

4. The compound of claim 3 wherein $R^{4d''}$ is a hydrogen or a chemical moiety selected from the group consisting of $(C_1-C_3)$alkylsulfonyl, $(C_1-C_3)$alkylaminosulfonyl, di$(C_1-C_3)$alkylaminosulfonyl, acyl, and $(C_1-C_6)$alkyl-O—C(O)—,where said chemical moiety is optionally substituted with 1–3 fluorines, or $R^{4d''}$ is a heteroaryl, where said heteroaryl is optionally substituted with 1 to 2 substituents independently selected from the group consisting of chloro, fluoro, $(C_1-C_3)$alkoxy, $(C_1-C_3)$alkyl, and fluoro-substituted $(C_1-C_3)$alkyl;

a pharmaceutically acceptable salt thereof, a prodrug of said compound or said salt, or a solvate or hydrate of said compound, said salt or said prodrug.

5. The compound of claim 2, 3 or 4 wherein A and B are each independently a phenyl substituted with 1 to 3 substituents independently selected from the group consisting of halo, $(C_1-C_4)$alkoxy, $(C_1-C_4)$alkyl, halo-substituted $(C_1-C_4)$alkyl, and cyano;

a pharmaceutically acceptable salt thereof, a prodrug of said compound or said salt, or a solvate or hydrate of said compound, said salt or said prodrug.

6. The compound of claim 5 wherein A and B are each independently a phenyl substituted with 1 to 2 substituents independently selected from the group consisting of chloro, fluoro, $(C_1-C_4)$alkoxy, $(C_1-C_4)$alkyl, fluoro-substituted $(C_1-C_4)$alkyl), and cyano;

a pharmaceutically acceptable salt thereof, a prodrug of said compound or said salt, or a solvate or hydrate of said compound, said salt or said prodrug.

7. The compound of claim 6 wherein A is 2-chlorophenyl, 2-fluorophenyl, 2,4-dichlorophenyl, 2-fluoro-4-chlorophenyl, 2-chloro-4-fluorophenyl, or 2,4-difluorophenyl; and B is 4-chlorophenyl or 4-fluorophenyl;

a pharmaceutically acceptable salt thereof, a prodrug of said compound or said salt, or a solvate or hydrate of said compound, said salt or said prodrug.

8. The compound of claim 7 selected from the group consisting of 9-(4-chlorophenyl)-8-(2,4-dichlorophenyl)-6-(4-pyridin-2-ylpiperazin-1-yl)-9H-purine;

9-(4-chlorophenyl)-8-(2,4-dichlorophenyl)-6-(4-pyrimidin-2-ylpiperazin1-yl)-9H-purine; and 4-[9-(4-chlorophenyl)-8-(2-chlorophenyl)-9H-purin-6-yl]-piperazine-2-carboxylic acid methylamide;

a pharmaceutically acceptable salt thereof, or a solvate or hydrate of said compound or said salt.

9. The compound of claim 1 wherein Y is —$C(R^{4d})(R^{4d'})$—, where $R^{4d}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)alkyl)_2N$—C(O)—, $(C_1-C_6)$alkylamino-, $((C_1-C_4)alkyl)_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3- to 6-membered heterocycle, and a partially or fully saturated 3- to 8-membered carbocyclic ring, where said chemical moiety is optionally substituted, $R^{4d'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $(C_1-C_4)alkyl)_2N$—C(O)—, aryl, heteroaryl, a partially or fully saturated 3- to 6-membered heterocycle, and a partially or fully saturated 3- to 8-membered carbocyclic ring, where said chemical moiety is optionally substituted, or $R^{4d}$ and $R^{4d'}$ taken together form a partially or fully saturated, 3- to 6-membered heterocyclic ring, a 5- or 6-membered lactone ring, or a 4- to 6-membered lactam ring, where said heterocyclic ring, said lactone ring and said lactam ring are optionally substituted and said lactone ring and said lactam ring optionally contain an additional heteroatom selected from oxygen, nitrogen or sulfur;

a pharmaceutically acceptable salt thereof, a prodrug of said compound or said salt, or a solvate or hydrate of said compound, said salt or said prodrug.

10. The compound of claim 9 wherein $R^{4b}$, $R^{4b'}$, $R^{4f}$, and $R^{4f'}$ are all hydrogen;

$R^{4d}$ is amino, $(C_1-C_6)$alkylamino, di$(C_1-C_4)$alkylamino, $(C_3-C_6)$cycloalkylamino, acylamino, aryl$(C_1-C_4)$alkylamino-, heteroaryl$(C_1-C_4)$alkylamino-; and $R^{4d'}$ is $(C_1-C_6)$alkyl, $H_2NC(O)$—, $(C_1-C_4)$alkyl-NH—C(O)—, or $((C_1-C_4)alkyl)_2N$—C(O)—, or aryl;

a pharmaceutically acceptable salt thereof, a prodrug of said compound or said salt, or a solvate or hydrate of said compound, said salt or said prodrug.

11. The compound of claim 10 wherein

X is a bond or —$C(R^{4c})(R^{4c'})$—, where $R^{4c}$ and $R^{4c'}$ are each hydrogen; and Z is a bond or —$C(R^{4e})(R^{4e'})$—, where $R^{4e}$ and $R^{4e'}$ are each hydrogen;

a pharmaceutically acceptable salt thereof, a prodrug of said compound or said salt, or a solvate or hydrate of said compound, said salt or said prodrug.

12. The compound of claim 11 wherein $R^{4d}$ is amino, $(C_1-C_6)$alkylamino, di$(C_1-C_4)$alkylamino, $(C_3-C_6)$cycloalkylamino; and $R^{4d'}$ is $H_2NC(O)$—, $(C_1-C_4)$alkyl-NH—C(O)—, or $((C_1-C_4)alkyl)_2N$—C(O)—;

a pharmaceutically acceptable salt thereof, a prodrug of said compound or said salt, or a solvate or hydrate of said compound, said salt or said prodrug.

13. The compound of claim 9, 10, 11 or 12 wherein A and B are each independently a phenyl substituted with 1 to 3 substituents independently selected from the group consisting of halo, $(C_1–C_4)$alkoxy, $(C_1–C_4)$alkyl, halo-substituted $(C_1–C_4)$alkyl, and cyano;

a pharmaceutically acceptable salt thereof, a prodrug of said compound or said salt, or a solvate or hydrate of said compound, said salt or said prodrug.

14. The compound of claim 13 wherein A and B are each independently a phenyl substituted with 1 to 2 substituents independently selected from the group consisting of chloro, fluoro, $(C_1–C_4)$alkoxy, $(C_1–C_4)$alkyl, fluoro-substituted $(C_1–C_4)$alkyl), and cyano;

a pharmaceutically acceptable salt thereof, a prodrug of said compound or said salt, or a solvate or hydrate of said compound, said salt or said prodrug.

15. The compound of claim 14 wherein A is 2-chlorophenyl, 2-fluorophenyl, 2,4-dichlorophenyl, 2-fluoro-4-chlorophenyl, 2-chloro-4-fluorophenyl, or 2,4-difluorophenyl; and B is 4-chlorophenyl or 4-fluorophenyl;

a pharmaceutically acceptable salt thereof, a prodrug of said compound or said salt, or a solvate or hydrate of said compound, said salt or said prodrug.

16. The compound of claim 15 selected from the group consisting of

1-[9-(4-chlorophenyl)-8-(2-chlorophenyl)-9H-purin-6-yl]-3-ethylaminoazetidine-3-carboxylic acid amide;

1-[9-(4-chlorophenyl)-8-(2-chlorophenyl)-9H-purin-6-yl]-3-isopropylaminoazetidine-3-carboxylic acid amide;

1-[9-(4-chlorophenyl)-8-(2-fluorophenyl)-9H-purin-6-yl]-4-isopropylaminopiperidine-4-carboxylic acid amide;

1-[9-(4-chlorophenyl)-8-(2-chlorophenyl)-9H-purin-6-yl]-4-propylaminopiperidine-4-carboxylic acid amide;

1-[9-(4-chlorophenyl)-8-(2,4-dichlorophenyl)-9H-purin-6-yl]-4-propylaminopiperidine-4-carboxylic acid amide;

1-[9-(4-chlorophenyl)-8-(2-fluorophenyl)-9H-purin-6-yl]-4-propylaminopiperidine-4-carboxylic acid amide;

1-[9-(4-chlorophenyl)-8-(2-fluorophenyl)-2-methyl-9H-purin-6-yl-]4-isopropylaminopiperidine-4-carboxylic acid amide;

1-[9-(4-chlorophenyl)-8-(2-chlorophenyl)-9H-purin-6-yl]-4-pyrrolidin-1-yl-piperidine-4-carboxylic acid amide;

1-[9-(4-chlorophenyl)-8-(2-chlorophenyl)-9H-purin-6-yl]-4-ethylaminopiperidine-4-carboxylic acid amide;

1-[9-(4-chlorophenyl)-8-(2-chlorophenyl)-9H-purin-6-yl]-4-isopropylaminopiperidine-4-carboxylic acid amide;

4-amino-1-[9-(4-chlorophenyl)-8-(2-chlorophenyl)-9H-purin-6-yl]-piperidine-4-carboxylic acid amide; and 1-[9-(4-chlorophenyl)-8-(2,4-dichlorophenyl)-9H-purin-6-yl]-4-methylaminopiperidine-4-carboxylic acid amide;

a pharmaceutically acceptable salt thereof or a solvate or hydrate of said compound or said salt.

17. The compound of claim 16 selected from the group consisting of

1-[9-(4-chlorophenyl)-8-(2-fluorophenyl)-9H-purin-6-yl]-4-isopropylamino-piperidine-4-carboxylic acid amide;

1-[9-(4-chlorophenyl)-8-(2-chlorophenyl)-9H-purin-6-yl]-4-isopropylaminopiperidine-4-carboxylic acid amide;

4-amino-1-[9-(4-chlorophenyl)-8-(2-chlorophenyl)-9H-purin-6-yl]piperidine-4-carboxylic acid amide; and 1-[9-(4-chlorophenyl)-8-(2-chlorophenyl)-9H-purin-6-yl]-4-ethylamino-piperidine-4-carboxylic acid amide;

a pharmaceutically acceptable salt thereof or a solvate or hydrate of said compound or said salt.

18. The compound of claim 9 wherein $R^{4b}$, $R^{4b'}$, $R^{4f}$, and $R^{4f'}$ are all hydrogen;

$R^{4d}$ is hydrogen, hydroxy, amino, or a chemical moiety selected from the group consisting of $(C_1–C_6)$alkyl, $(C_1–C_6)$alkoxy, acyloxy, acyl, $(C_1–C_3)$alkyl-O—C(O)—, $(C_1–C_6)$alkylamino-, and di$(C_1–C_4)$alkylamino-, where said chemical moiety is optionally substituted; and $R^{4d'}$ is hydrogen, or a chemical moiety selected from the group consisting of $(C_1–C_6)$alkyl, aryl and heteroaryl, where said chemical moiety is optionally substituted;

a pharmaceutically acceptable salt thereof, a prodrug of said compound or said salt, or a solvate or hydrate of said compound, said salt or said prodrug.

19. The compound of claim 18 wherein

X is —$C(R^{4c})(R^{4c'})$—, where $R^{4c}$ and $R^{4c'}$ are each independently hydrogen or an optionally substituted $(C_1–C_6)$alkyl, or either $R^{4c}$ or $R^{4c'}$ taken together with $R^{4e}$ or $R^{4e'}$ forms a bond, a methylene bridge or an ethylene bridge; and Z is —$C(R^{4e})(R^{4e'})$—, where $R^{4e}$ and $R^{4e'}$ are each independently hydrogen or an optionally substituted $(C_1–C_6)$alkyl, or either $R^{4e}$ or $R^{4e'}$ taken together with $R^{4c}$ or $R^{4c'}$ forms a bond, a methylene bridge or an ethylene bridge;

a pharmaceutically acceptable salt thereof, a prodrug of said compound or said salt, or a solvate or hydrate of said compound, said salt or said prodrug.

20. The compound of claim 19 wherein $R^{4c}$ and $R^{4c'}$ are each hydrogen or either $R^{4c}$ or $R^{4c'}$ taken together with $R^{4e}$ or $R^{4e'}$ forms a bond;

$R^{4d}$ is hydrogen, hydroxy, amino, or a chemical moiety selected from the group consisting of $(C_1–C_6)$alkoxy, acyl, $(C_1–C_6)$alkylamino-, and di$(C_1–C_4)$alkylamino-;

$R^{4d'}$ is hydrogen, or a chemical moiety selected from the group consisting of $(C_1–C_6)$alkyl and aryl, where said chemical moiety is optionally substituted; and $R^{4e}$ and $R^{4e'}$ are hydrogen or either $R^{4e}$ or $R^{4e'}$ taken together with $R^{4c}$ or $R^{4c'}$ forms a bond;

a pharmaceutically acceptable salt thereof, a prodrug of said compound or said salt, or a solvate or hydrate of said compound, said salt or said prodrug.

21. The compound of claim 18, 19, or 20 wherein A and B are each independently a phenyl substituted with 1 to 3 substituents independently selected from the group consisting of halo, $(C_1–C_4)$alkoxy, $(C_1–C_4)$alkyl, halo-substituted $(C_1–C_4)$alkyl, and cyano;

a pharmaceutically acceptable salt thereof, a prodrug of said compound or said salt, or a solvate or hydrate of said compound, said salt or said prodrug.

22. The compound of claim 21 wherein A and B are each independently a phenyl substituted with 1 to 2 substituents independently selected from the group consisting of chloro, fluoro, $(C_1–C_4)$alkoxy, $(C_1–C_4)$alkyl, fluoro-substituted $(C_1–C_4)$alkyl), and cyano;

a pharmaceutically acceptable salt thereof, a prodrug of said compound or said salt, or a solvate or hydrate of said compound, said salt or said prodrug.

23. The compound of claim 22 wherein A is 2-chlorophenyl, 2-fluorophenyl, 2,4-dichlorophenyl, 2-fluoro-4-chlorophenyl, 2-chloro-4-fluorophenyl, or 2,4-difluorophenyl; and B is 4-chlorophenyl or 4-fluorophenyl;

a pharmaceutically acceptable salt thereof, a prodrug of said compound or said salt, or a solvate or hydrate of said compound, said salt or said prodrug.

24. The compound of claim 23 selected from the group consisting of

1-{1-[9-(4-chlorophenyl)-8-(2-chlorophenyl)-9H-purin-6-yl]-4-phenylpiperidin-4-yl}-ethanone;

[3-[9-(4-chlorophenyl)-8-(2,4-dichlorophenyl)-9H-purin-6-yl]-3-(1α,5α,6α)-azabicyclo[3.1.0]hex-6-yl}-dimethylamine;

1-[9-(4-chlorophenyl)-8-(2-chlorophenyl)-9H-purin-6-yl]-4-(4-fluorophenyl)-piperidin-4-ol;

1-[9-(4-chlorophenyl)-8-(2-chlorophenyl)-9H-purin-6-yl]-4-phenylpiperidin-4-ol; and 4-benzyl-1-[9-(4-chlorophenyl)-8-(2-chlorophenyl)-9H-purin-6-yl]-piperidin-4-ol;

a pharmaceutically acceptable salt thereof, or a solvate or hydrate of said compound or said salt.

25. The compound of claim 9 wherein $R^{4b}$, $R^{4b'}$, $R^{4f}$, and $R^{4f'}$ are all hydrogen; and $R^{4d}$ and $R^{4d'}$ taken together form a partially or fully saturated 3- to 6-membered heterocyclic ring, a 5- or 6-membered lactone ring, or a 4- to 6-membered lactam ring, where said heterocyclic ring, said lactone ring and said lactam ring are optionally substituted and said lactone ring or said lactam ring optionally contains an additional heteroatom selected from oxygen, nitrogen or sulfur;

a pharmaceutically acceptable salt thereof, a prodrug of said compound or said salt, or a solvate or hydrate of said compound, said salt or said prodrug.

26. The compound of claim 25 wherein

X is a bond, $-CH_2CH_2-$ or $-C(R^{4c})(R^{4c'})-$, where $R^{4c}$ and $R^{4c'}$ are each independently hydrogen or an optionally substituted $(C_1-C_6)$alkyl, or either $R^{4c}$ or $R^{4c'}$ taken together with $R^{4e}$ or $R^{4e'}$ forms a bond, a methylene bridge or an ethylene bridge; and Z is a bond, $-CH_2CH_2-$ or $-C(R^{4e})(R^{4e'})-$, where $R^{4e}$ and $R^{4e'}$ are each independently hydrogen or an optionally substituted $(C_1-C_6)$alkyl, or either $R^{4e}$ or $R^{4e'}$ taken together with $R^{4c}$ or $R^{4c'}$ forms a bond, a methylene bridge or an ethylene bridge;

a pharmaceutically acceptable salt thereof, a prodrug of said compound or said salt, or a solvate or hydrate of said compound, said salt or said prodrug.

27. The compound of claim 25 wherein $R^{4d}$ and $R^{4d'}$ taken together form a 5 or 6 membered lactam ring, where said lactam ring is optionally substituted and optionally contains an additional heteroatom selected from nitrogen or oxygen;

a pharmaceutically acceptable salt thereof, a prodrug of said compound or said salt, or a solvate or hydrate of said compound, said salt or said prodrug.

28. The compound of claim 27 wherein

X is a bond or $-C(R^{4c})(R^{4c'})-$, where $R^{4c}$ and $R^{4c'}$ are each hydrogen; and Z is a bond or $-C(R^{4e})(R^{4e'})$, where $R^{4e}$ and $R^{4e'}$ are each hydrogen;

a pharmaceutically acceptable salt thereof, a prodrug of said compound or said salt, or a solvate or hydrate of said compound, said salt or said prodrug.

29. The compound of claim 25, 26, 27 or 28 wherein A and B are each independently a phenyl substituted with 1 to 3 substituents independently selected from the group consisting of halo, $(C_1-C_4)$alkoxy, $(C_1-C_4)$alkyl, halo-substituted $(C_1-C_4)$alkyl, and cyano;

a pharmaceutically acceptable salt thereof, a prodrug of said compound or said salt, or a solvate or hydrate of said compound, said salt or said prodrug.

30. The compound of claim 29 wherein A and B are each independently a phenyl substituted with 1 to 2 substituents independently selected from the group consisting of chloro, fluoro, $(C_1-C_4)$alkoxy, $(C_1-C_4)$alkyl, fluoro-substituted $(C_1-C_4)$alkyl), and cyano;

a pharmaceutically acceptable salt thereof, a prodrug of said compound or said salt, or a solvate or hydrate of said compound, said salt or said prodrug.

31. The compound of claim 30 wherein A is 2-chlorophenyl, 2-fluorophenyl, 2,4-dichlorophenyl, 2-fluoro-4-chlorophenyl, 2-chloro4-fluorophenyl, or 2,4-difluorophenyl; and B is 4-chlorophenyl or 4-fluorophenyl;

a pharmaceutically acceptable salt thereof, a prodrug of said compound or said salt, or a solvate or hydrate of said compound, said salt or said prodrug.

32. The compound of claim 28 selected from the group consisting of

8-[9-(4-chlorophenyl)-8-(2-chlorophenyl)-9H-purin-6-yl]-1-isopropyl-1,3,8-triazaspiro[4.5]decan-4-one;

8-[9-(4-chlorophenyl)-8-(2,4-dichlorophenyl)-9H-purin-6-yl]-1isopropyl-1,3,8-triazaspiro[4.5]decan-4-one; and 9-[9-(4-chlorophenyl)-8-(2-chlorophenyl)-9H-purin-6-yl]-1-methyl-4-oxa-1,9-diazaspiro[5.5]undecan-2-one;

a pharmaceutically acceptable salt thereof or a solvate or hydrate of said compound or said salt.

33. The compound of claim 32 which is 8-[9-(4-chlorophenyl)-8-(2-chlorophenyl)-9H-purin-6-yl]-1-isopropyl-1,3,8-triazaspiro[4.5]decan-4-one;

a pharmaceutically acceptable salt thereof or a solvate or hydrate of said compound or said salt.

34. The compound of claim 1 wherein $R^4$ is a group of Formula (IB)

(IB)

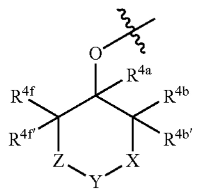

where $R^{4a}$ is as defined in claim 1;

$R^{4b}$ is hydrogen, an optionally substituted $(C_1-C_3)$alkyl, or taken together with $R^{4e}$, $R^{4e'}$, $R^{4f}$, or $R^{4f'}$ forms a bond, a methylene bridge, or an ethylene bridge;

$R^{4b'}$ is hydrogen, an optionally substituted $(C_1-C_3)$alkyl, or taken together with $R^{4e}$, $R^{4e'}$, $R^{4f}$, or $R^{4f'}$ forms a bond, a methylene bridge, or an ethylene bridge;

X is a bond, $-CH_2CH_2-$ or $-C(R^{4c})(R^{4c'})-$, where $R^{4c}$ is hydrogen, cyano, hydroxy, amino, $H_2NC(O)-$, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $(C_1-C_4)$alkyl$)_2$N—C(O)—, $(C_1-C_6)$alkylamino-, $((C_1-C_4)$alkyl$)_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3- to 6-membered heterocycle, and a partially or fully saturated 3- to 8-membered carbocyclic ring, where said chemical moiety is optionally substituted, or $R^{4c}$ taken together with $R^{4e}$, $R^{4e'}$, $R^{4f}$, or $R^{4f'}$ forms a bond, a methylene bridge, or an ethylene bridge, and $R^{4c'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $((C_1-C_4)alkyl)_2N$—C(O)—, aryl, heteroaryl, a partially or fully saturated 3- to 6-membered heterocycle, and a partially or fully saturated 3- to 8-membered carbocyclic ring, where said chemical moiety is optionally substituted, or $R^{4c'}$ taken together with $R^{4e}$, $R^{4e'}$, $R^{4f}$, or $R^{4f'}$ forms a bond, a methylene bridge, or an ethylene bridge;

Y is oxygen, sulfur, —C(O)—, or —$C(R^{4d})(R^{4d'})$—, where $R^{4d}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)alkyl)_2N$—C(O)—, $(C_1-C_6)$alkylamino-, $((C_1-C_4)alkyl)_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3- to 6-membered heterocycle, and a partially or fully saturated 3- to 8-membered carbocyclic ring, where said chemical moiety is optionally substituted, and $R^{4d'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $((C_1-C_4)alkyl)_2N$—C(O)—, aryl, heteroaryl, a partially or fully saturated 3- to 6-membered heterocycle, and a partially or fully saturated 3- to 8-membered carbocyclic ring, where said chemical moiety is optionally substituted, or $R^{4d}$ and $R^{4d'}$ taken together form a partially or fully saturated 3- to 6-membered heterocyclic ring, a 5- or 6-membered lactone ring, or a 4- to 6-membered lactam ring, where said heterocyclic ring, said lactone ring and said lactam ring are optionally substituted and said lactone ring and said lactam ring optionally contain an additional heteroatom selected from oxygen, nitrogen or sulfur;

Y is —$NR^{4d''}$—, where $R^{4d''}$ is a hydrogen or a chemical moiety selected from the group consisting of $(C_1-C_6)$alkyl, $(C_3-C_6)$cycloalkyl, $(C_1-C_3)$alkylsulfonyl-, $(C_1-C_3)$alkylaminosulfonyl-, di$(C_1-C_3)$alkylaminosulfonyl-, acyl, $(C_1-C_6)$alkyl-O—C(O)—, aryl, and heteroaryl, where said chemical moiety is optionally substituted;

Z is a bond, —$CH_2CH_2$—, or —$C(R^{4e})(R^{4e'})$—, where $R^{4e}$ is hydrogen, cyano, hydroxy, amino, $H_2NC(O)$—, or a chemical moiety selected from the group consisting of $(C_1-C_6)$alkyl, $(C_1-C_6)$alkoxy, acyloxy, acyl, $(C_1-C_3)$alkyl-O—C(O)—, $(C_1-C_4)$alkyl-NH—C(O)—, $((C_1-C_4)alkyl)_2N$—C(O)—, $(C_1-C_6)$alkylamino-, $((C_1-C_4)alkyl)_2$amino-, $(C_3-C_6)$cycloalkylamino-, acylamino-, aryl$(C_1-C_4)$alkylamino-, heteroaryl$(C_1-C_4)$alkylamino-, aryl, heteroaryl, a partially or fully saturated 3- to 6-membered heterocycle, and a partially or fully saturated 3- to 8-membered carbocyclic ring, where said chemical moiety is optionally substituted, or $R^{4e}$ taken together with $R^{4b}$, $R^{4b'}$, $R^{4c}$, or $R^{4c'}$ forms a bond, a methylene bridge, or an ethylene bridge, and $R^{4e'}$ is hydrogen, $H_2NC(O)$—, or a chemical moiety selected from the group consisting of $(C_1-C_6)$alkyl, acyl, $(C_1-C_3)$alkyl-O—C(O)—, $(C_1-C_4)$alkyl-NH—C(O)—, $((C_1-C_4)alkyl)_2N$—C(O)—, aryl, heteroaryl, a partially or fully saturated 3- to 6-membered heterocycle, and a partially or fully saturated 3- to 8-membered carbocyclic ring, where said chemical moiety is optionally substituted, or $R^{4e'}$ taken together with $R^{4b}$, $R^{4b'}$, $R^{4c}$, or $R^{4c'}$ forms a bond, a methylene bridge, or an ethylene bridge;

$R^{4f}$ is hydrogen, an optionally substituted $(C_1-C_3)$alkyl, or taken together with $R^{4b}$, $R^{4b'}$, $R^{4c}$, or $R^{4c'}$ forms a bond, a methylene bridge, or an ethylene bridge; and $R^{4f'}$ is hydrogen, an optionally substituted $(C_1-C_3)$alkyl, or taken together with $R^{4b}$, $R^{4b'}$, $R^{4c}$, or $R^{4c'}$ forms a bond, a methylene bridge, or an ethylene bridge;

a pharmaceutically acceptable salt thereof, a prodrug of said compound or said salt, or a solvate or hydrate of said compound, said salt or said prodrug.

35. The compound of claim 34 wherein $R^{4a}$, $R^{4b}$, $R^{4b'}$, $R^{4f}$ and $R^{4f'}$ are each hydrogen;

a pharmaceutically acceptable salt thereof, a prodrug of said compound or said salt, or a solvate or hydrate of said compound, said salt or said prodrug.

36. The compound of claim 35 wherein

X is a bond, —$CH_2CH_2$— or —$C(R^{4c})(R^{4c'})$—, where $R^{4c}$ and $R^{4c'}$ are each independently hydrogen or $(C_1-C_6)$alkyl;

Y is —$NR^{4d''}$—, where $R^{4d''}$ is hydrogen or a chemical moiety selected from the group consisting of $(C_1-C_6)$alkyl, $(C_3-C_6)$cycloalkyl, $(C_1C_3)$alkylsulfonyl-, $(C_1-C_3)$alkylaminosulfonyl-, di$(C_1-C_3)$alkylaminosulfonyl-, acyl, $(C_1-C_6)$alkyl-O—C(O)—, aryl, and heteroaryl, where said chemical moiety is optionally substituted;

Z is a bond, —$CH_2CH_2$— or —$C(R^{4c})(R^{4c'})$—, where $R^{4c}$ and $R^{4c'}$ are each independently hydrogen or $(C_1-C_6)$alkyl;

a pharmaceutically acceptable salt thereof, a prodrug of said compound or said salt, or a solvate or hydrate of said compound, said salt or said prodrug.

37. The compound of claim 35 or 36 wherein A and B are each independently a phenyl substituted with 1 to 3 substituents independently selected from the group consisting of halo, $(C_1-C_4)$alkoxy, $(C_1-C_4)$alkyl, halo-substituted $(C_1-C_4)$alkyl, and cyano;

a pharmaceutically acceptable salt thereof, a prodrug of said compound or said salt, or a solvate or hydrate of said compound, said salt or said prodrug.

38. The compound of claim 37 wherein A and B are each independently a phenyl substituted with 1 to 2 substituents independently selected from the group consisting of chloro, fluoro, $(C_1-C_4)$alkoxy, $(C_1-C_4)$alkyl, fluoro-substituted $(C_1-C_4)$alkyl), and cyano;

a pharmaceutically acceptable salt thereof, a prodrug of said compound or said salt, or a solvate or hydrate of said compound, said salt or said prodrug.

39. The compound of claim 38 wherein A is 2-chlorophenyl, 2-fluorophenyl, 2,4-dichlorophenyl, 2-fluoro-4-chlorophenyl, 2-chloro-4-fluorophenyl, or 2,4-difluorophenyl; and B is 4-chlorophenyl or 4-fluorophenyl;

a pharmaceutically acceptable salt thereof, a prodrug of said compound or said salt, or a solvate or hydrate of said compound, said salt or said prodrug.

40. The compound of claim 39 selected from the group consisting of 6-(1 -benzylpyrrolidin-3-yloxy)-9-(4-chlorophenyl)-8-(2,4-dichlorophenyl)-9H-purine; and 9-(4-chlorophenyl)-6-(1-cyclohexylazetidin-3-yloxy)-8-(2,4-dichlorophenyl)-9H-purine;

a pharmaceutically acceptable salt thereof or a solvate or hydrate of said compound or said salt.

41. The compound of claim 1 wherein $R^4$ is a group having Formula (IC)

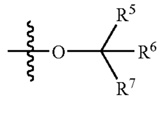

(IC)

where $R^5$ and $R^6$ are each independently hydrogen or $(C_1–C_4)$alkyl, and $R^7$ is $(C_1–C_4)$alkyl-, halo-substituted $(C_1–C_4)$alkyl-, $(C_1–C_4)$alkoxy$(C_1–C_4)$alkyl-, $(C_1–C_4)$alkylamino$(C_1–C_4)$alkyl-, di$(C_1–C_4)$alkylamino$(C_1–C_4)$alkyl-, or a partially or fully saturated 4- to 6-membered heterocylic ring containing 1 to 2 heteroatoms independently selected from oxygen, sulfur or nitrogen, or $R^5$ and $R^6$, or $R^5$ and $R^7$ taken together form a 5- or 6-membered lactone, 4- to 6-membered lactam, or a partially or fully saturated 4- to 6-membered heterocycle, where said 4- to 6-membered heterocycle contains 1 to 2 heteroatoms independently selected from oxygen, sulfur or nitrogen, and where said lactone, said lactam and said heterocycle are optionally substituted;

a pharmaceutically acceptable salt thereof, a prodrug of said compound or said salt, or a solvate or hydrate of said compound, said salt or said prodrug.

42. The compound of claim 41 wherein $R^5$ and $R^6$ are each independently hydrogen or $(C_1–C_4)$alkyl, and $R^7$ is $(C_1–C_4)$alkyl;

a pharmaceutically acceptable salt thereof, a prodrug of said compound or said salt, or a solvate or hydrate of said compound, said salt or said prodrug.

43. The compound of claim 42 wherein A and B are each independently a phenyl substituted with 1 to 3 substituents independently selected from the group consisting of halo, $(C_1–C_4)$alkoxy, $(C_1–C_4)$alkyl, halo-substituted $(C_1–C_4)$alkyl, and cyano;

a pharmaceutically acceptable salt thereof, a prodrug of said compound or said salt, or a solvate or hydrate of said compound, said salt or said prodrug.

44. The compound of claim 43 wherein A and B are each independently a phenyl substituted with 1 to 2 substituents independently selected from the group consisting of chloro, fluoro, $(C_1–C_4)$alkoxy, $(C_1–C_4)$alkyl, fluoro-substituted $(C_1–C_4)$alkyl), and cyano;

a pharmaceutically acceptable salt thereof, a prodrug of said compound or said salt, or a solvate or hydrate of said compound, said salt or said prodrug.

45. The compound of claim 44 wherein A is 2-chlorophenyl, 2-fluorophenyl, 2,4-dichlorophenyl, 2-fluoro-4-chlorophenyl, 2-chloro-4-fluorophenyl, or 2,4-difluorophenyl; and B is 4-chlorophenyl or 4-fluorophenyl;

a pharmaceutically acceptable salt thereof, a prodrug of said compound or said salt, or a solvate or hydrate of said compound, said salt or said prodrug.

46. The compound of claim 45 selected from the group consisting of 6-tert-butoxy-9-(4-chlorophenyl)-8-(2,4-dichlorophenyl)-9H-purine; and 9-(4-chlorophenyl)-8-(2,4-dichlorophenyl)-6-isopropoxy-9H-purine;

a pharmaceutically acceptable salt thereof or a solvate or hydrate of said compound or said salt.

47. A pharmaceutical composition comprising (1) a compound of claim 1, a prodrug of said compound, a pharmaceutically acceptable salt of said compound or said prodrug, or a solvate or hydrate of said compound, said prodrug, or said salt; and (2) a pharmaceutically acceptable excipient, diluent, or carrier.

48. The composition of claim 47 further comprising at least one additional pharmaceutical agent, wherein said additional pharmaceutical agent is a nicotine receptor partial agonist, an opioid antagonist, a dopaminergic agent, an attention deficit disorder agent, or an anti-obesity agent.

49. The composition of claim 48 wherein said anti-obesity agent is selected from the group consisting of an apo-B/MTP inhibitor, an 11β-hydroxy steroid dehydrogenase-1 inhibitor, peptide $YY_{3-36}$, a MCR-4 agonist, a CCK-A agonist, a monoamine reuptake inhibitor, a sympathomimetic agent, a $\beta_3$ adrenergic receptor agonist, a dopamine agonist, a melanocyte-stimulating hormone receptor analog, a 5-HT2c receptor agonist, a melanin concentrating hormone antagonist, leptin, a leptin analog, a leptin receptor agonist, a galanin receptor antagonist, a lipase inhibitor, a bombesin receptor agonist, a neuropeptide-Y receptor antagonist, a thyromimetic agent, dehydroepiandrosterone or analog thereof, a glucocorticoid receptor antagonist, an orexin receptor antagonist, a glucagon-like peptide-1 receptor agonist, a ciliary neurotrophic factor, a human agouti-related protein antagonist, a ghrelin receptor antagonist, a histamine 3 receptor antagonist or inverse agonist, and a neuromedin U receptor agonist.

50. The composition of claim 48 wherein said additional pharmaceutical agent is an opioid antagonist.

51. A compound which is 1-[9-(4-chlorophenyl)-8-(2-chlorophenyl)-9H-purin-6-yl]-4-ethylaminopiperidine-4-carboxylic acid amide;

a pharmaceutically acceptable salt thereof or a solvate or hydrate of said compound or said salt.

52. The compound of claim 51 wherein said compound is a mesylate, besylate or hydrochloride salt; or a solvate or hydrate of said salt.

53. The compound of claim 46 which is a hydrochloride salt or hydrate of said hydrochloride salt.

54. A compound having the following structure

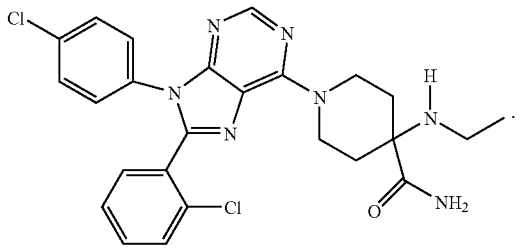

55. The composition of claim 47 wherein said compound of claim 1 is 1-[9-(4-chlorophenyl)-8-(2-chlorophenyl)-9H- purin-6-yl-]-4-ethylaminopiperidine-4-carboxylic acid amide;

a pharmaceutically acceptable salt thereof or a solvate or hydrate of said compound or said salt.

56. The composition of claim 48 wherein said compound of claim 1 is 1-[9-(4-chlorophenyl)-8-(2-chlorophenyl)-9H-purin-6-yl]-4-ethylaminopiperdine-4-carboxylic acid amide;

a pharmaceutically acceptable salt thereof or a solvate or hydrate of said compound or said salt.

57. The composition of claim 56 wherein said additional pharmaceutical agent is an opioid antagonist or an anti-obesity agent.

* * * * *

UNITED STATES PATENT AND TRADEMARK OFFICE

CERTIFICATE OF CORRECTION

PATENT NO. : 7,129,239 B2
APPLICATION NO. : 10/689381
DATED : October 31, 2006
INVENTOR(S) : David A. Griffith It is certified that error appears in the above-identified patent and that said Letters Patent is hereby corrected as shown below:

Column 156, line 50, delete the reference to claim "46" and insert --52-- in Claim 53.

Signed and Sealed this

Twenty-seventh Day of May, 2008

JON W. DUDAS
*Director of the United States Patent and Trademark Office*